(12) United States Patent
Kim et al.

(10) Patent No.: US 9,752,151 B2
(45) Date of Patent: Sep. 5, 2017

(54) COMPOSITION FOR TREATMENT OR METASTASIS SUPPRESSION OF CANCERS WHICH INCLUDES P34 EXPRESSION INHIBITOR OR ACTIVITY INHIBITOR AS ACTIVE INGREDIENT

(71) Applicants: THE ASAN FOUNDATION, Seoul (KR); UNIVERSITY OF ULSAN FOUNDATION FOR INDUSTRY COOPERATION, Ulsan (KR)

(72) Inventors: Tae Won Kim, Seoul (KR); Dong Hoon Jin, Seoul (KR); Seung Woo Hong, Seoul (KR); Jai Hee Moon, Seoul (KR); Jae Sik Shin, Seoul (KR); Jin Sun Kim, Seoul (KR); Kyung Ah Jung, Seoul (KR); Jung Shin Lee, Seoul (KR); Eun Kyung Choi, Seoul (KR); Jae Lyun Lee, Seoul (KR); Yong Sang Hong, Seoul (KR); Kyu Pyo Kim, Seoul (KR); Ky Youb Nam, Seoul (KR); Bong Cheol Kim, Seoul (KR)

(73) Assignees: The Asan Foundation, Seoul (KR); University of Ulsan Foundation for Industry Cooperation, Ulsan (KR)

( * ) Notice: Subject to any disclaimer, the term of this patent is extended or adjusted under 35 U.S.C. 154(b) by 0 days.

(21) Appl. No.: 14/779,874

(22) PCT Filed: Mar. 27, 2014

(86) PCT No.: PCT/KR2014/002617
§ 371 (c)(1),
(2) Date: Sep. 24, 2015

(87) PCT Pub. No.: WO2014/157965
PCT Pub. Date: Oct. 2, 2014

(65) Prior Publication Data
US 2016/0040168 A1 Feb. 11, 2016

(30) Foreign Application Priority Data
Mar. 27, 2013 (KR) ........................ 10-2013-0032957

(51) Int. Cl.
| | |
|---|---|
| *A01N 43/52* | (2006.01) |
| *A61K 31/415* | (2006.01) |
| *C12N 15/113* | (2010.01) |
| *A61K 31/4245* | (2006.01) |
| *C12Q 1/68* | (2006.01) |
| *G01N 33/50* | (2006.01) |
| *A23L 33/13* | (2016.01) |

(52) U.S. Cl.
CPC .......... *C12N 15/1137* (2013.01); *A23L 33/13* (2016.08); *A61K 31/4245* (2013.01); *C12N 15/113* (2013.01); *C12Q 1/6886* (2013.01); *G01N 33/5011* (2013.01); *A23V 2002/00* (2013.01); *C12N 2310/11* (2013.01); *C12N 2310/12* (2013.01); *C12N 2310/122* (2013.01); *C12N 2310/14* (2013.01); *C12N 2310/531* (2013.01); *C12Q 2600/136* (2013.01); *C12Q 2600/158* (2013.01)

(58) Field of Classification Search
USPC ......................................................... 514/387
See application file for complete search history.

(56) References Cited

U.S. PATENT DOCUMENTS 5,625,031 A * 4/1997 Webster ............. C07K 14/4736
530/300

FOREIGN PATENT DOCUMENTS

| JP | 07-316196 | 12/1995 |
|---|---|---|
| WO | 96/17605 A1 | 6/1996 |

OTHER PUBLICATIONS

Cheng et. al. (Journal of Cardiovascular Pharmacology (2000) 35:1-6).*
Hong et. al. (Cell Death and Differentiation (2014) 21:146-160).*
Hong, et al., "p34SEI-1 Inhibits Apoptosis through the Stabilization of the X-Linked Inhibitor of Apoptosis Protein: p34SEI-1 as a Novel Target for Anti-Breast Cancer Strategies," Cancer Res, No. 69, vol. 3, pp. 741-746, 2009.
Hong, et al., "p34 is a novel regulator of the oncogenic behavior of NEDD4-1 and PTEN," Cell Death and Differeatiation, vol. 21, pp. 146-160, 2014.

(Continued)

*Primary Examiner* — Marcos Sznaidman
(74) *Attorney, Agent, or Firm* — McDonnell Boehnen Hulbert & Berghoff LLP

(57) ABSTRACT

The present invention relates to a composition for treatment or metastasis suppression of cancers which includes a p34 expression inhibitor or activity inhibitor as an active ingredient. According to the present invention, the p34 protein knock-down causes monoubiquitination of PTEN and accordingly nuclear localization of PTEN is induced, as a result, an Akt pathway which is related to survival, proliferation, invasive properties and metastatic properties of tumors is inhibited, and thus there is an effect of significantly reducing clonogenic potential and tumor forming potential of various cancer cells which simultaneously express PTEN and NEDD4-1. Consequently, the p34 gene expression inhibitor or p34 protein activity inhibitor according to the present invention can be effectively used as a treatment agent or a metastasis suppression agent for cancers.

2 Claims, 57 Drawing Sheets

(56) References Cited

OTHER PUBLICATIONS

Klaunig, et al., "The Role of Oxidative Stress in Carcinogenesis," Annu Rev Pharmacol Toxicol, vol. 44, pp. 239-267, 2004.

Li, et al., "Characterization of a Novel Mechanism of Genomic Instability Involving the SEI1/SET/NM23H1 Pathway in Esophageal Cancers," Cancer Res, vol. 70, pp. 5695-5705, 2010.

Shi, et al., "Influence of the Calmodiulin Antagonist EBB on Cyclin B1 and Cdc2-p34 in Human Drug-resistant Breast Cancer MCF-7/ADR Cells," Clin J Clin Oncol, vol. 5, pp. 108-112, 2008.

Sugimoto, et al., "Regulation of CDK4 activity by a novel CDK4-binding protein, p34SEI-1," Genes & Development, vol. 13, pp. 3027-3033, 1999.

Tang, et al, "Oncogenic Transformation by SEI-1 Is Associated with Chromosomal Instability," Cancer Res, vol. 65, No. 15, pp. 6504-6508, 2005.

Takeshi Fujita, et al. Cancer Science, 104(2): 214-222, Dec. 13, 2012.

International Search report for PCT/KR2014/002617, mailed Jun. 23, 2014.

\* cited by examiner

[Fig 1]
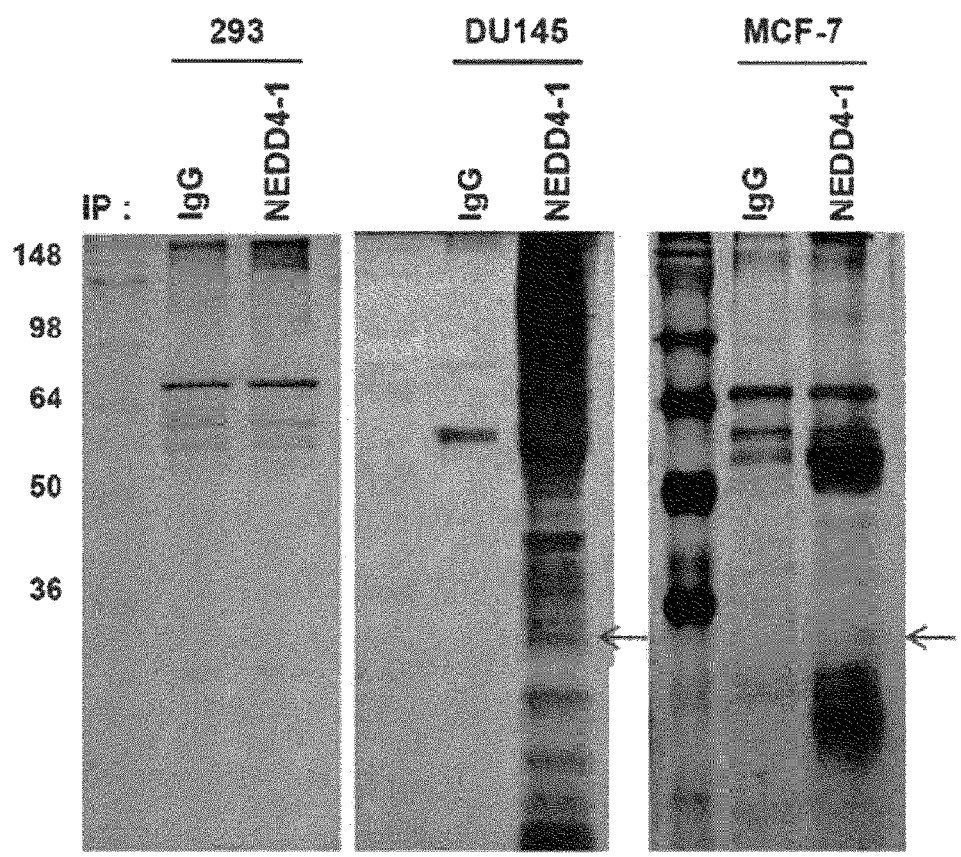

[Fig 2]
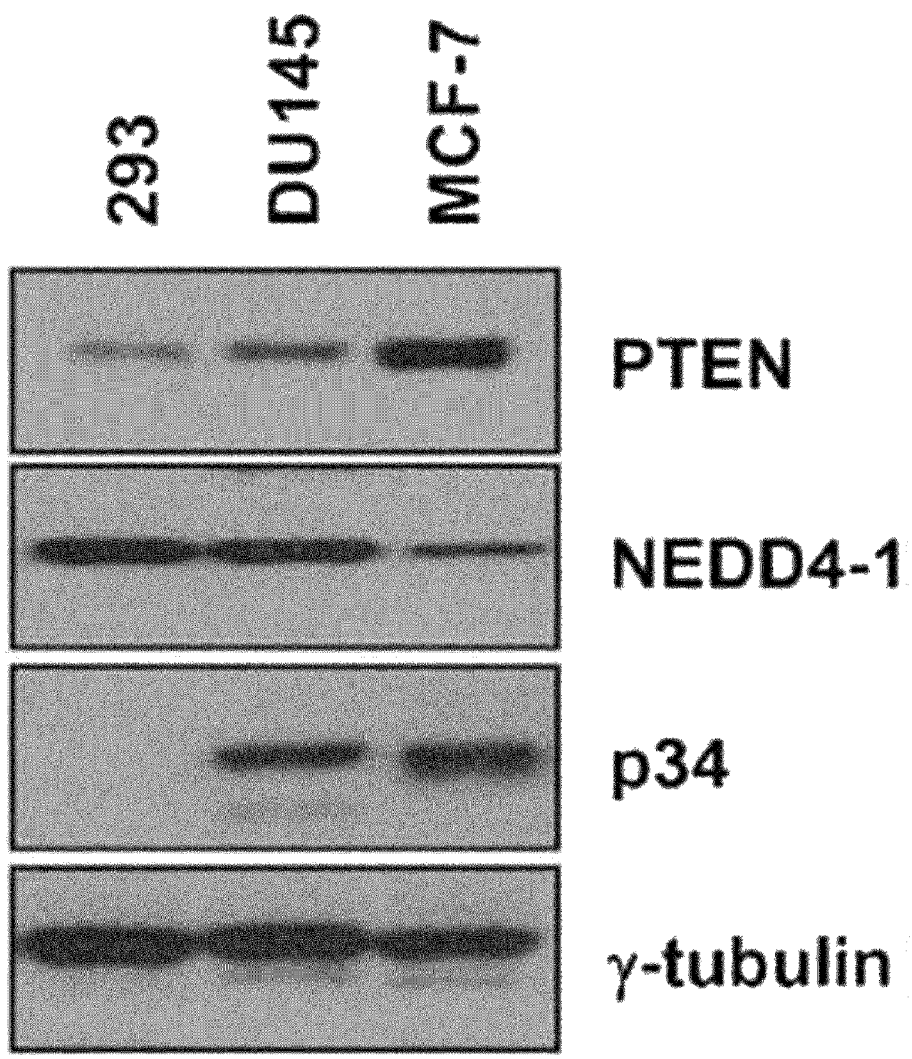

[Fig 3]
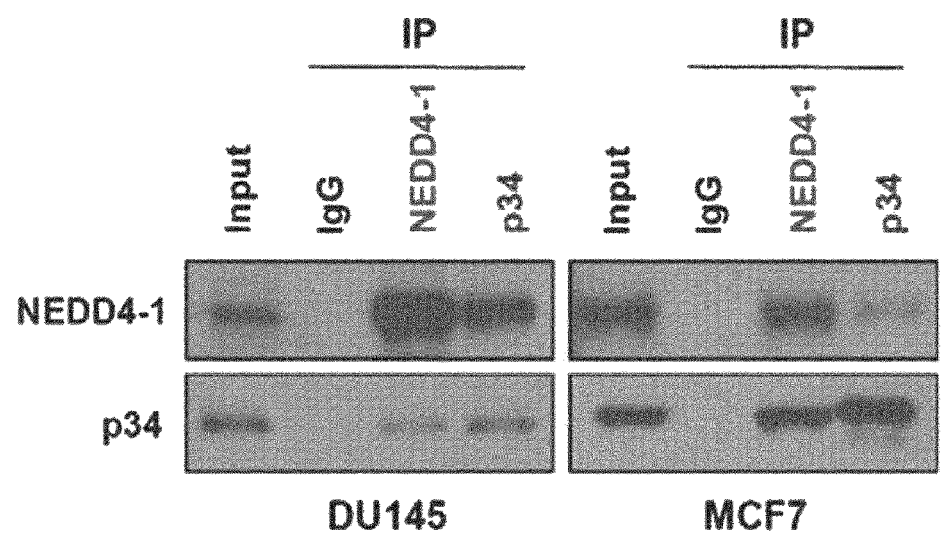

[Fig 4]
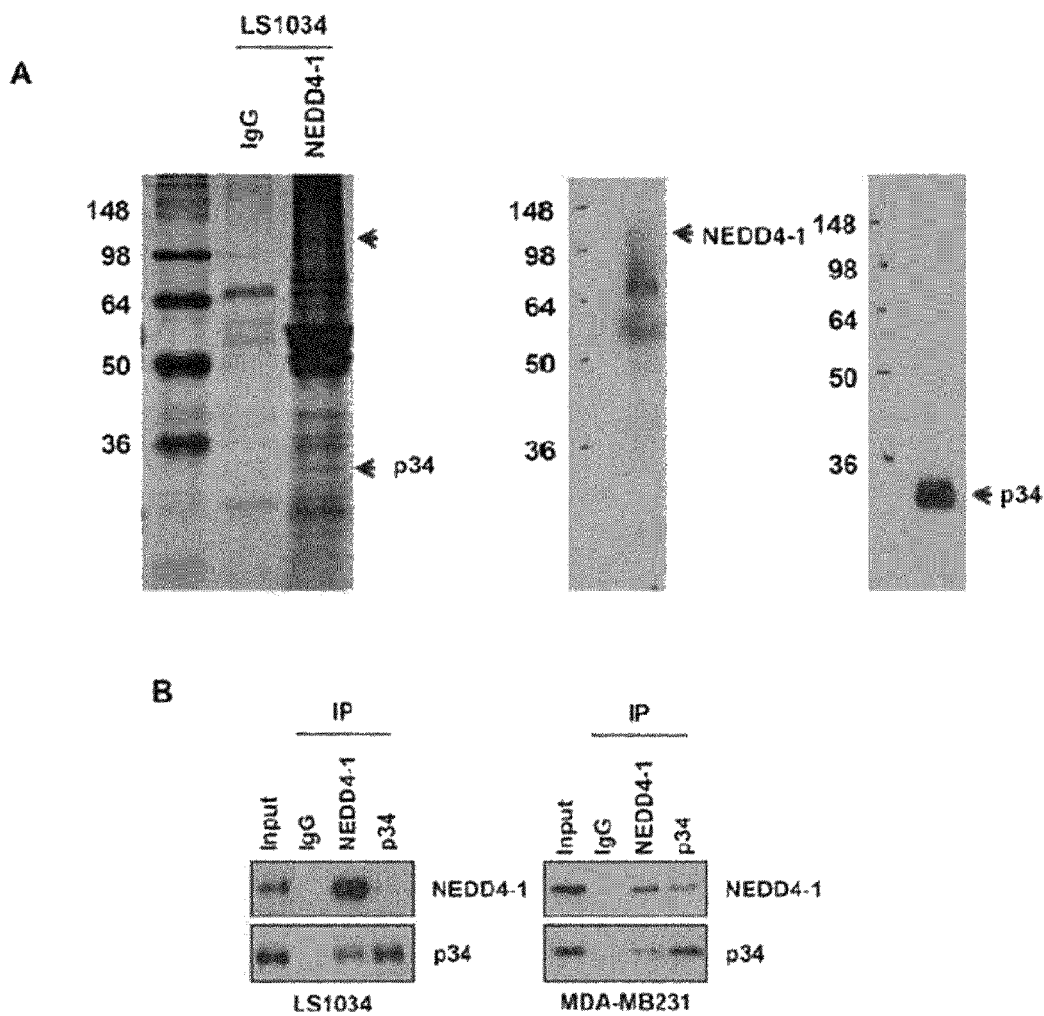

[Fig 5]
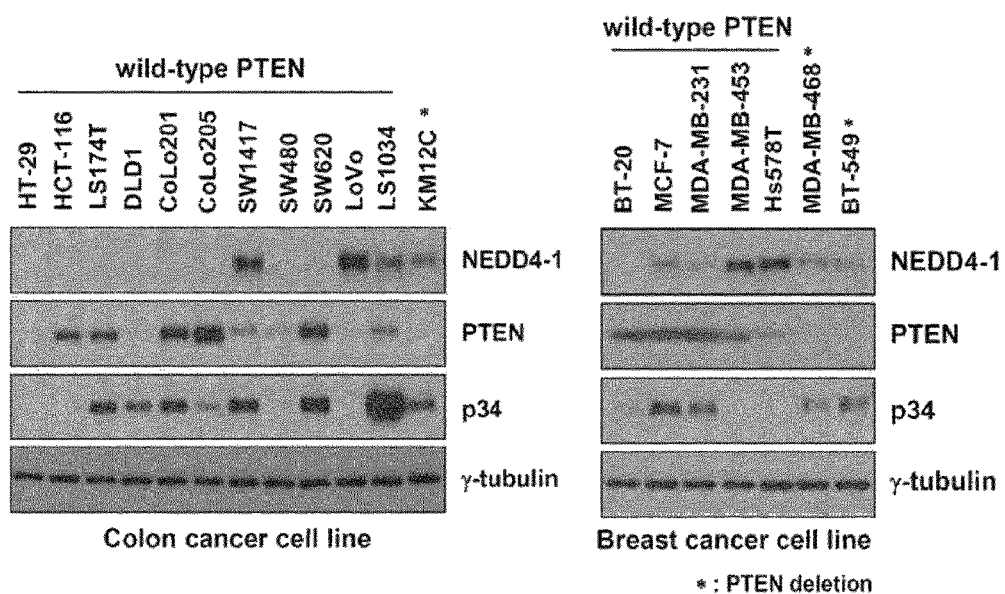

[Fig 6]
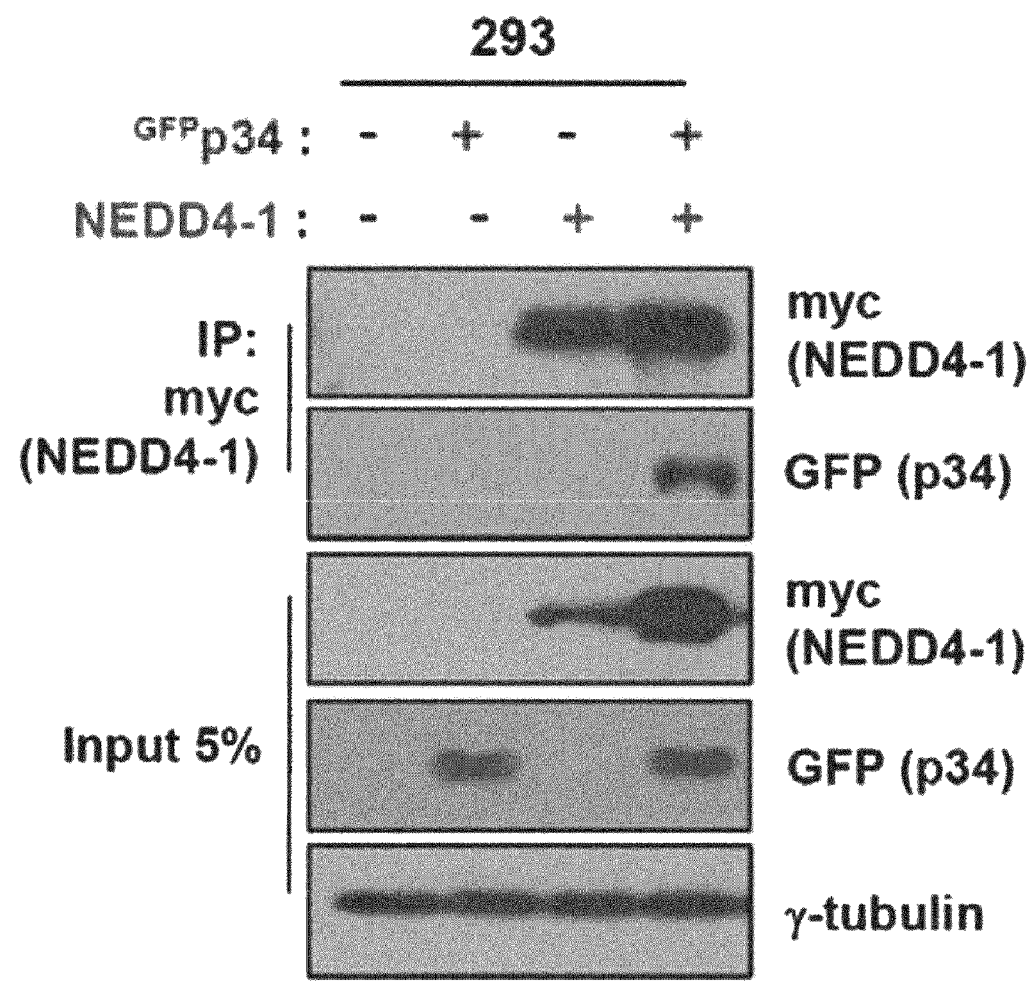

[Fig 7]
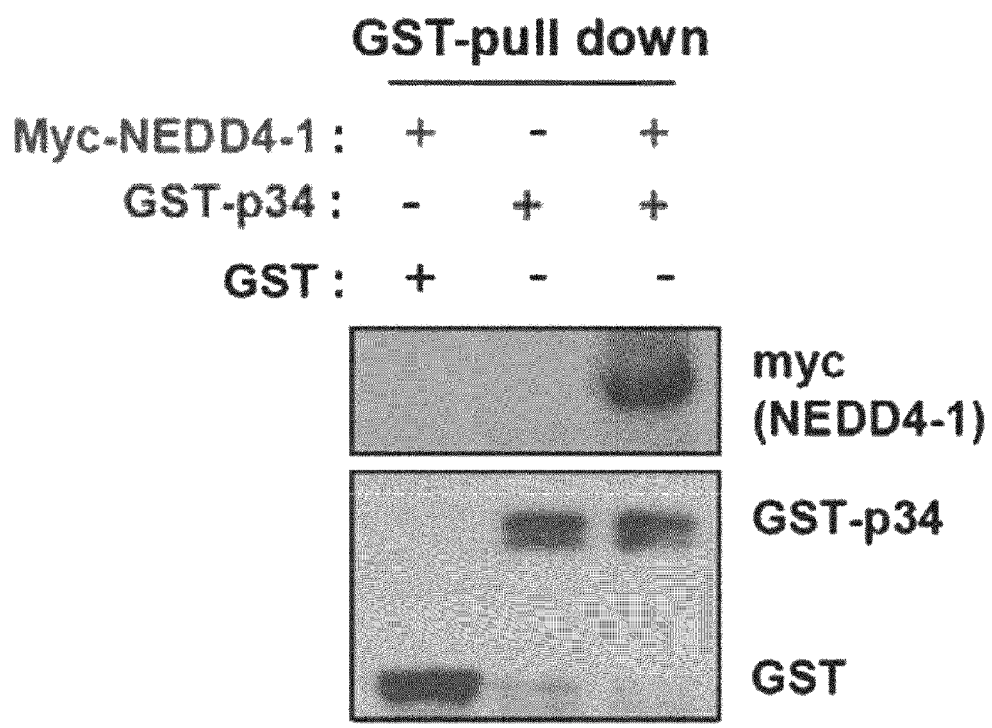

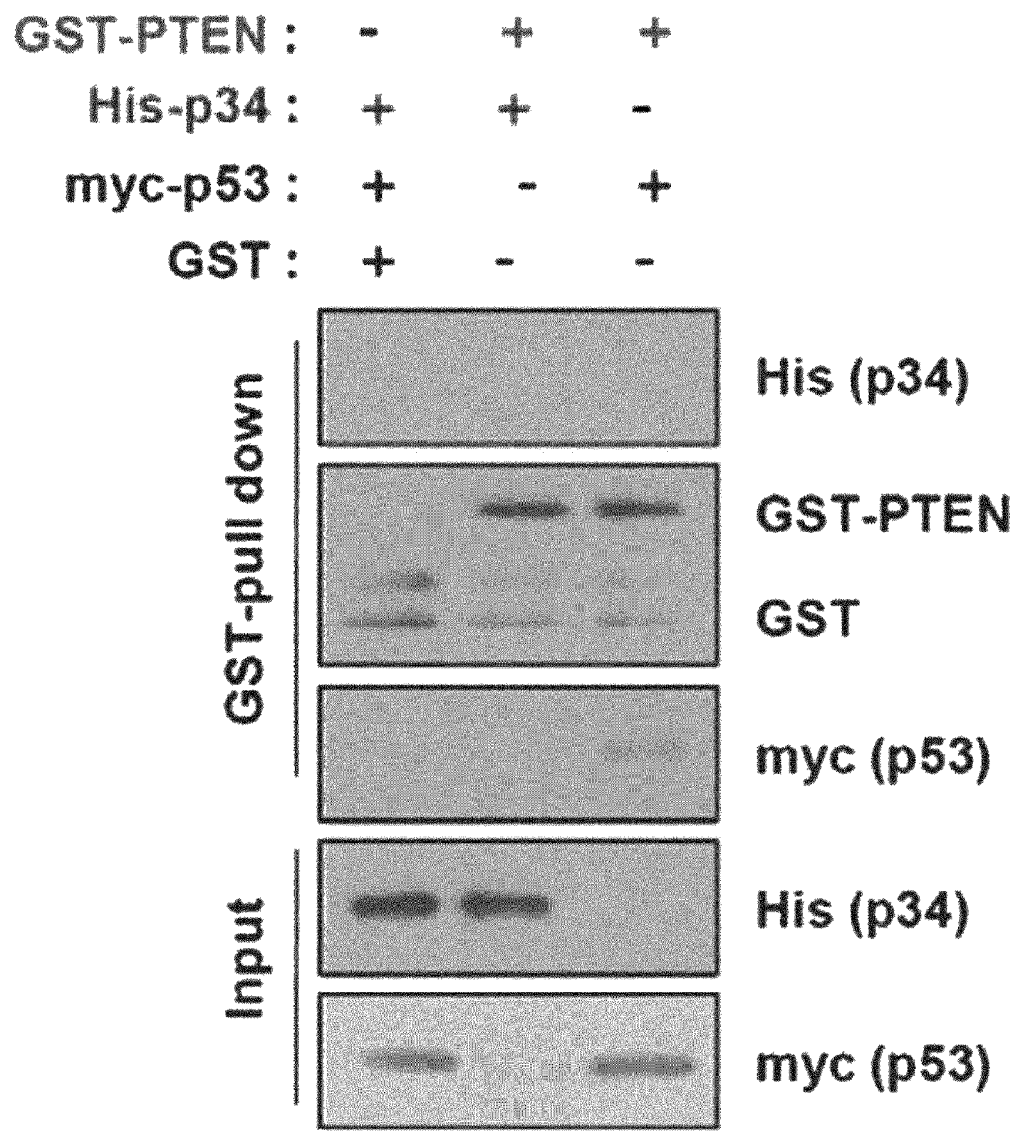
[Fig 8]

[Fig 9]
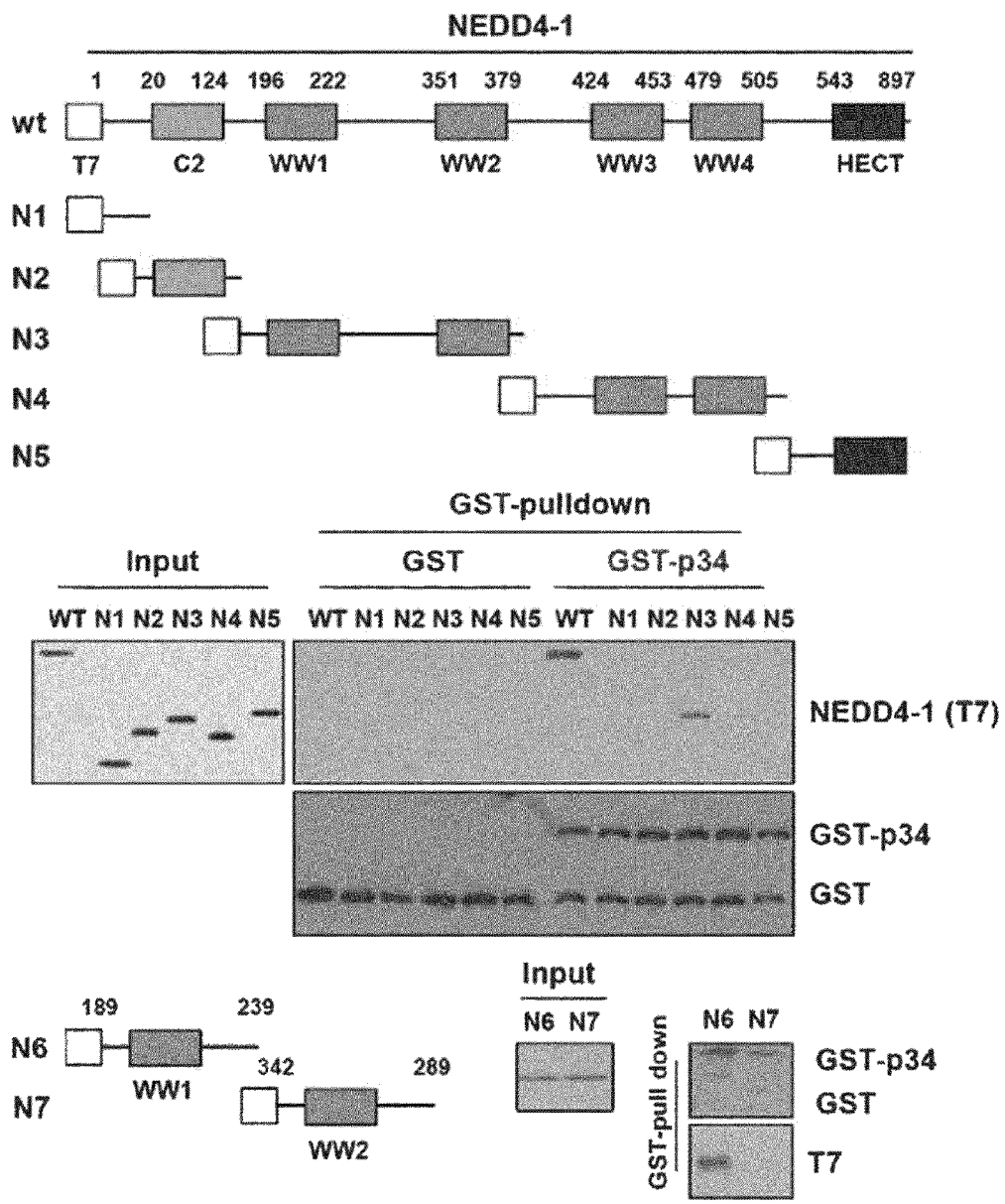

[Fig 10]
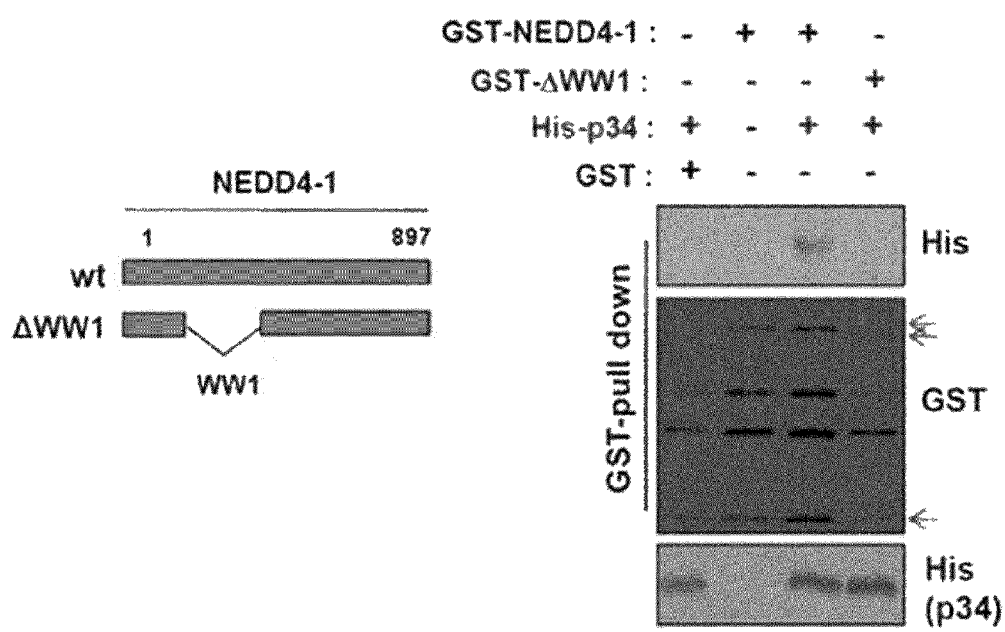

[Fig 11]
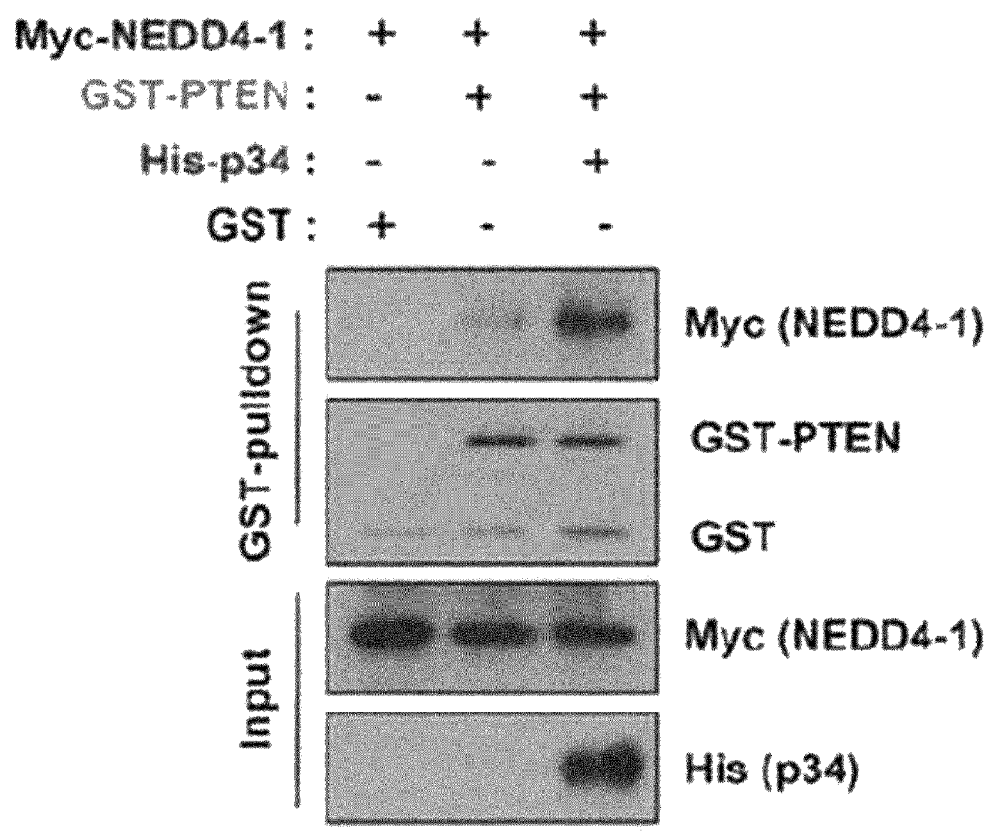

[Fig 12]
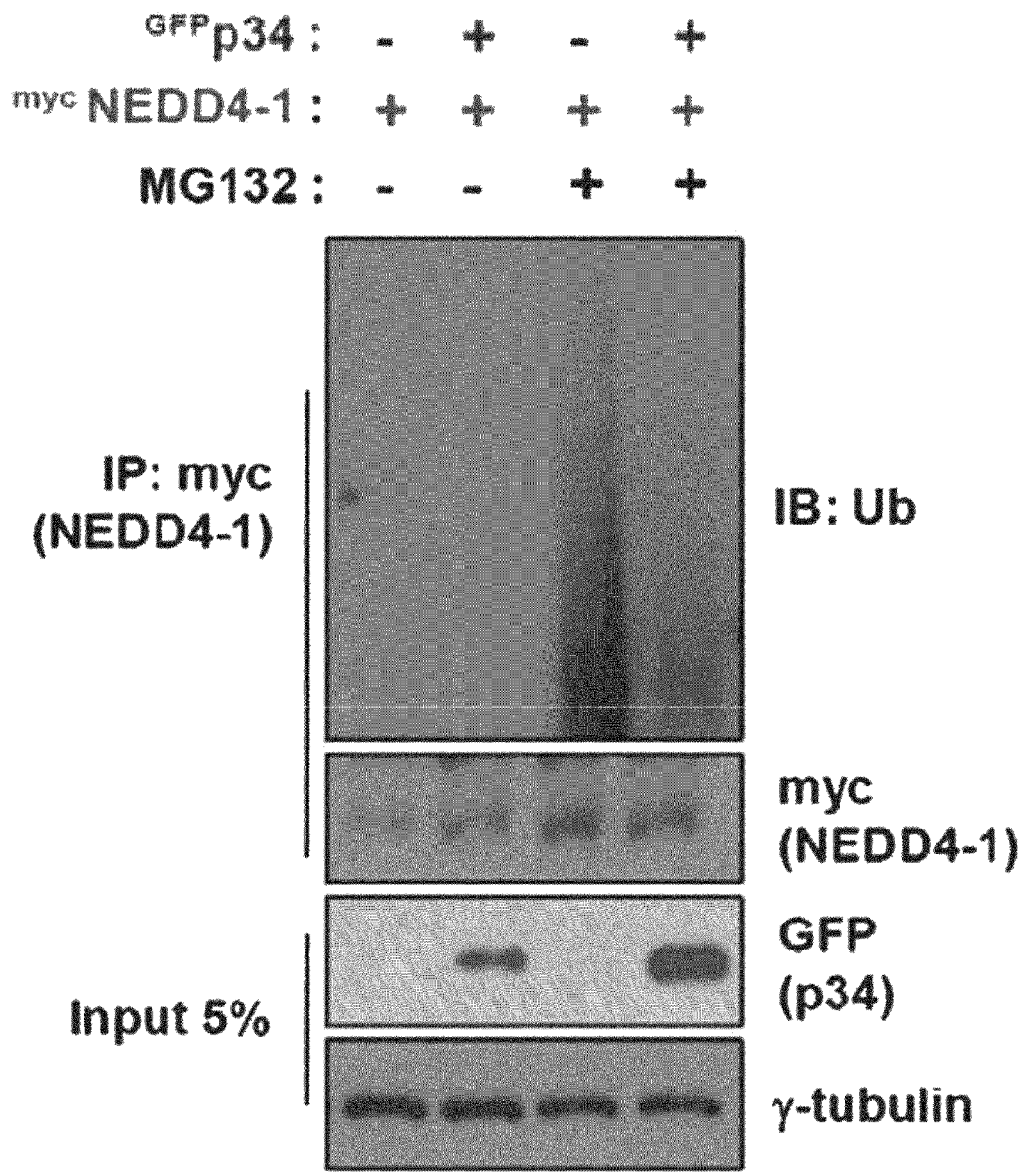

[Fig 13]
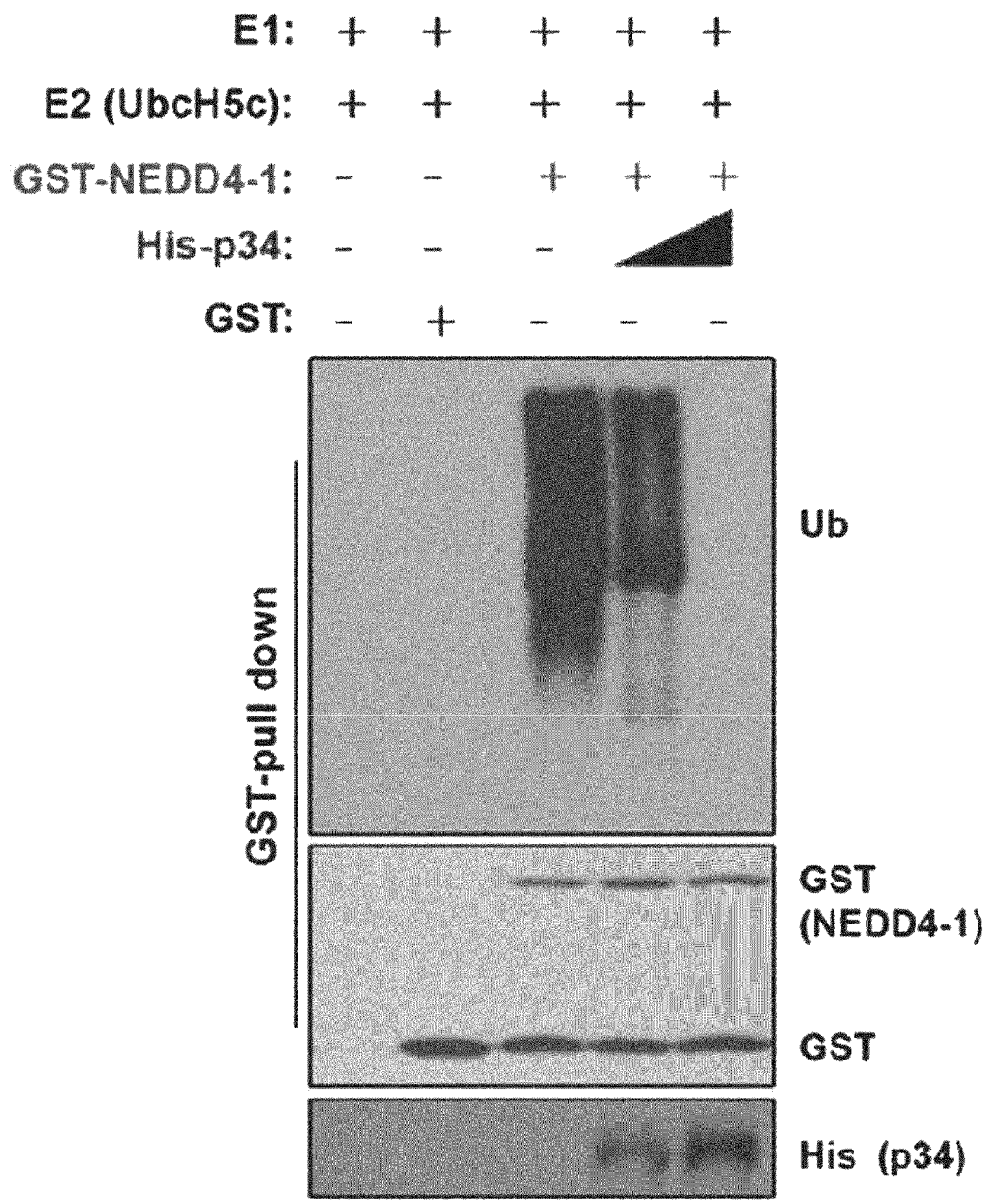

[Fig 14]
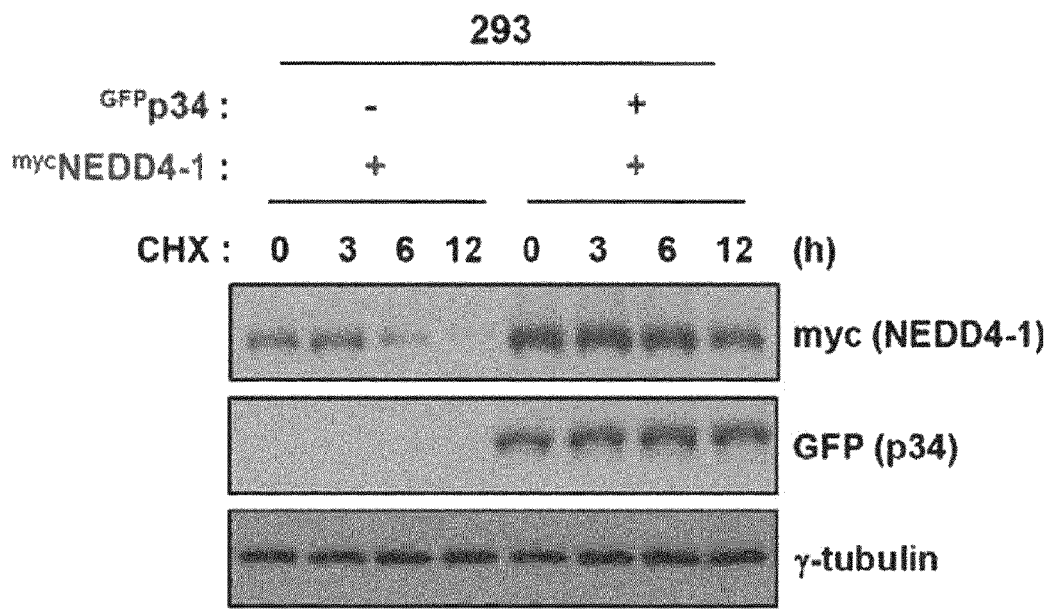
[Fig 15]
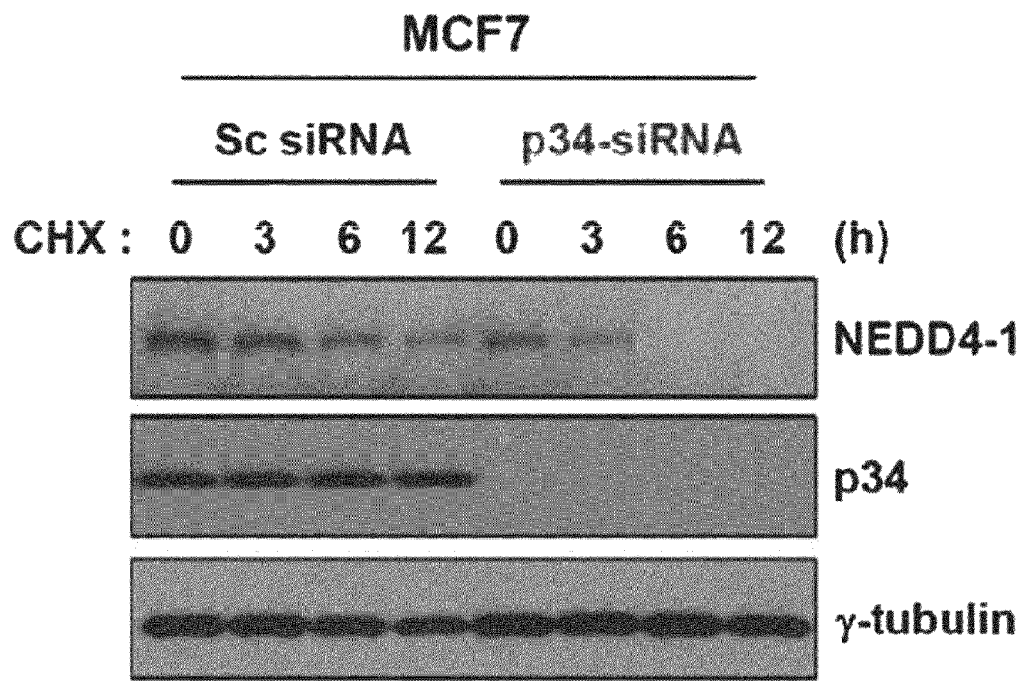

[Fig 16]
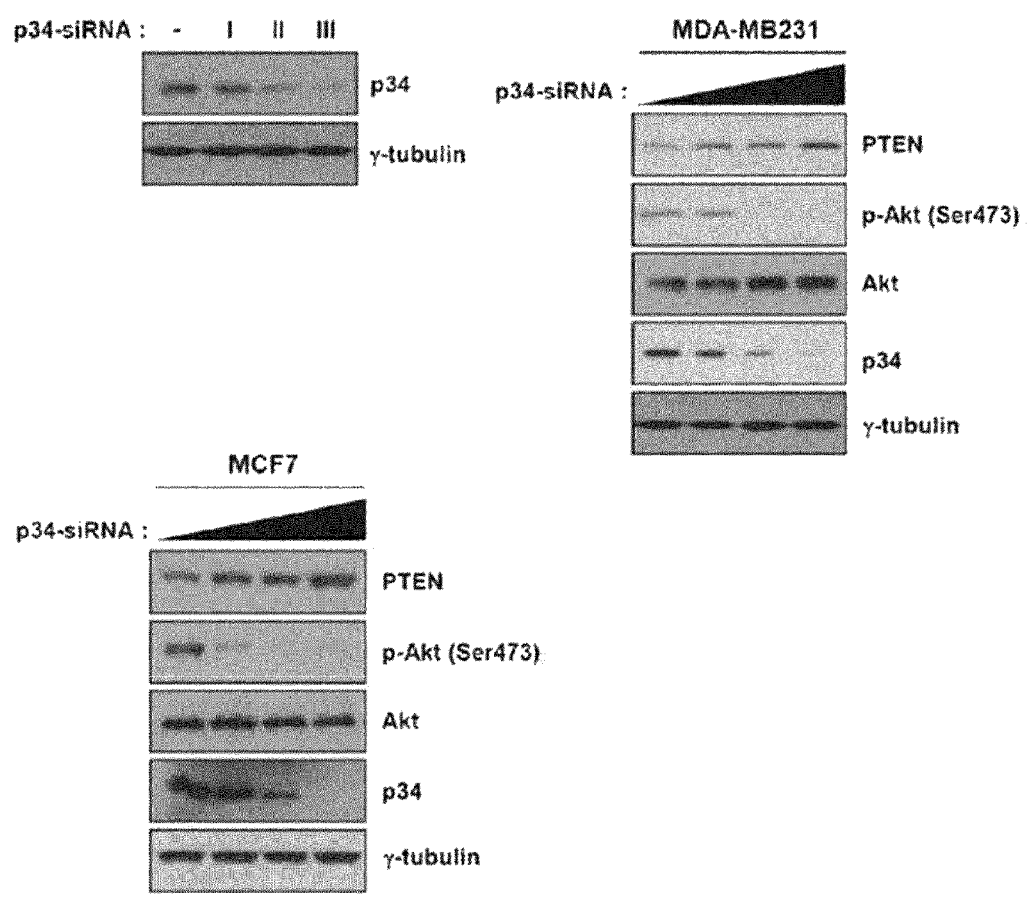

[Fig 17]
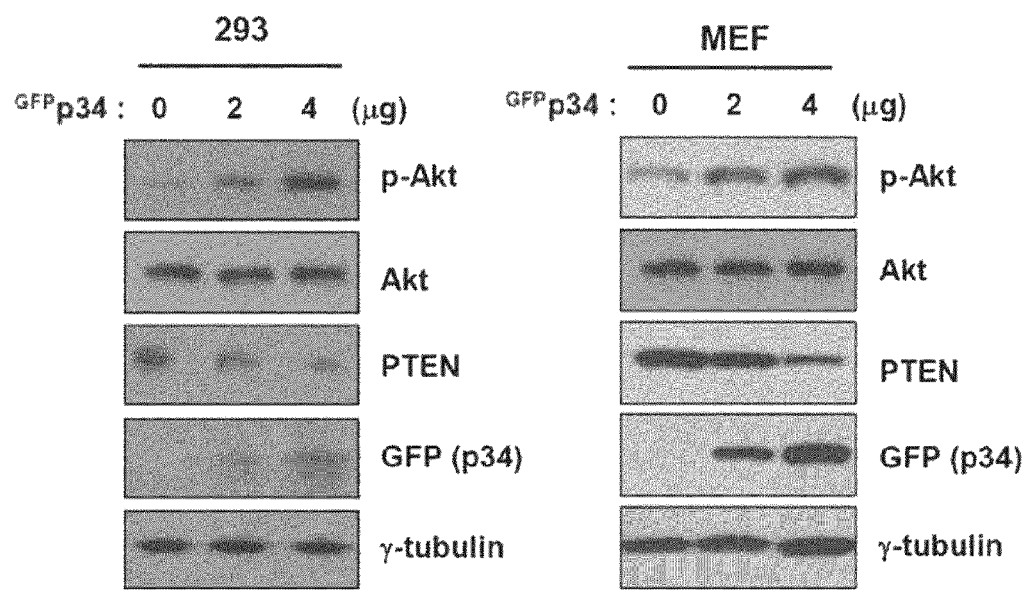
[Fig 18]
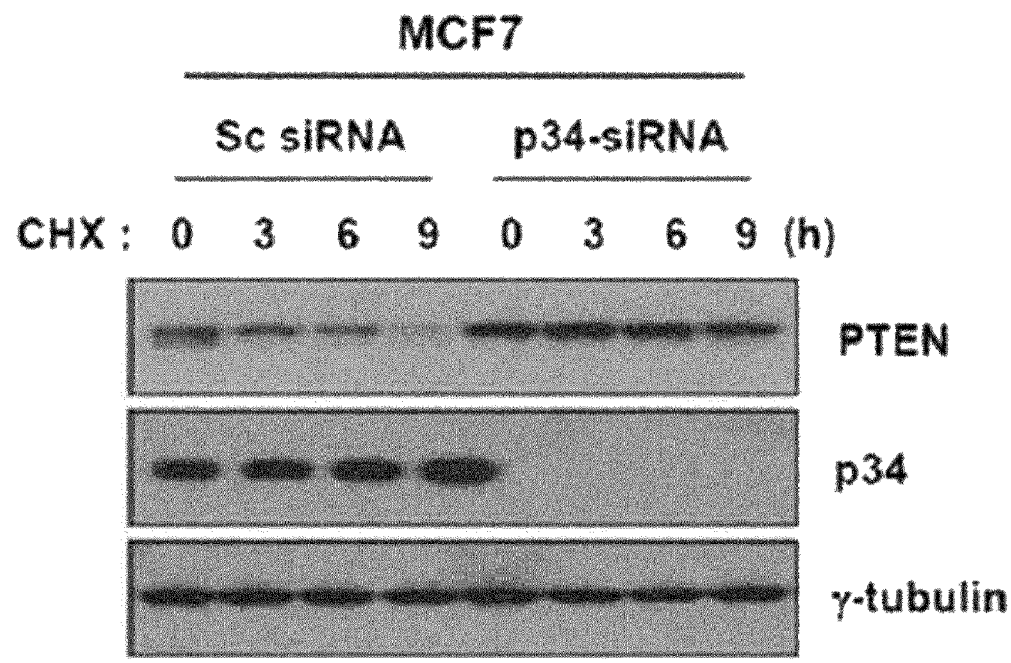

[Fig 19]
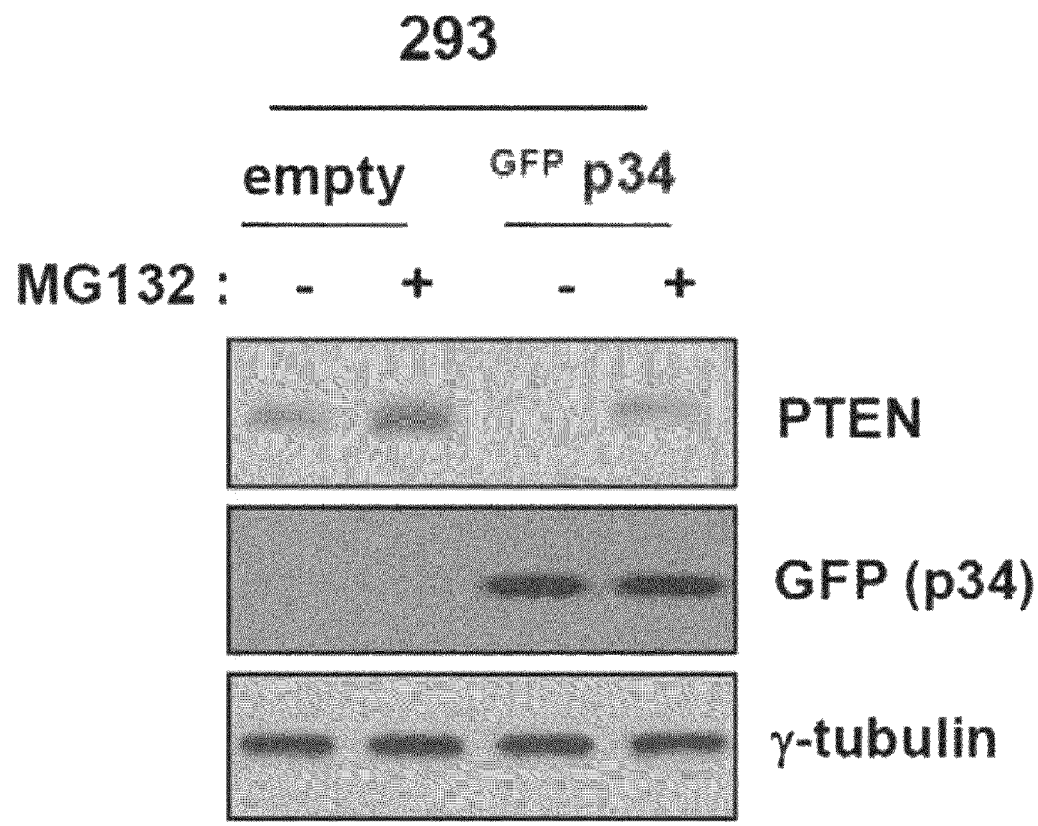

[Fig 20]
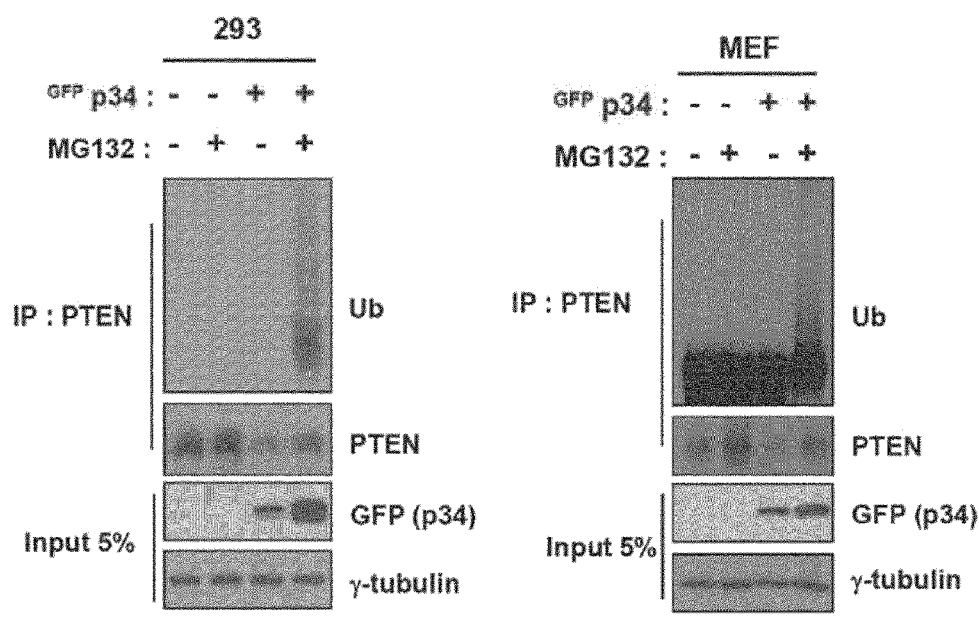
[Fig 21]
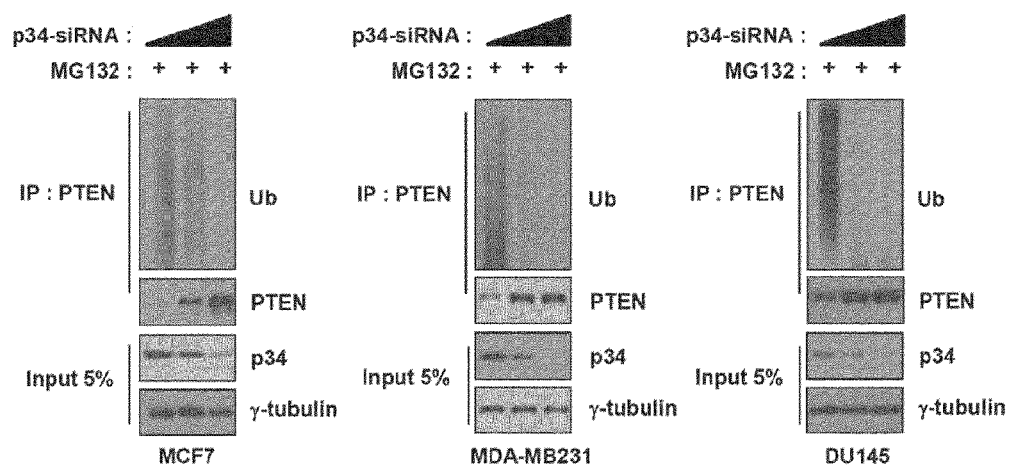

[Fig 22]
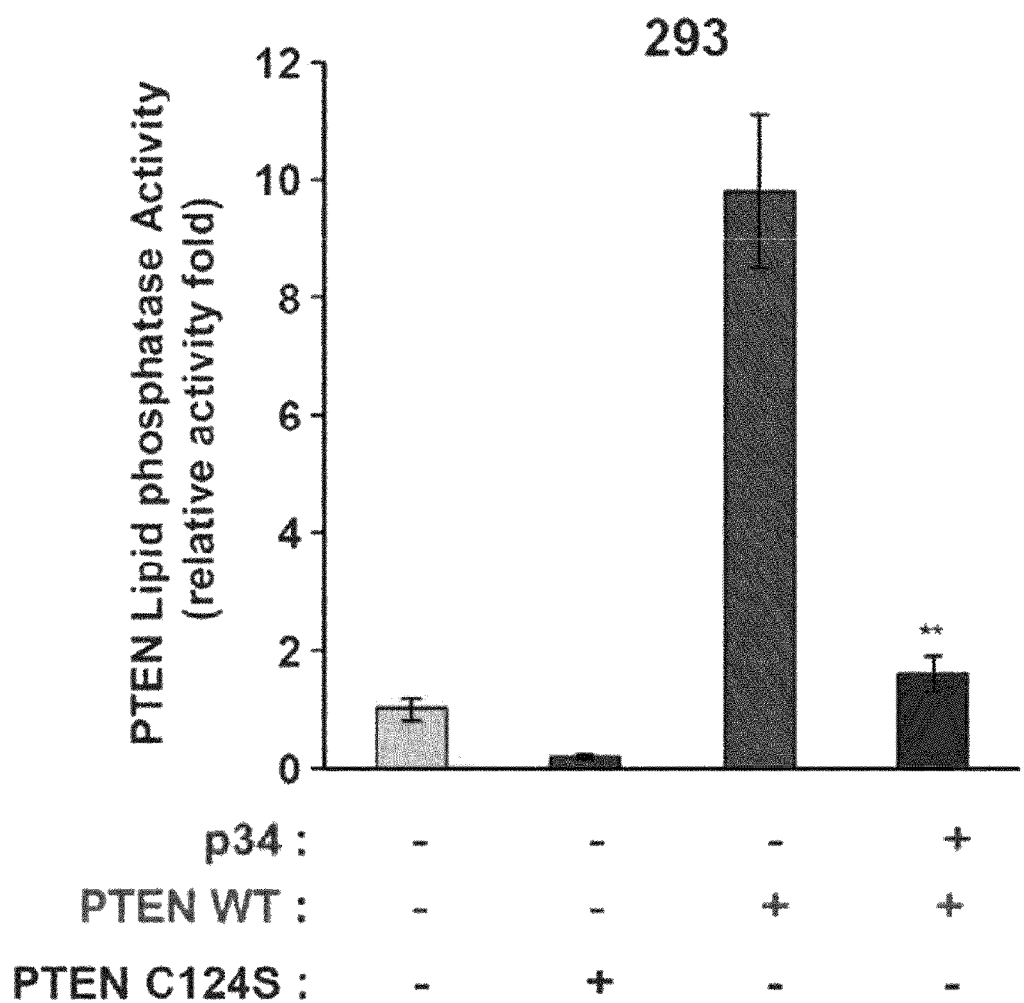

[Fig 23]
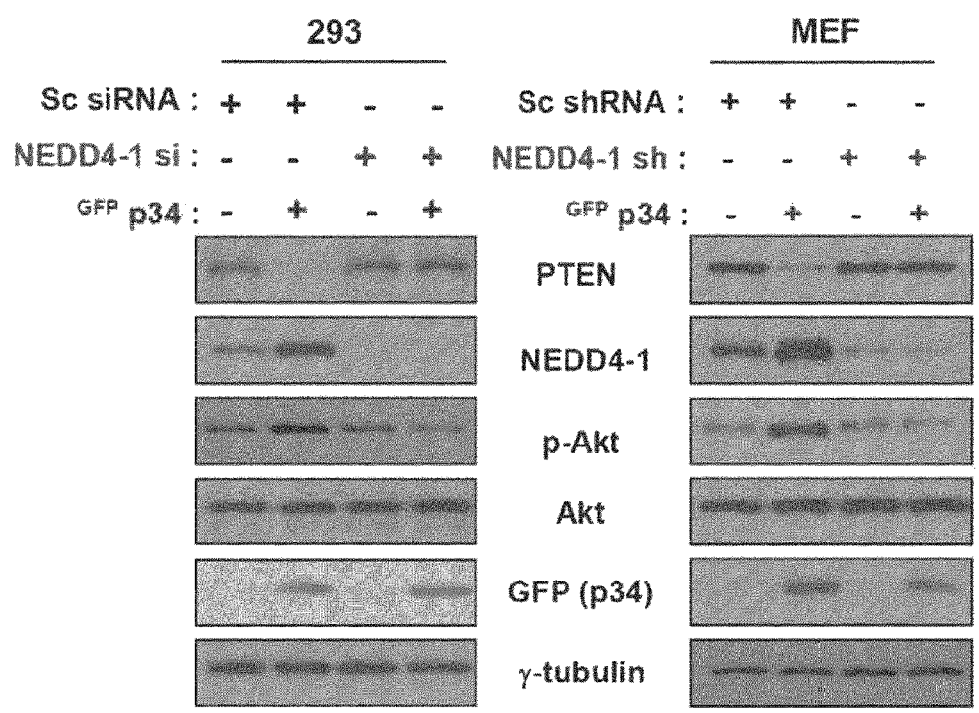

[Fig 24]
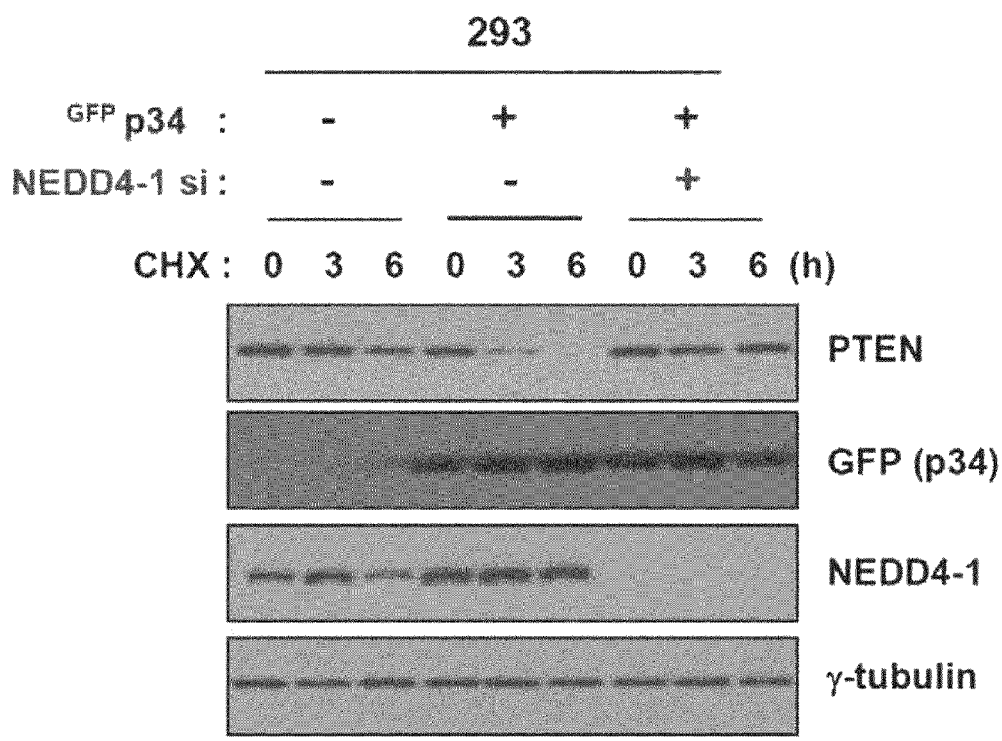

[Fig 25]
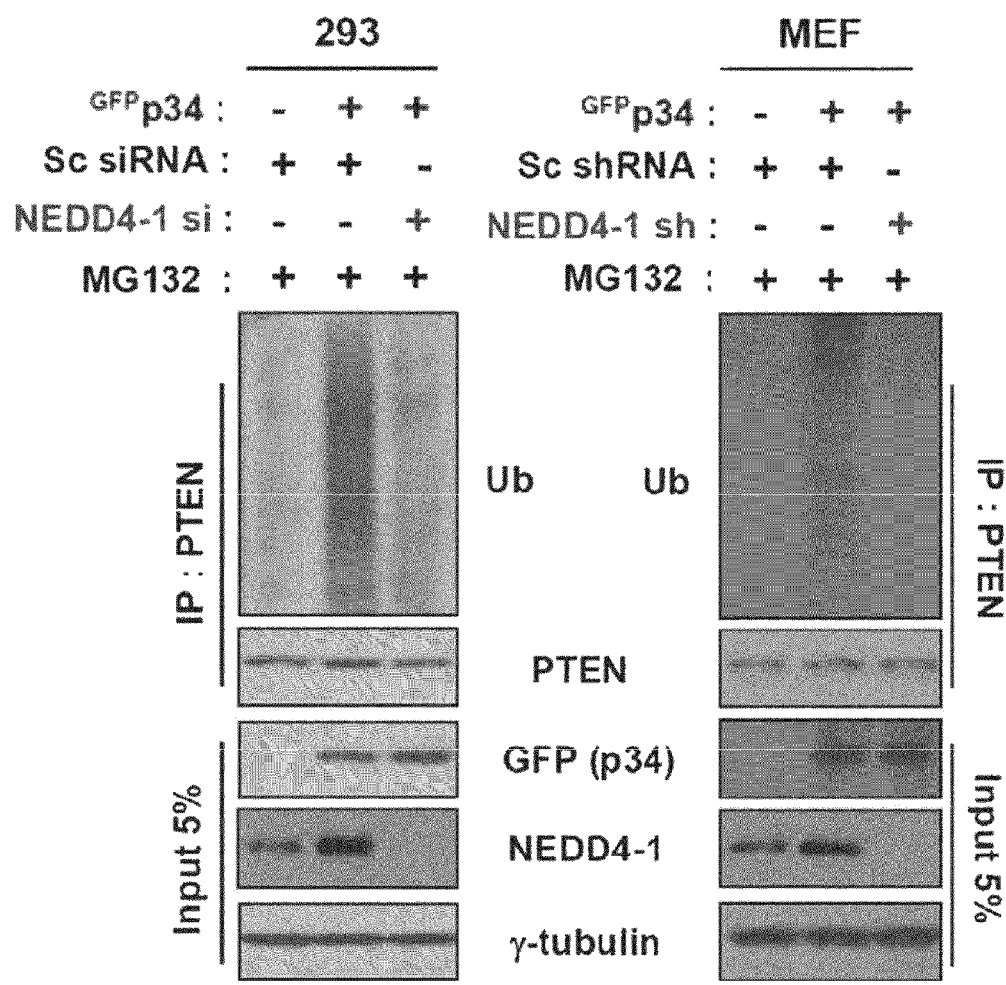

[Fig 26]
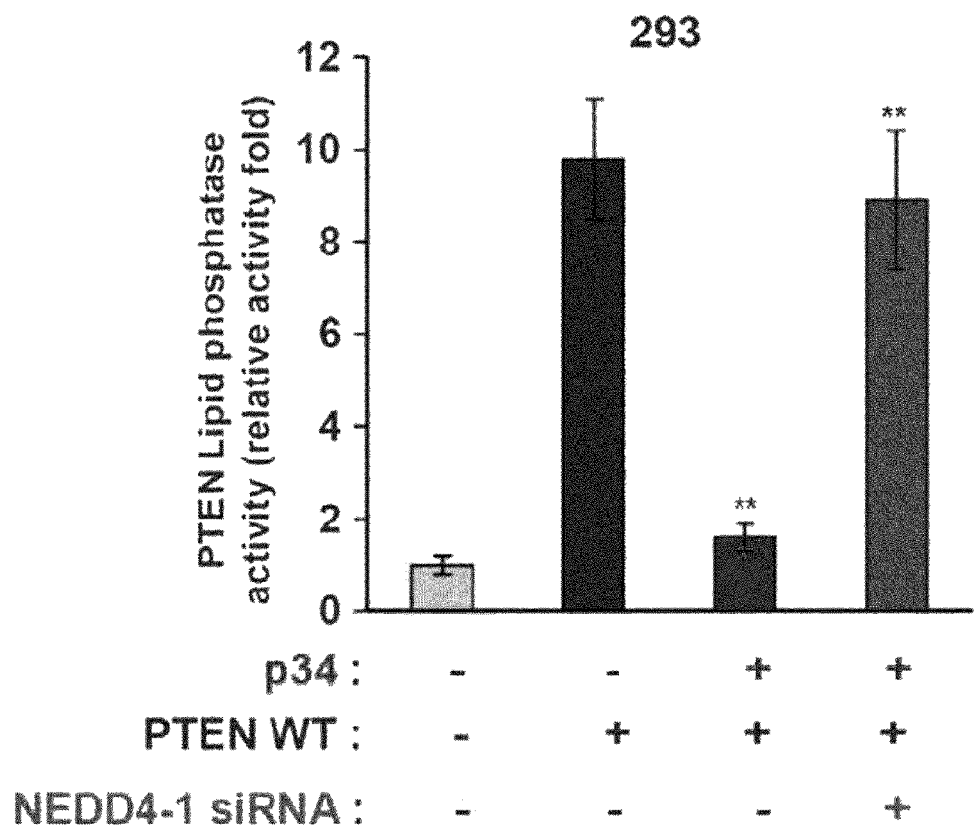

[Fig 27]
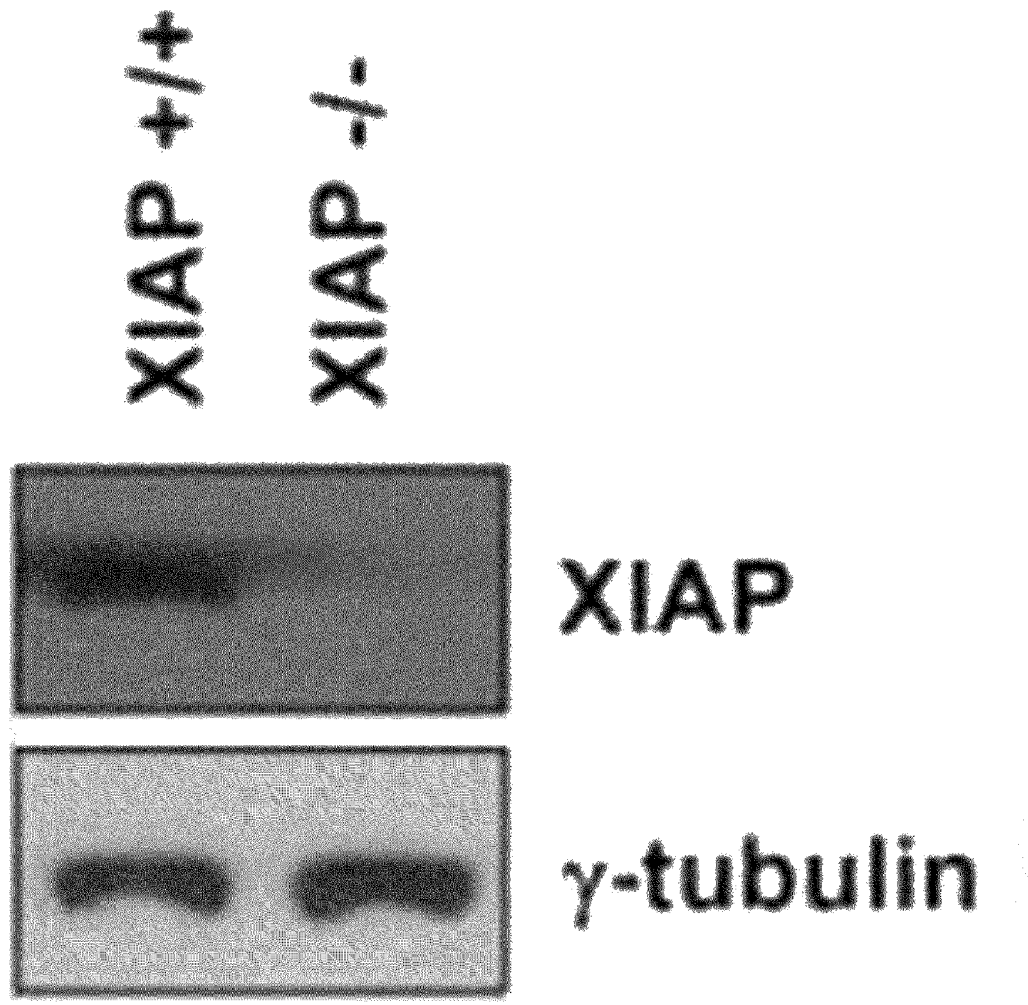

[Fig 28]
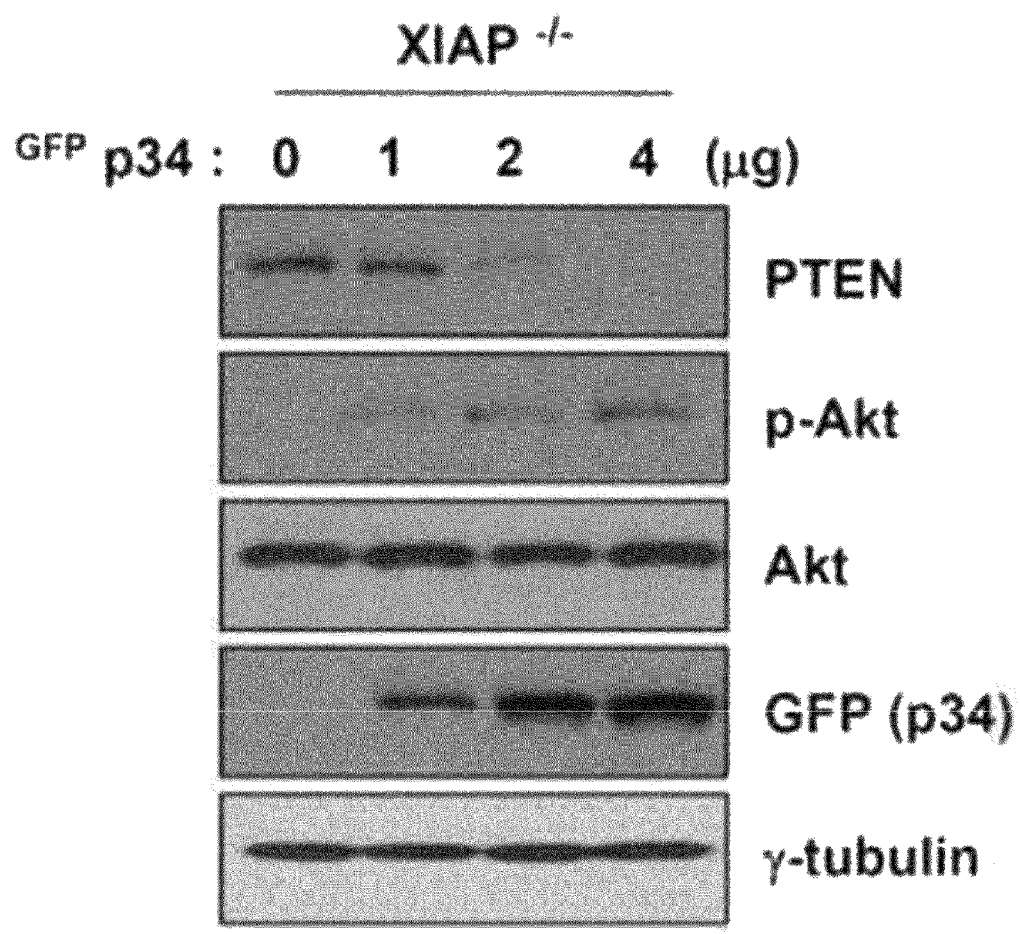

[Fig 29]
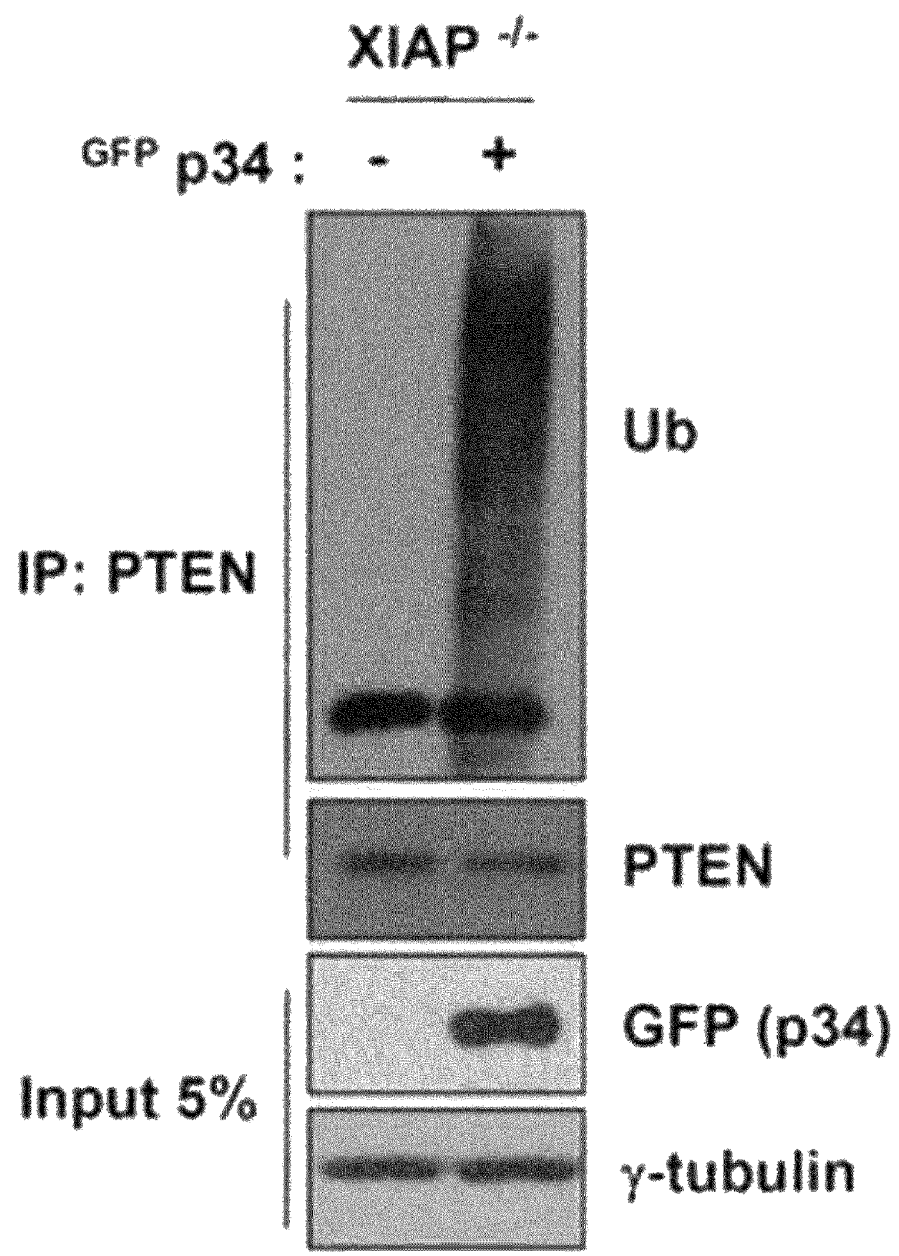

[Fig 30]
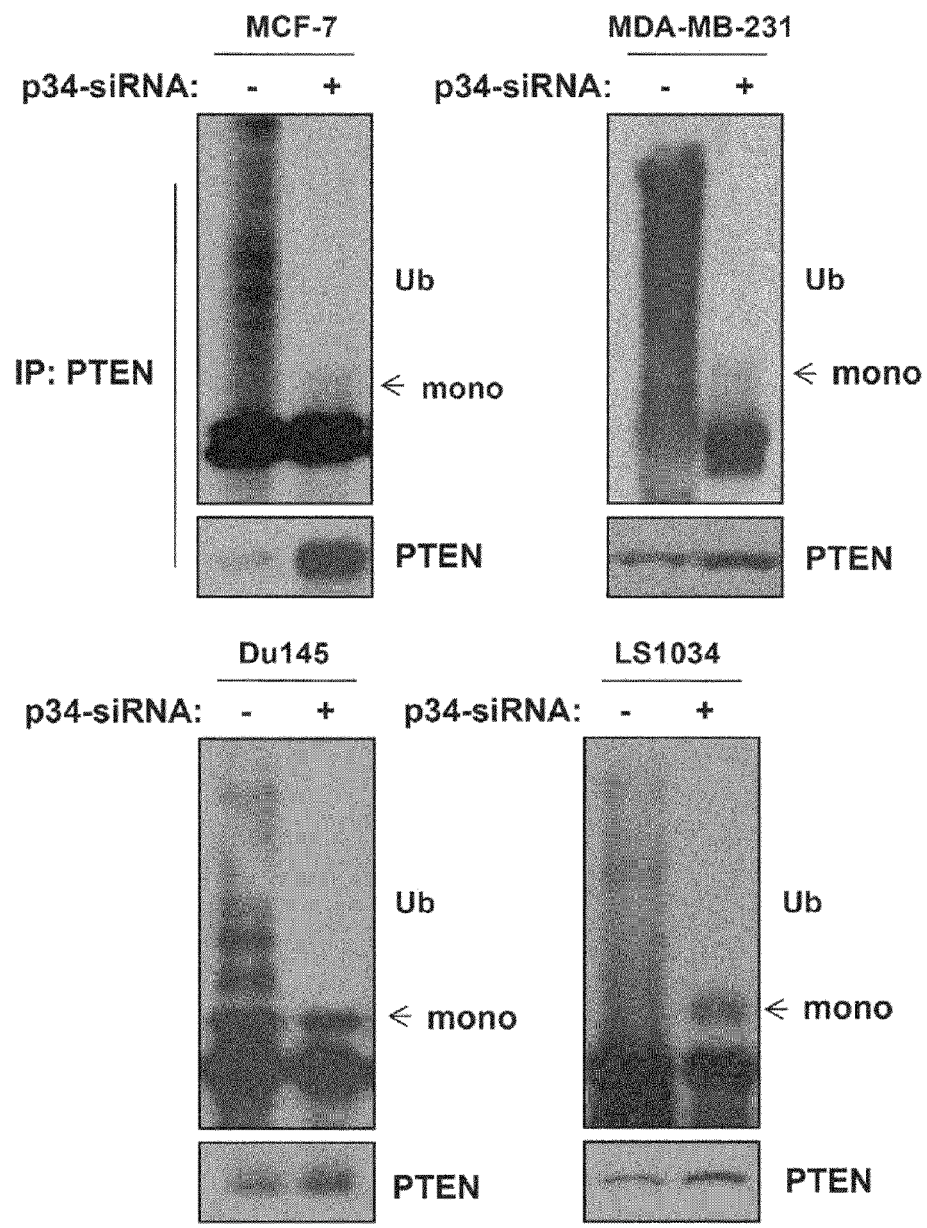

[Fig 31]
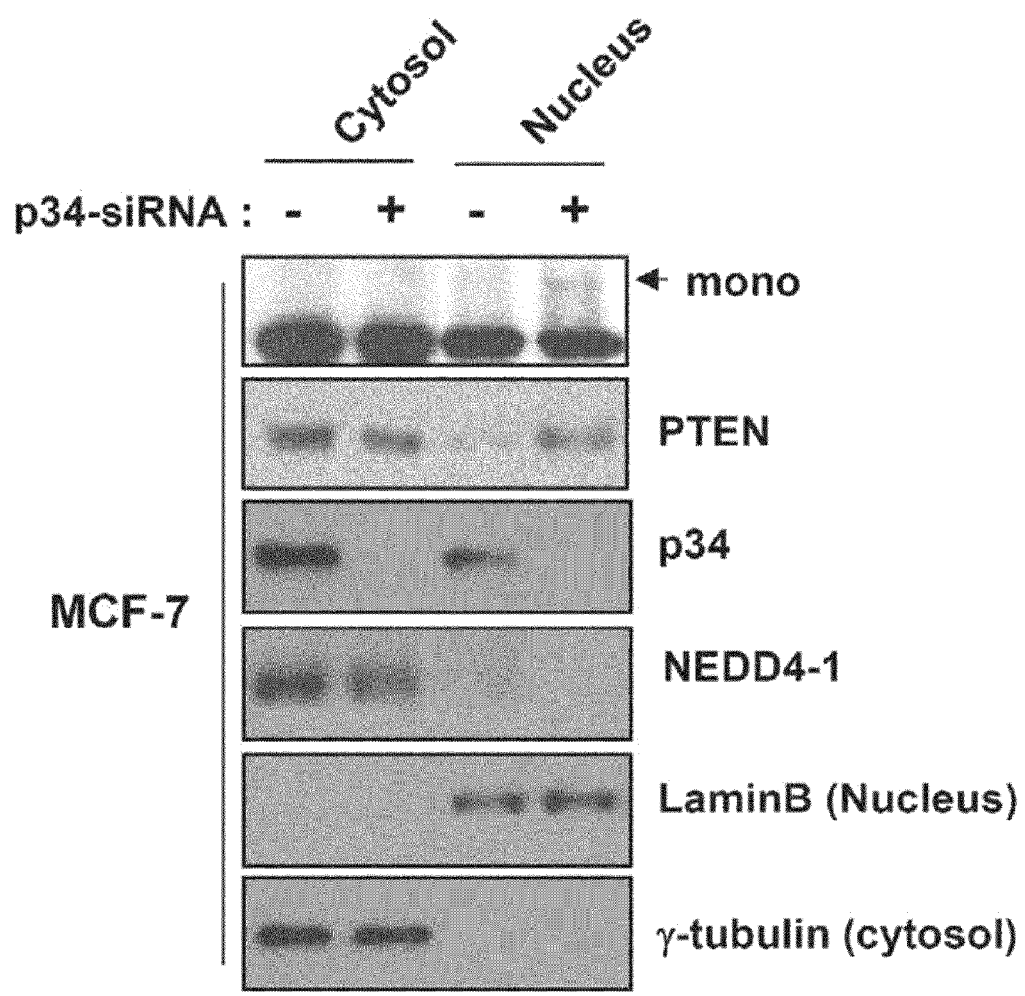

[Fig 32]
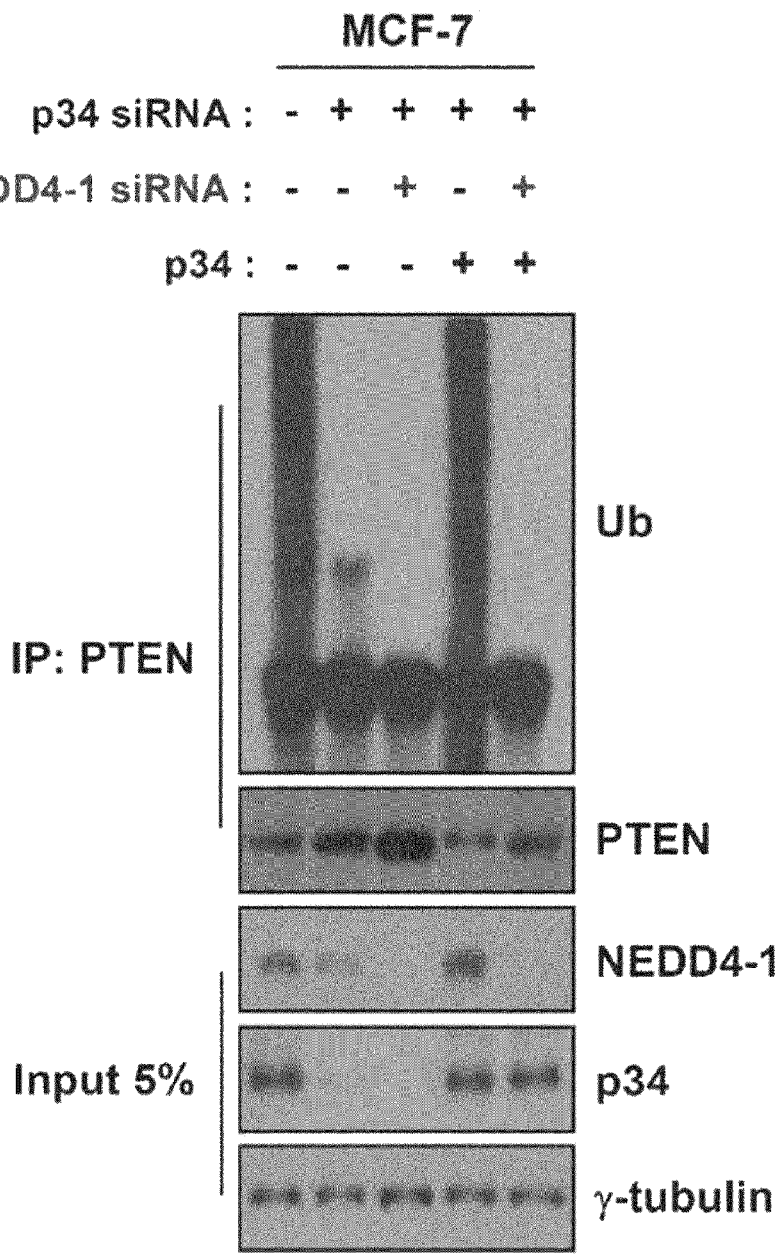

[Fig 33]
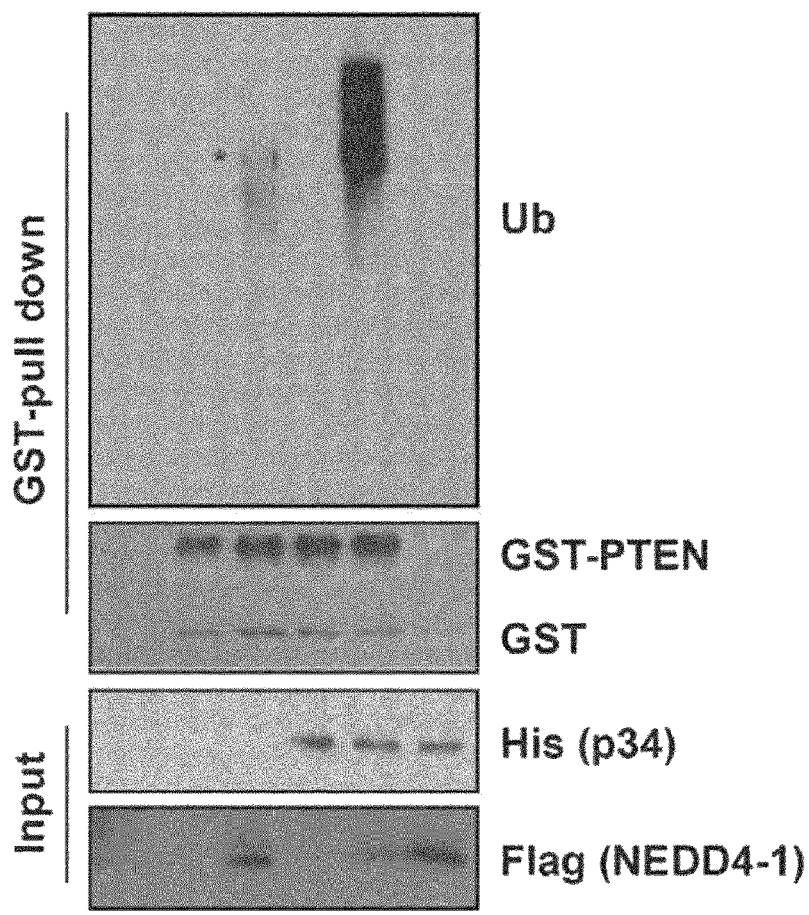

[Fig 34]
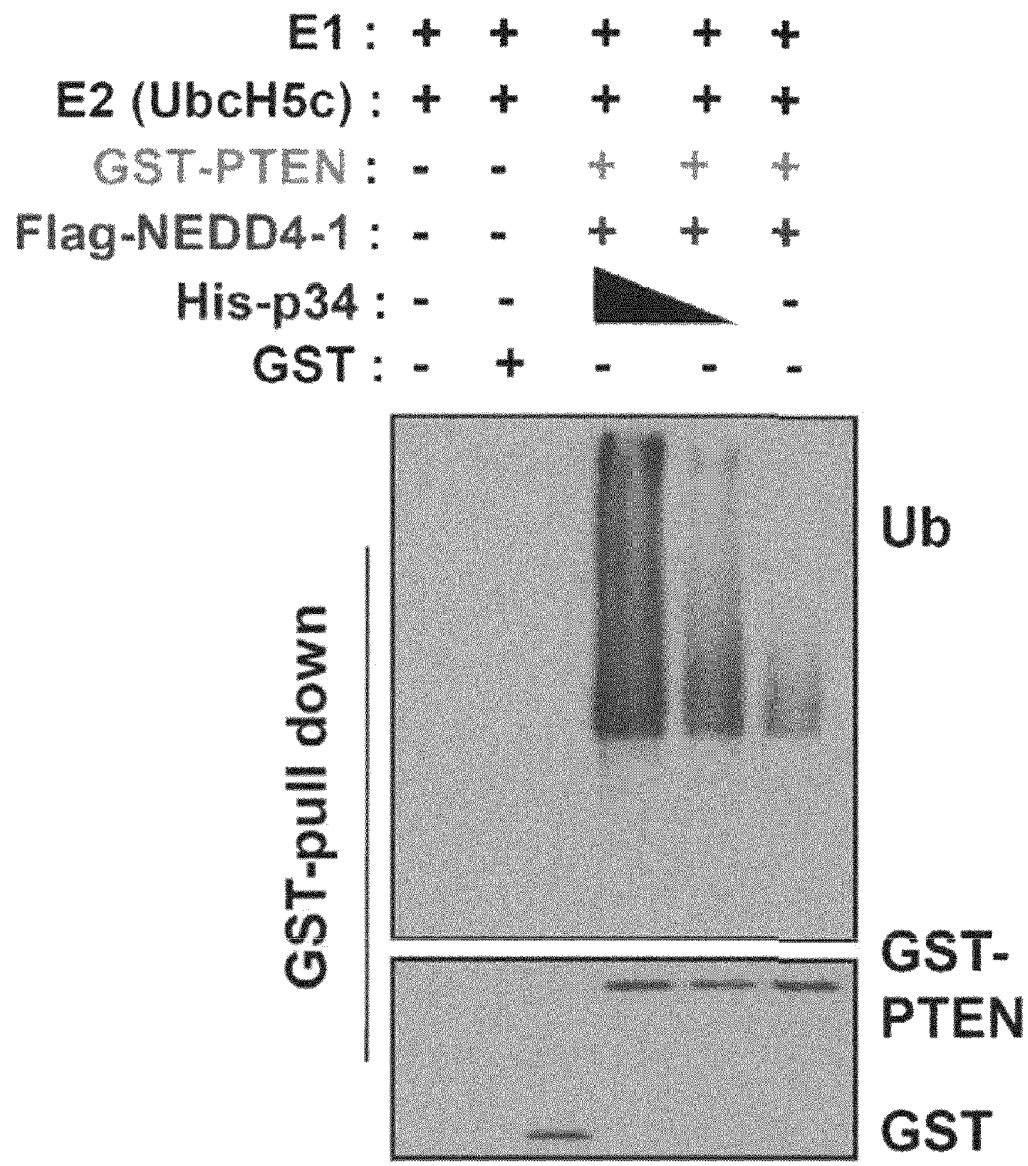

[Fig 35]
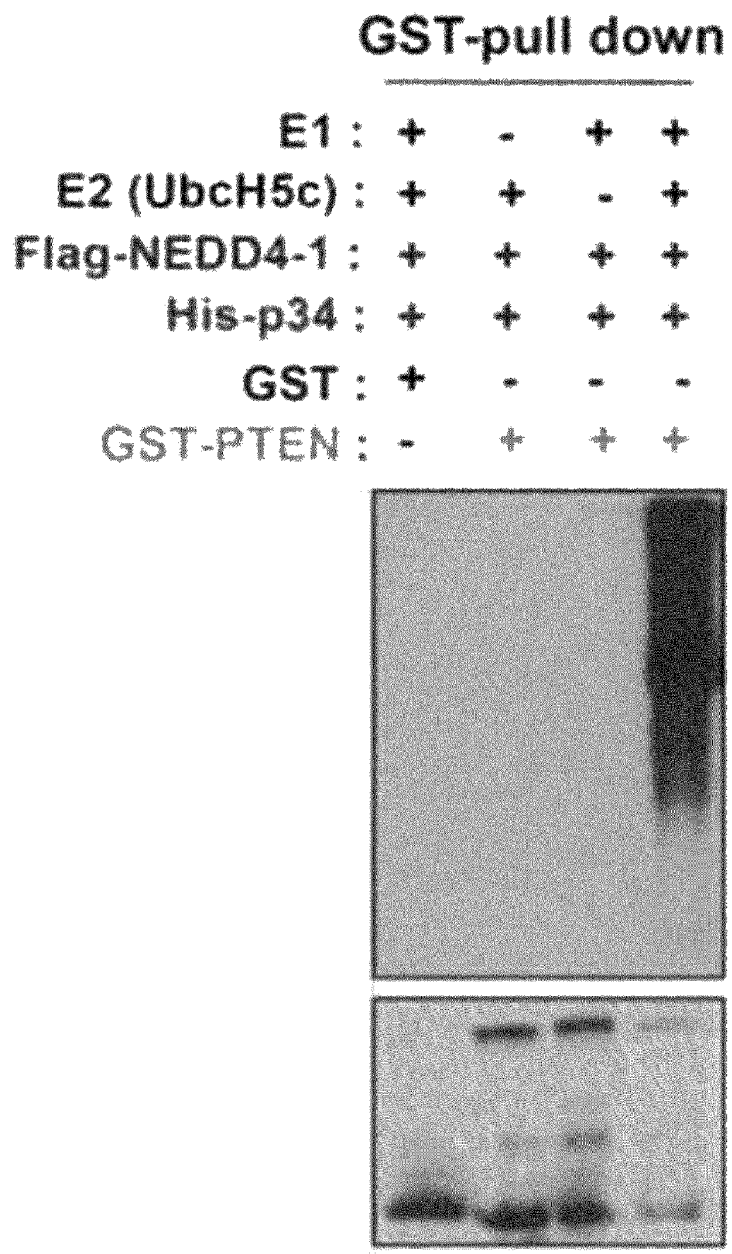

【Fig 36】
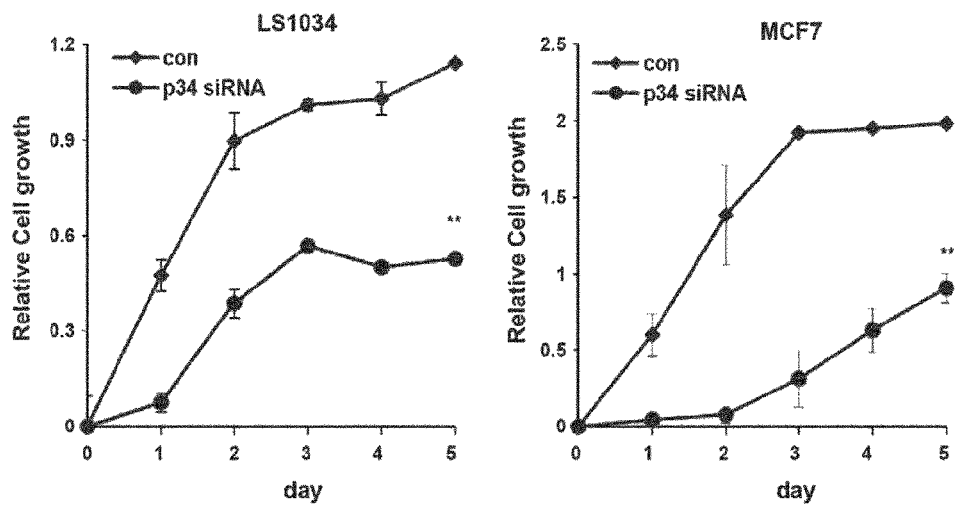
【Fig 37】
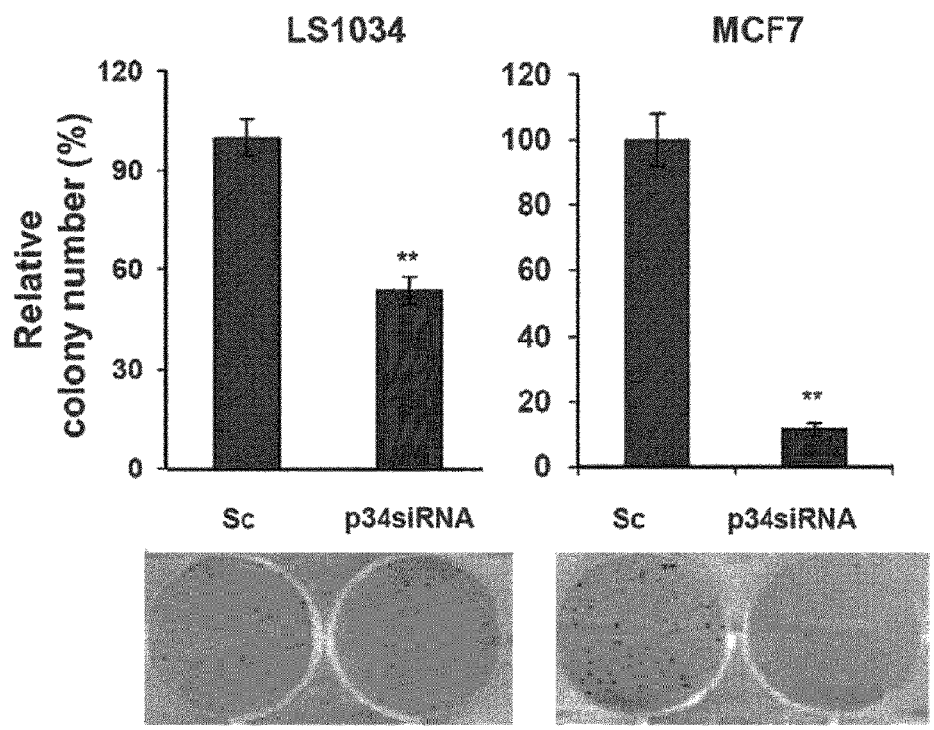

[Fig 38]
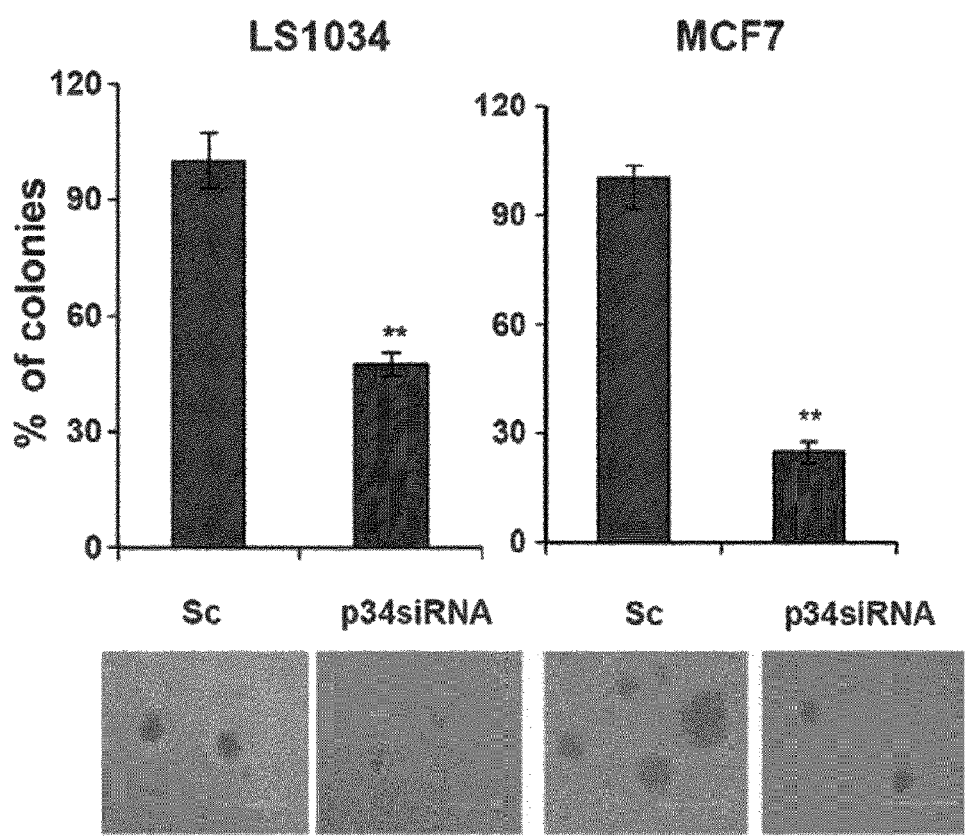

[Fig 39]
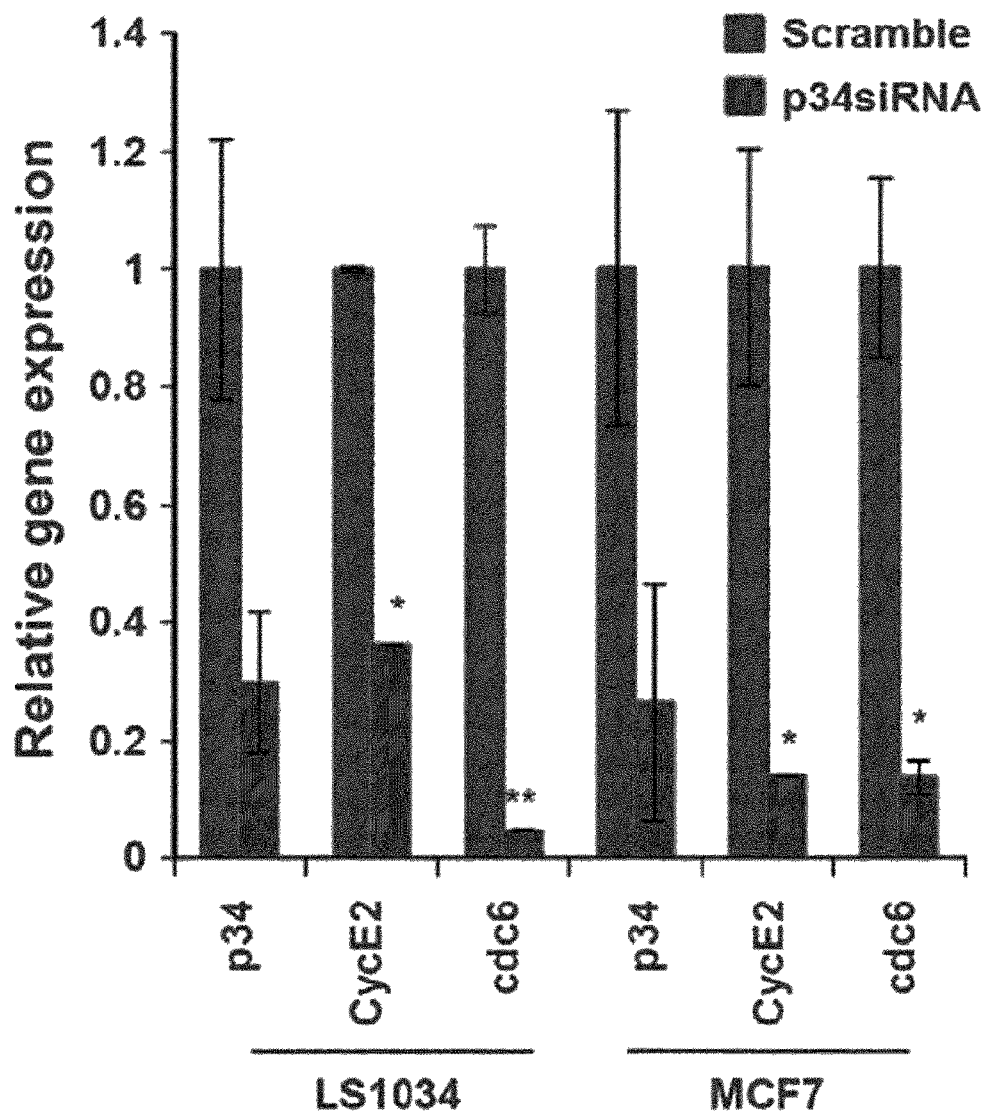

[Fig 40]
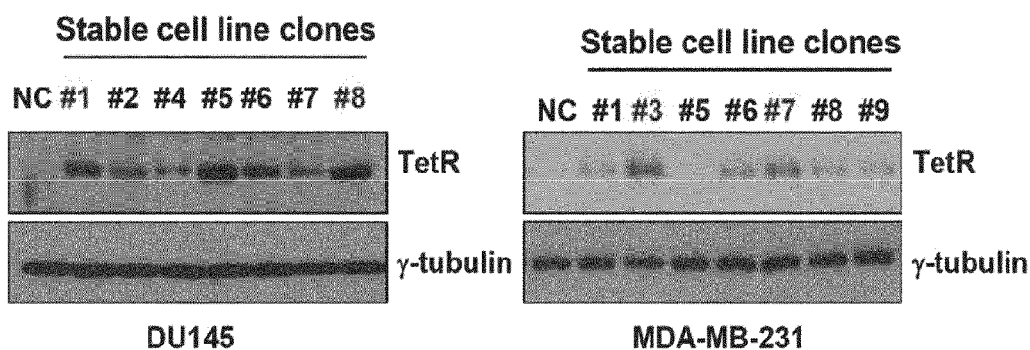
[Fig 41]
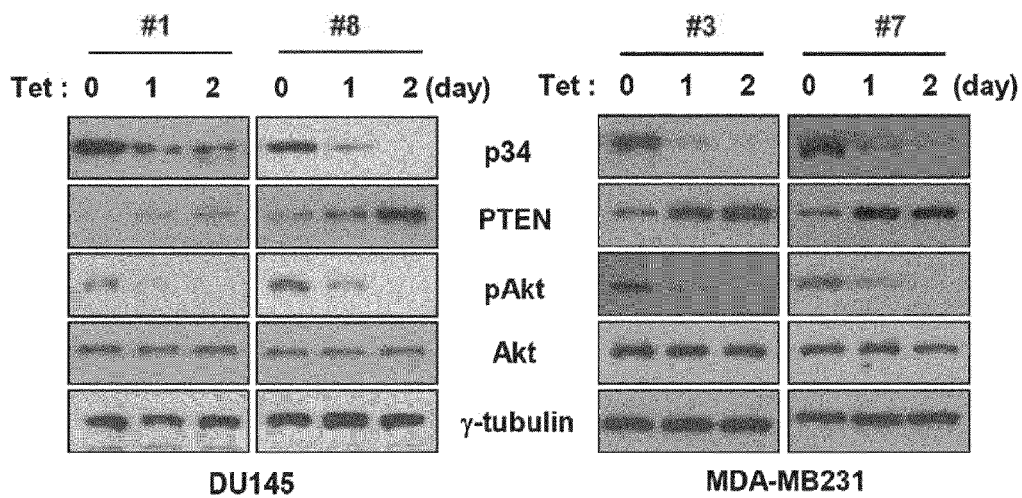

[Fig 42]
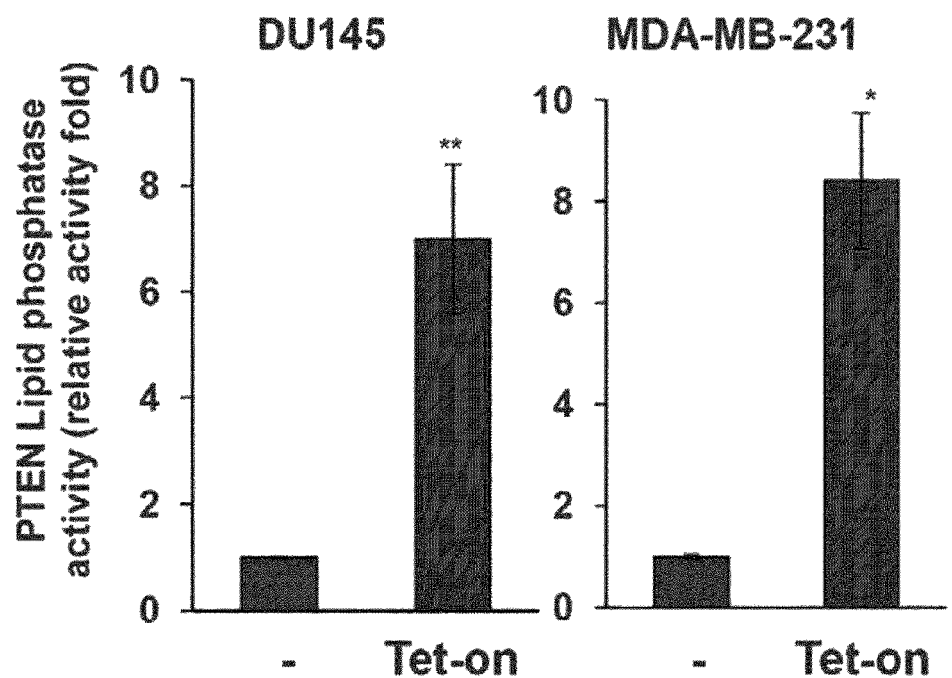
[Fig 43]
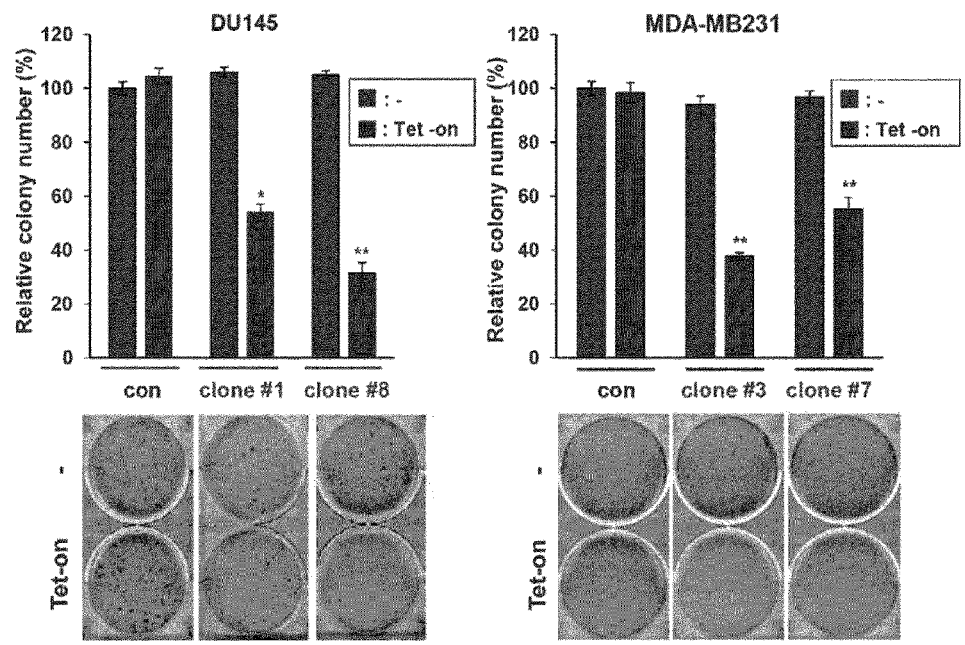

【Fig 44】
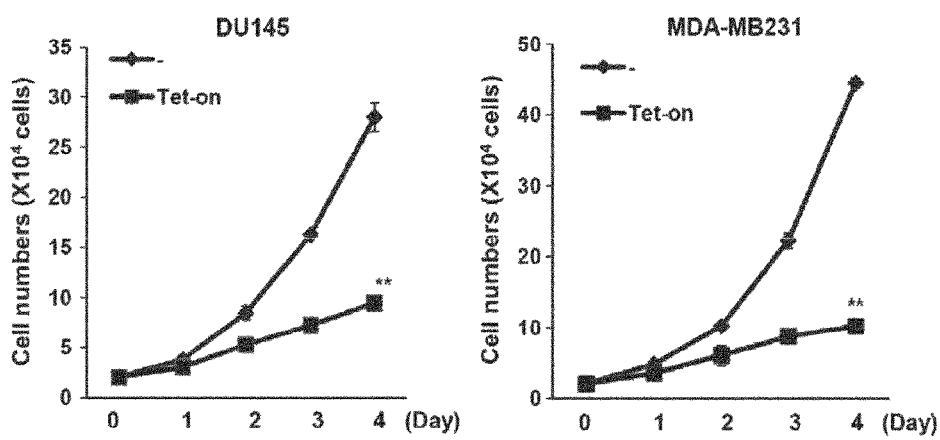
【Fig 45】
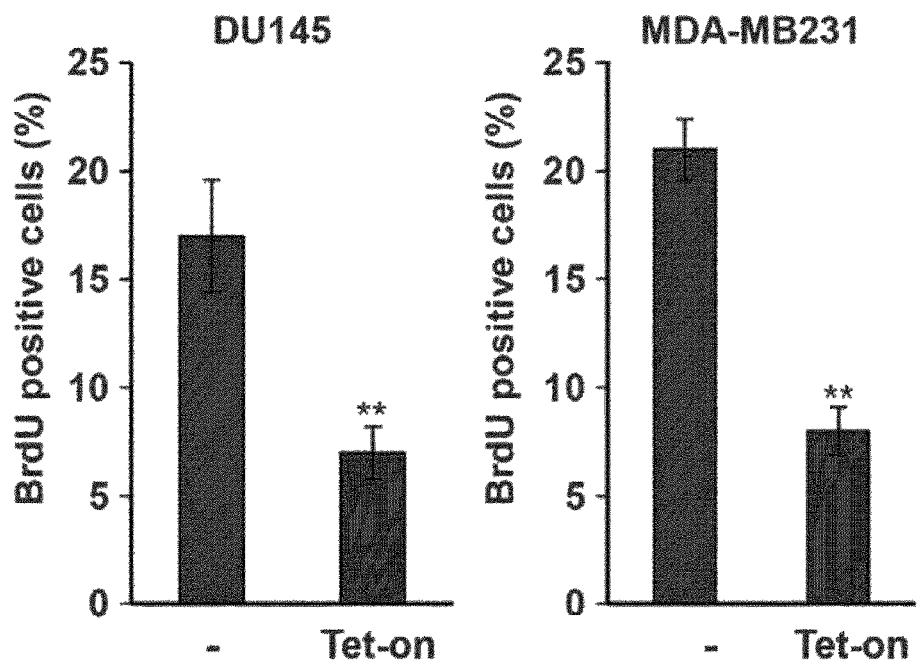

[Fig 46]
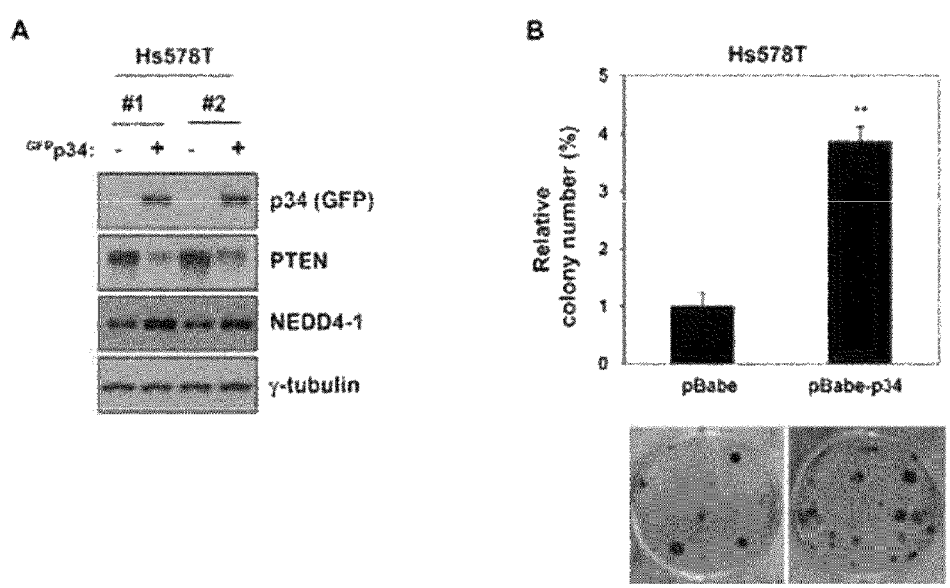

[Fig 47]
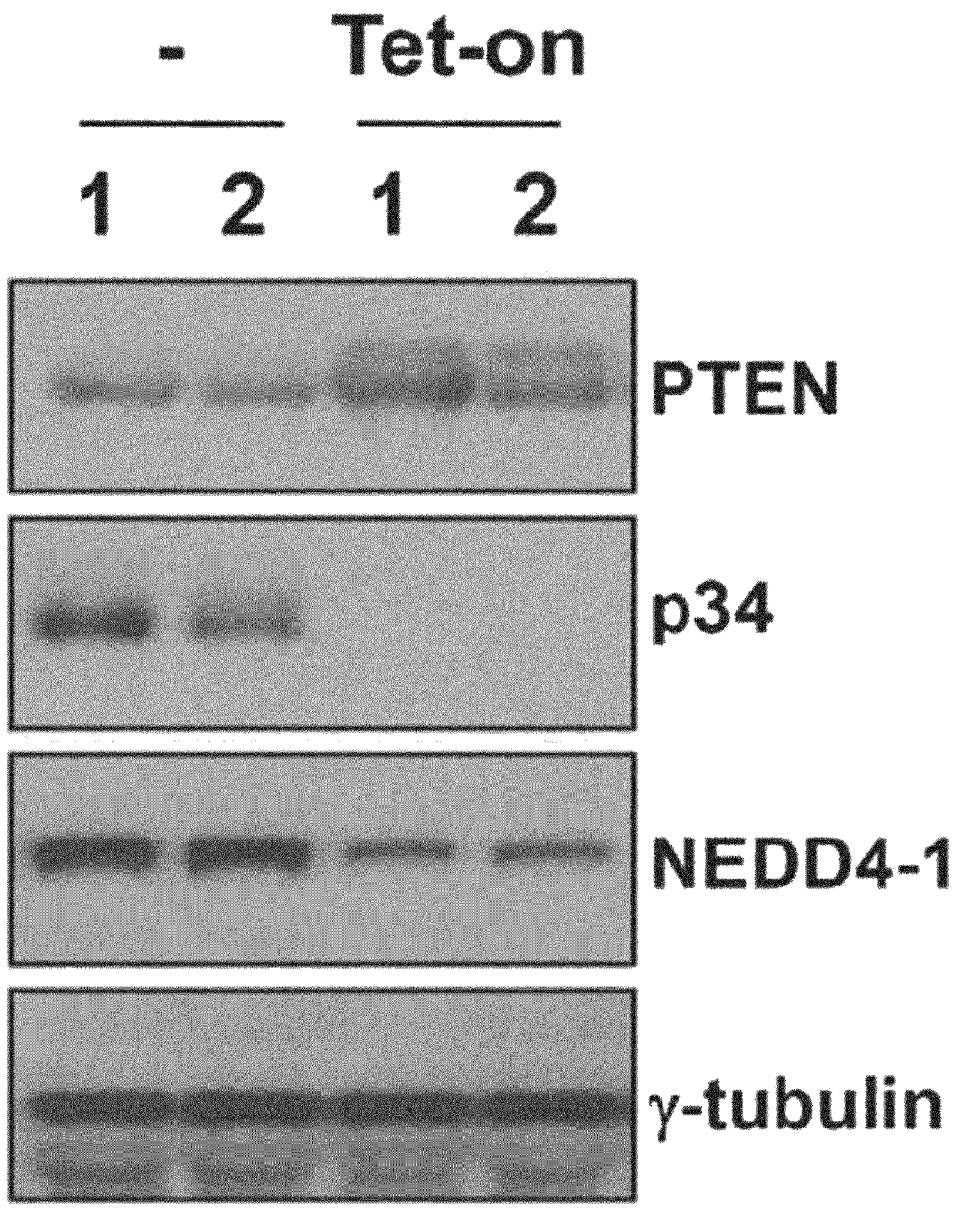

[Fig 48]
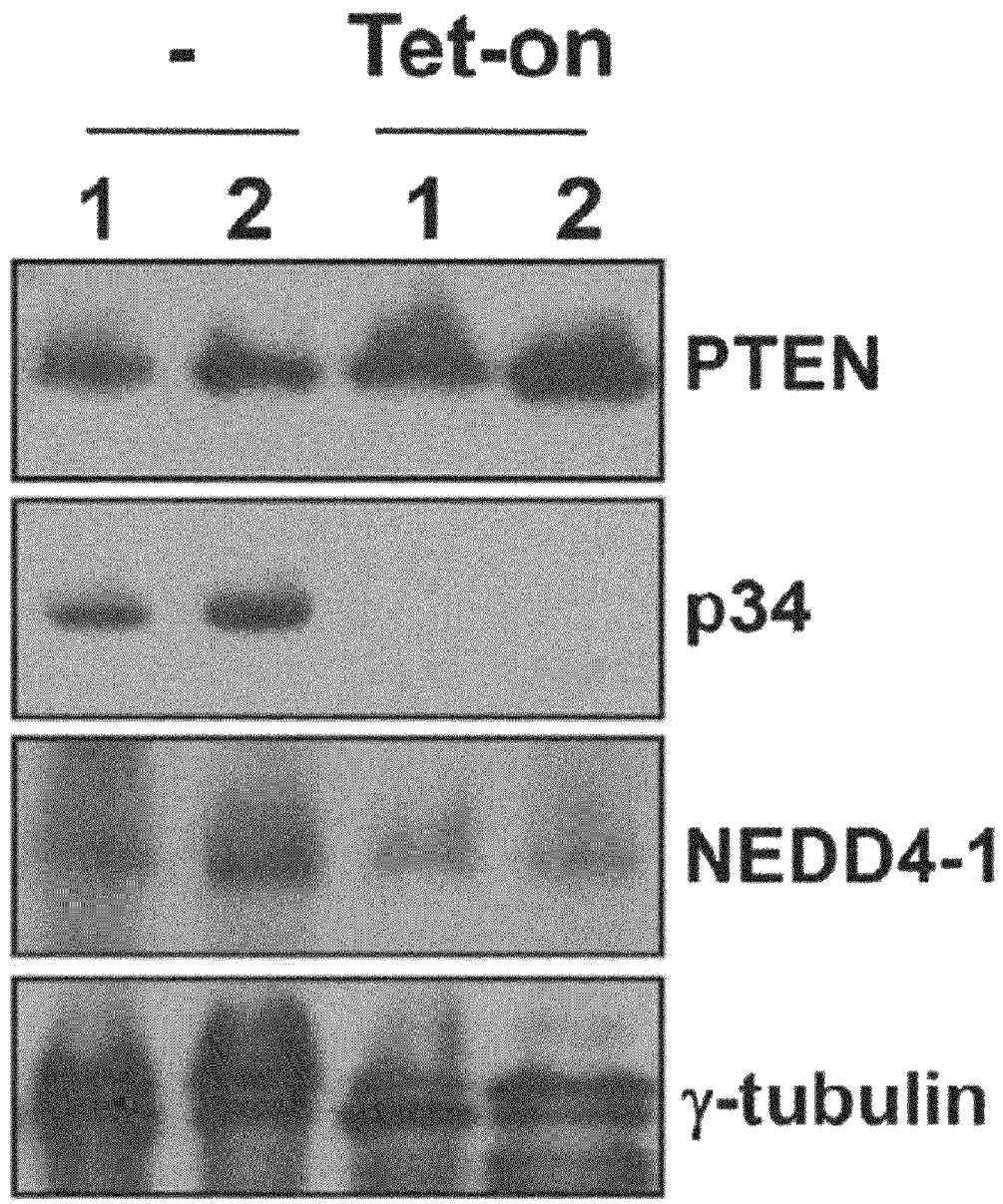

[Fig 49]
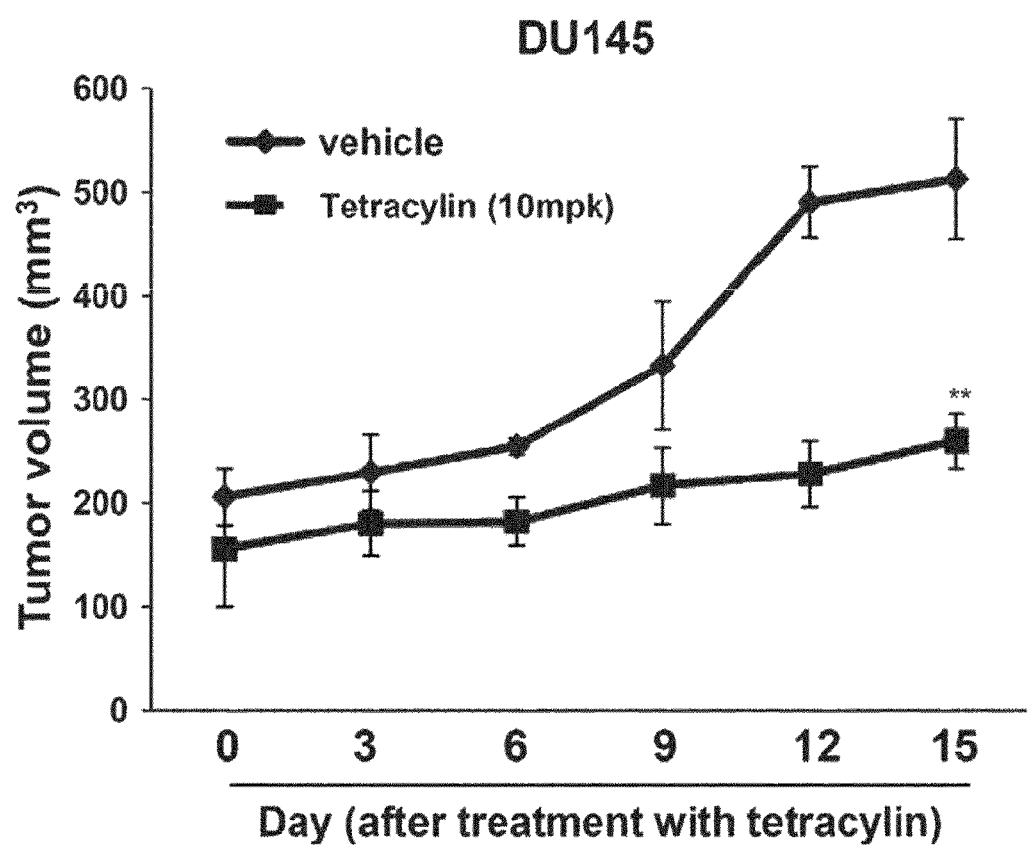

[Fig 50]
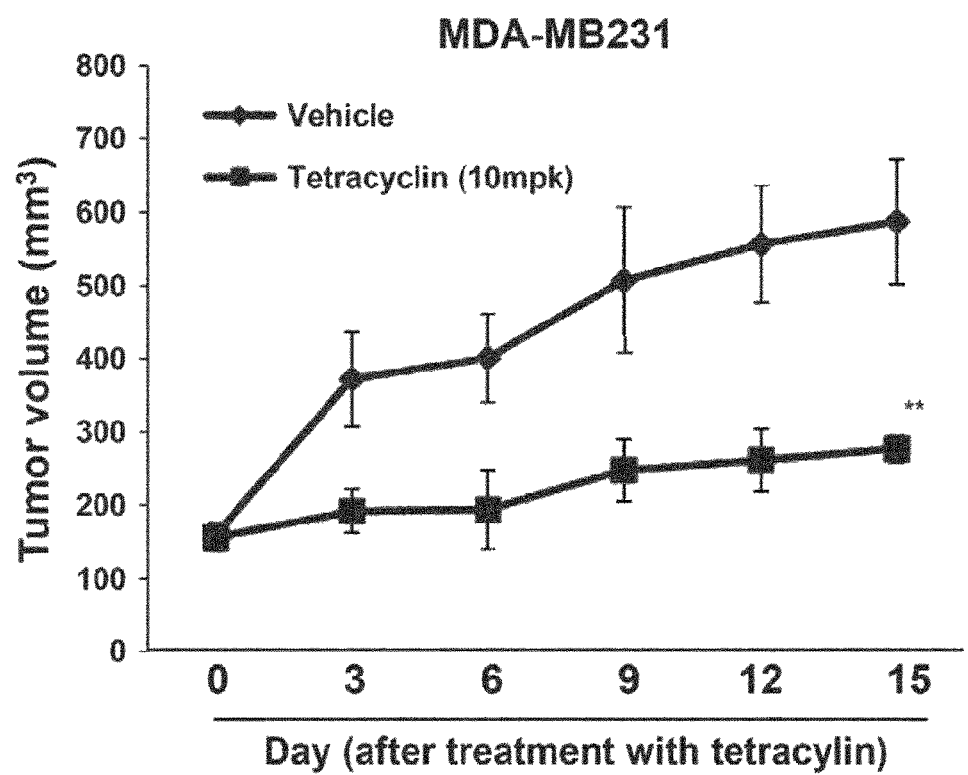

[Fig 51]
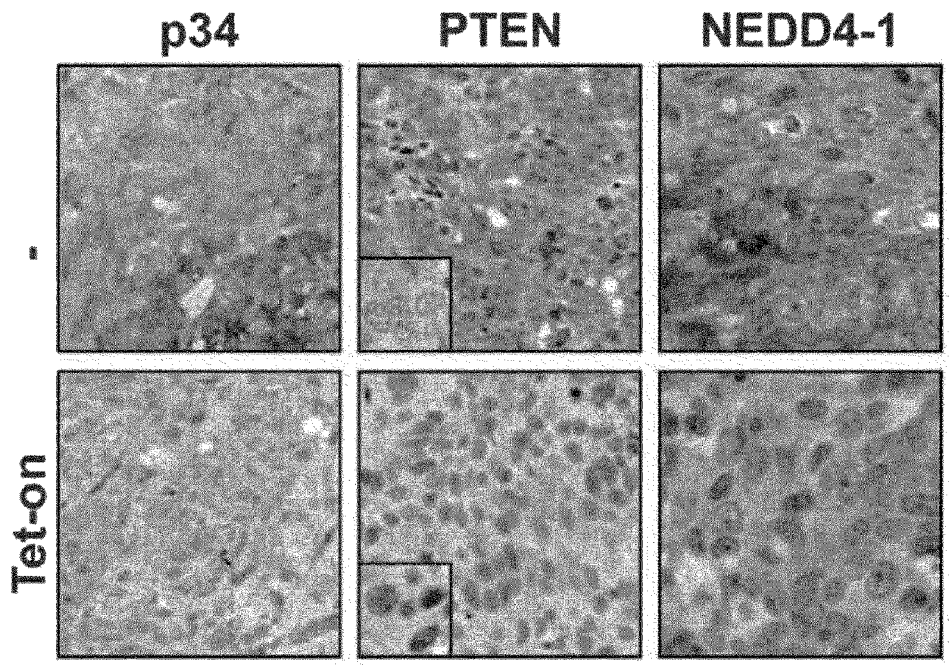
[Fig 52]
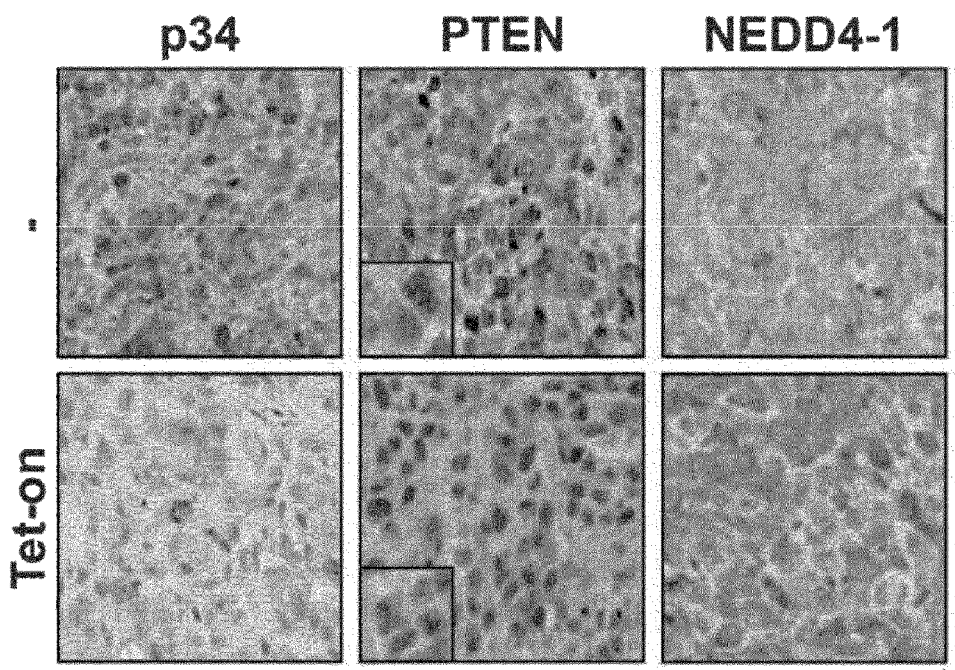

[Fig 53]
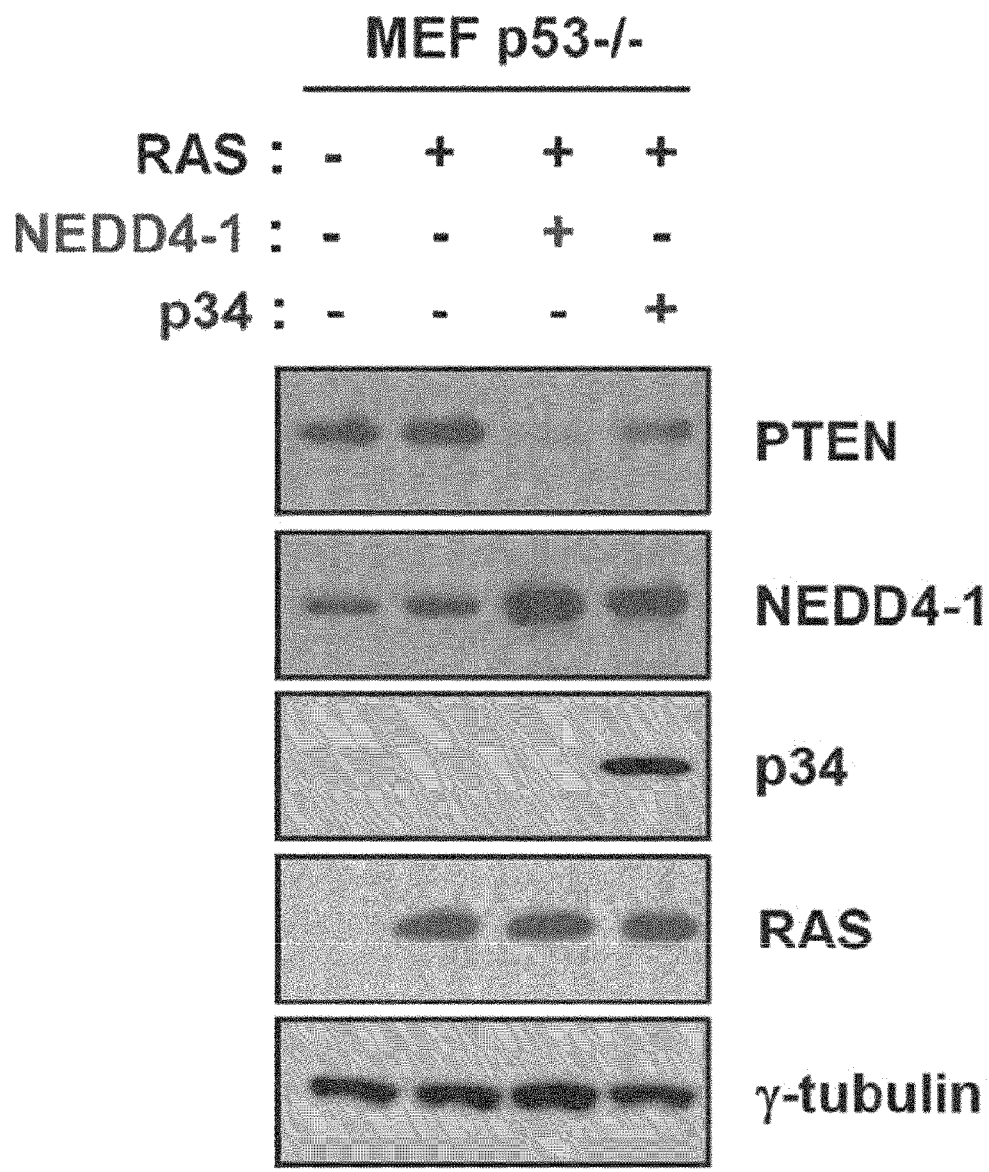

[Fig 54]
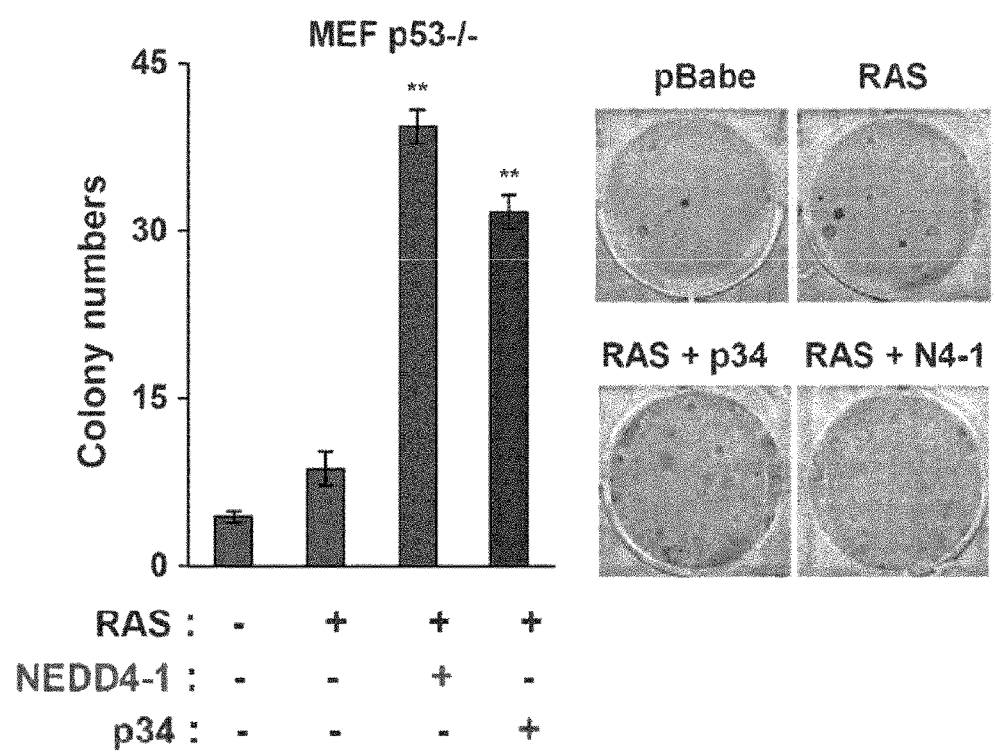

[Fig 55]
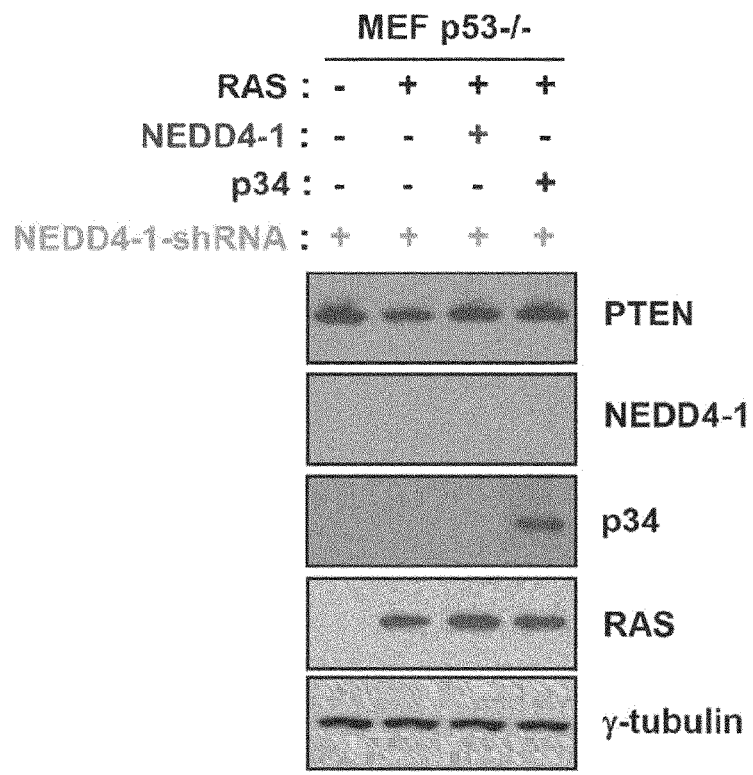

[Fig 56]
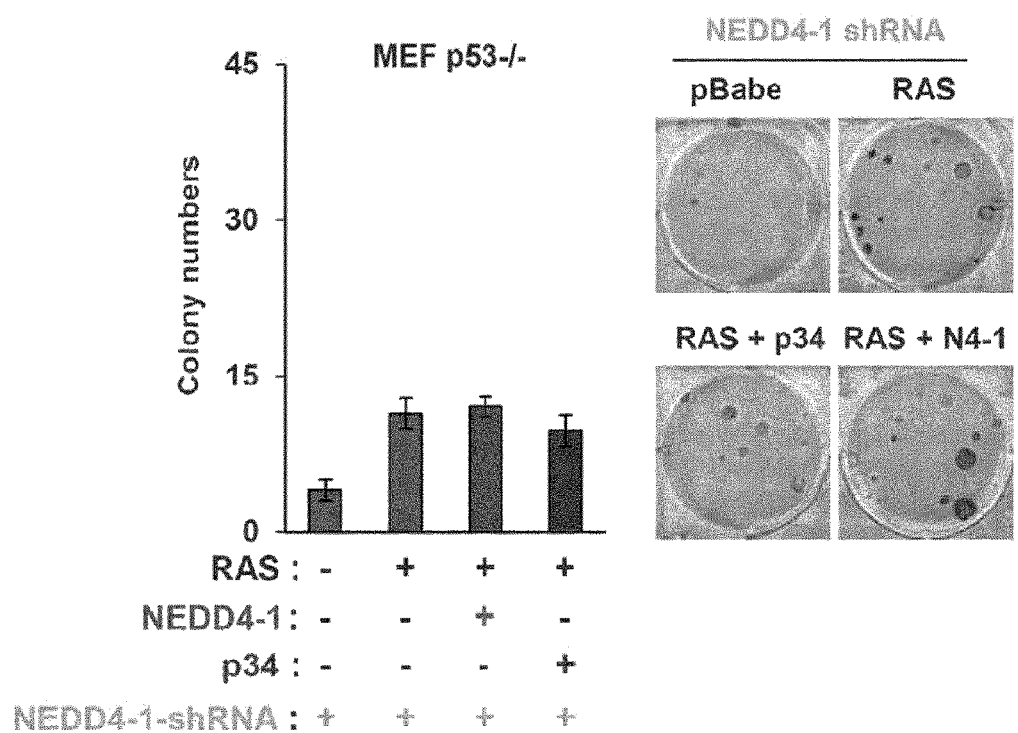

[Fig 57]
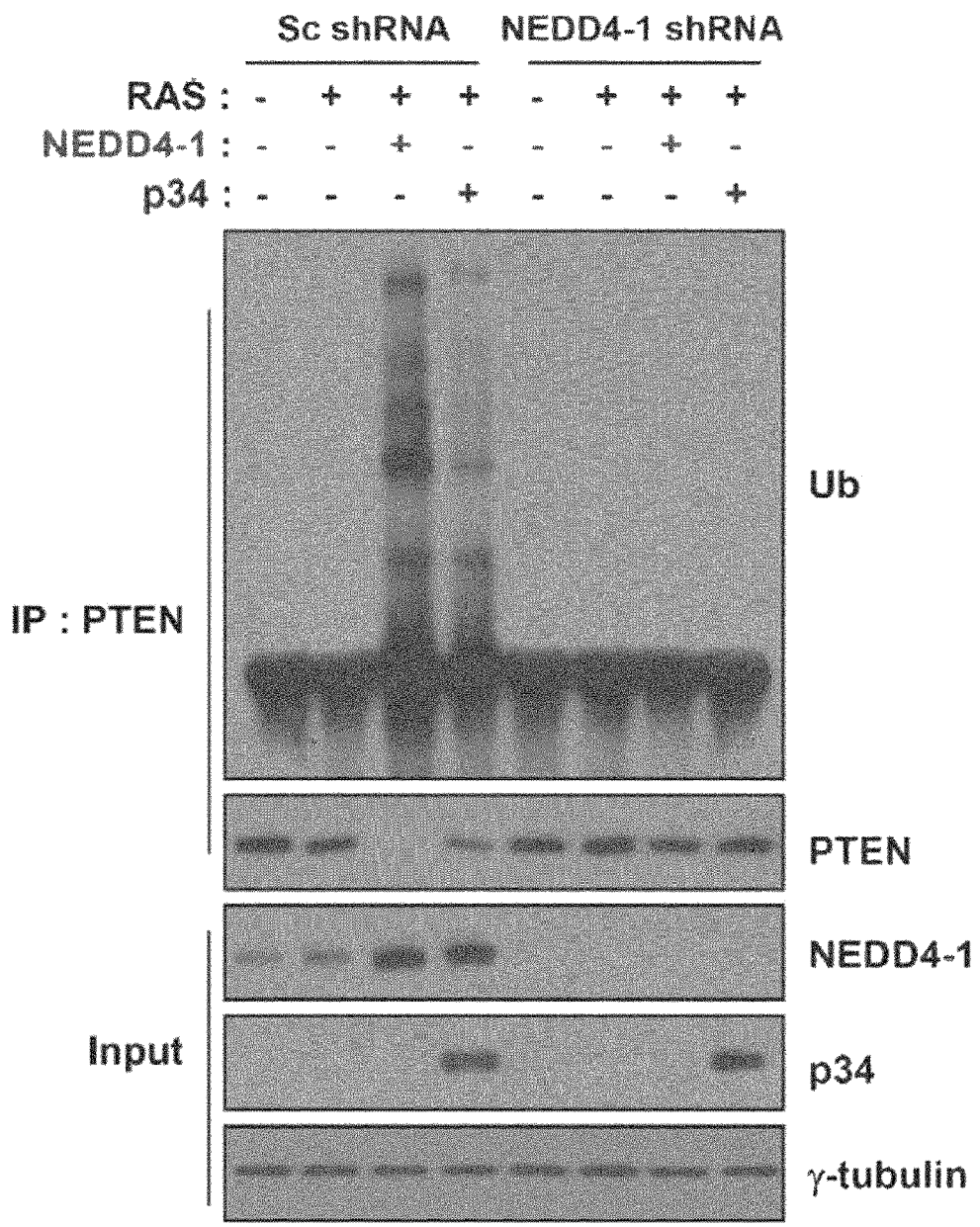

[Fig 58]
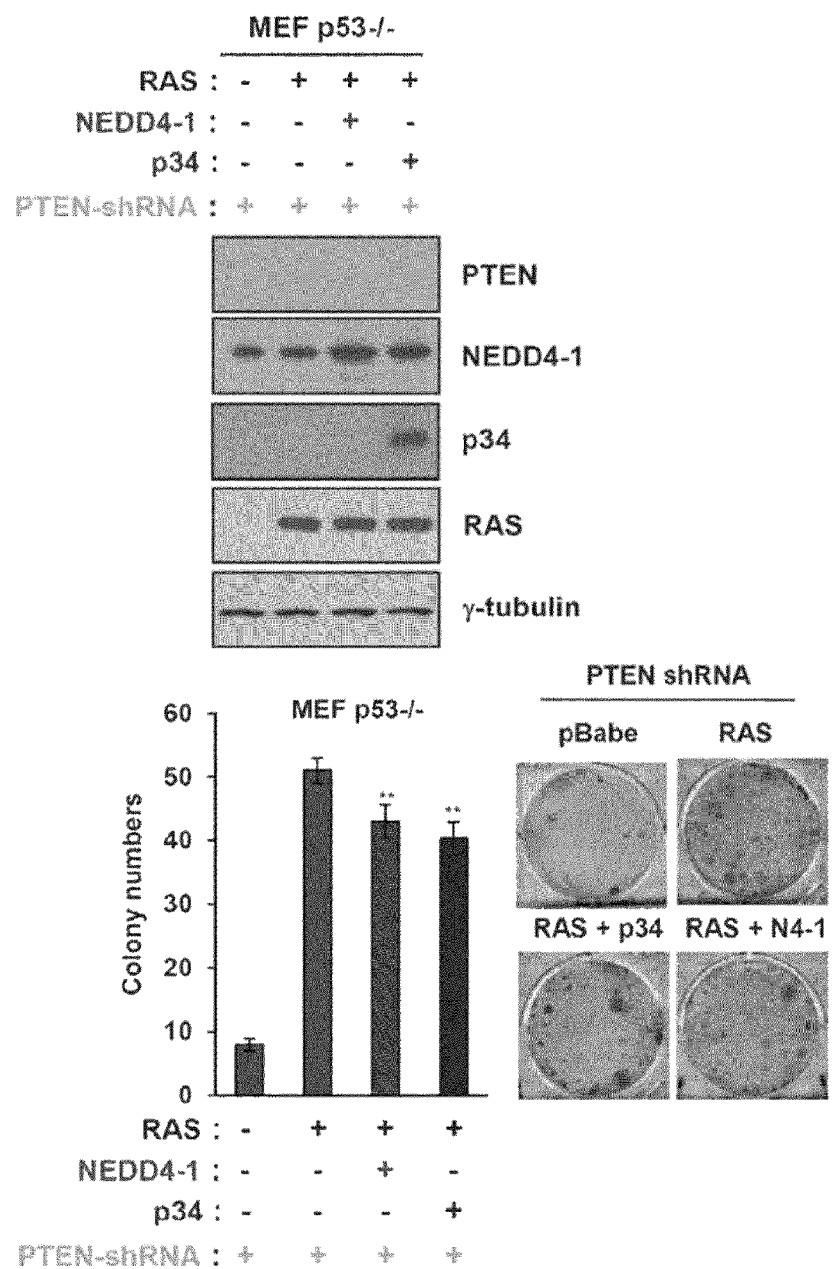

[Fig 59]
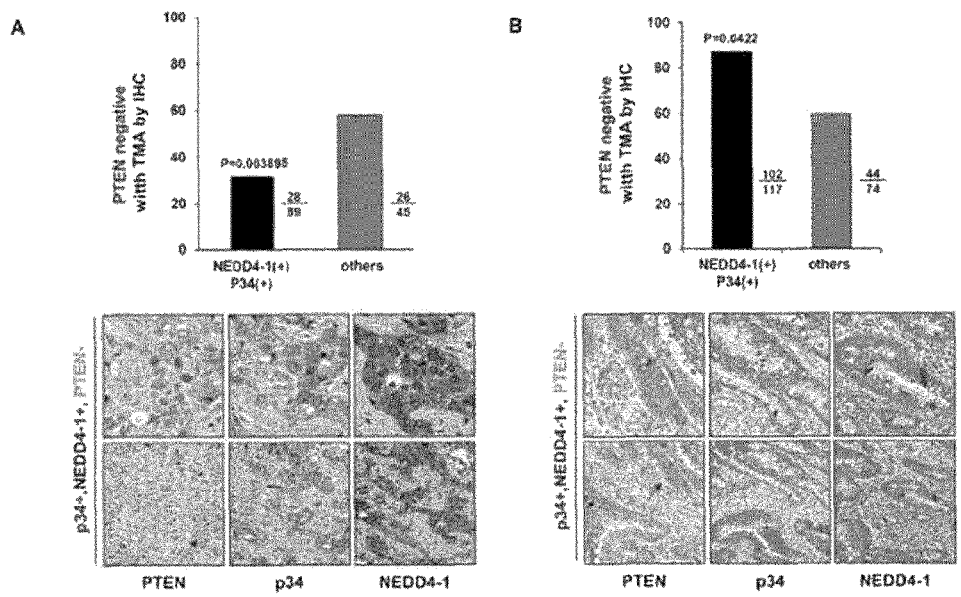
[Fig 60]
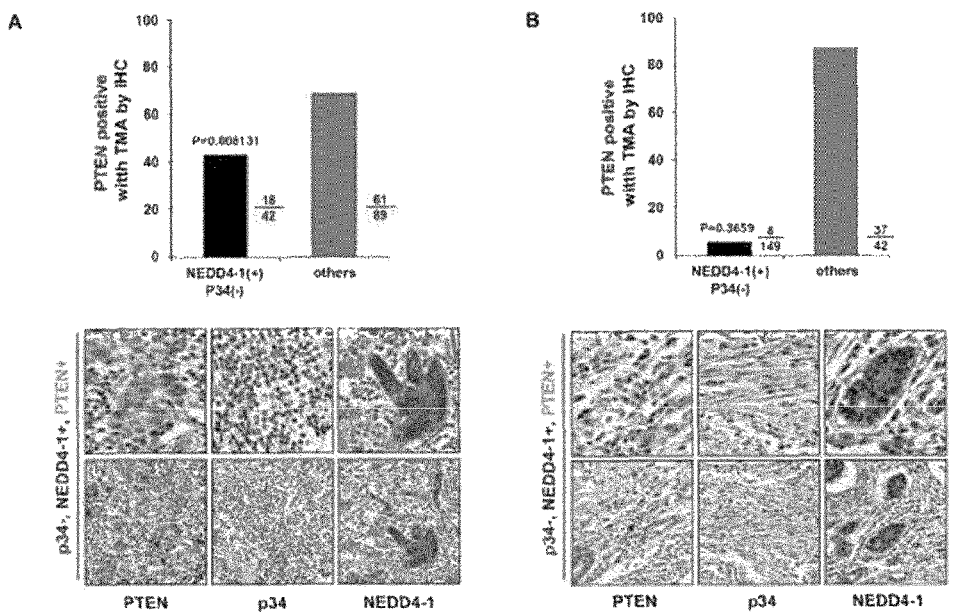

[Fig 61]
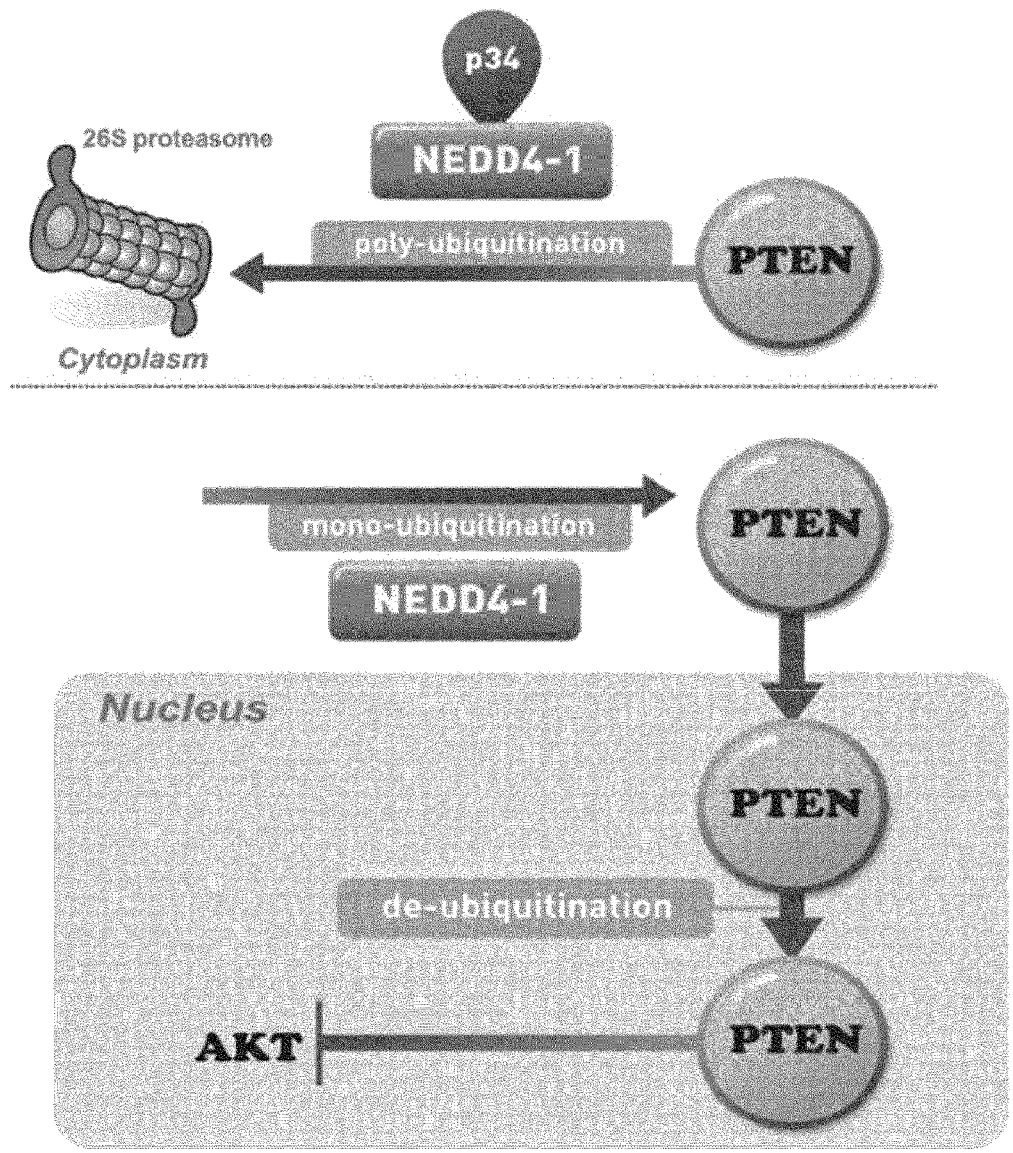

[Fig 62]
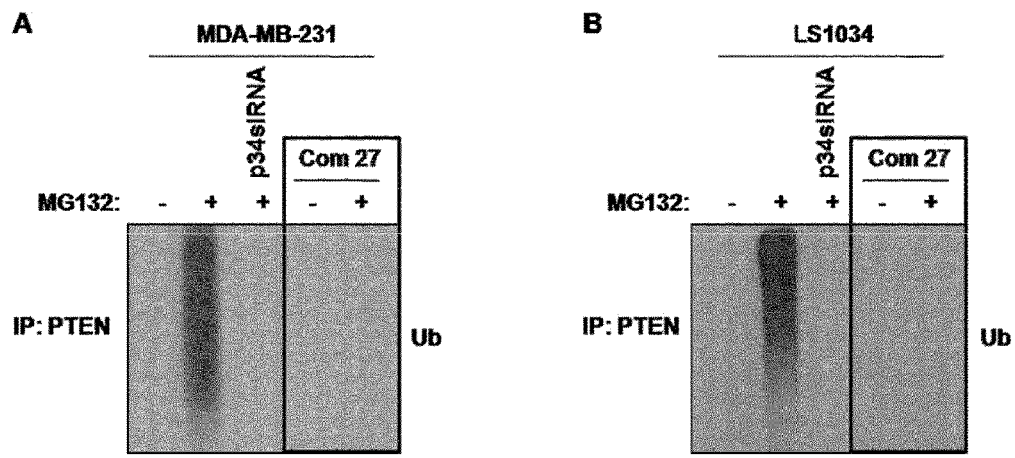
[Fig 63]
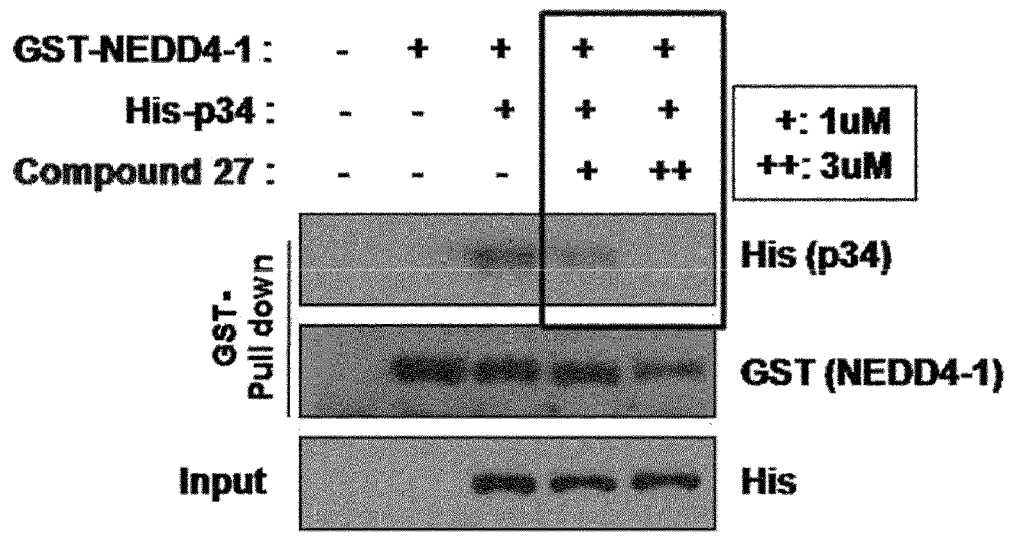

[Fig 64]
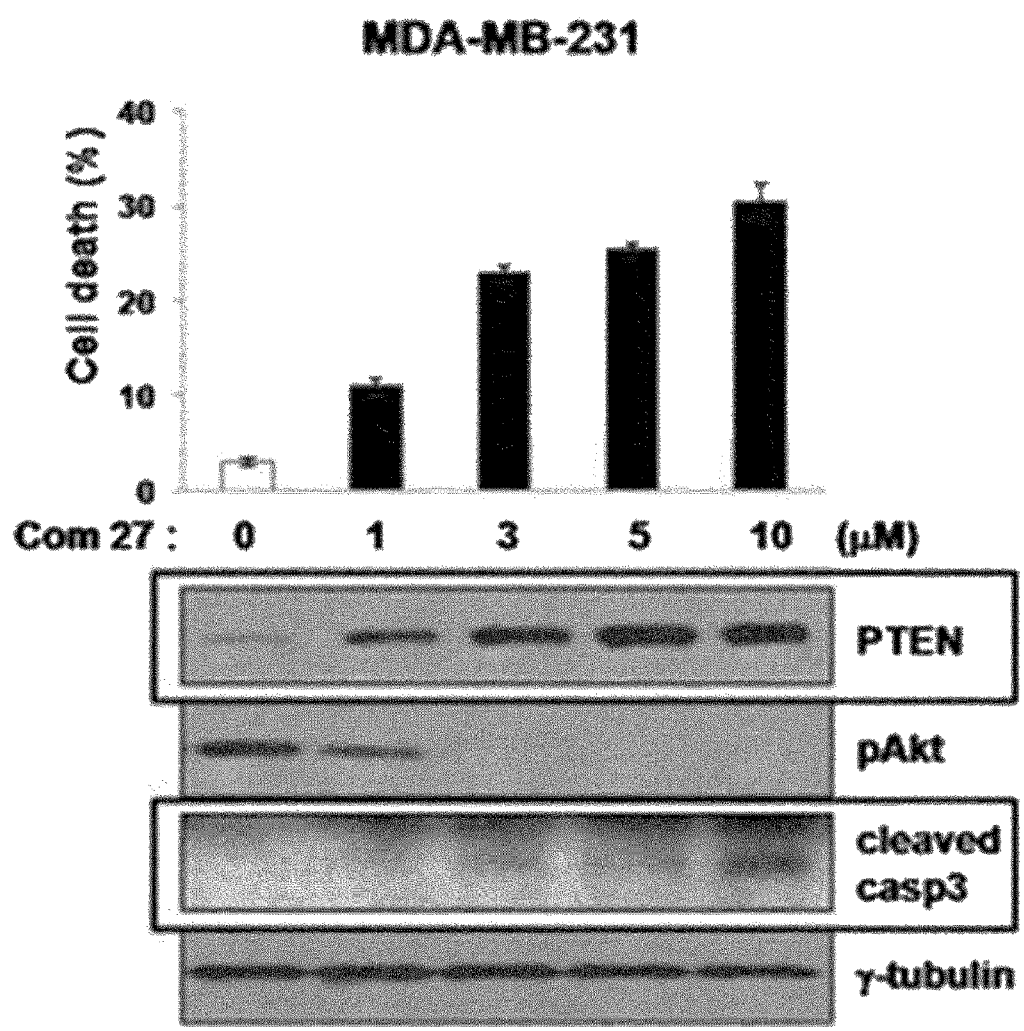

[Fig 65]
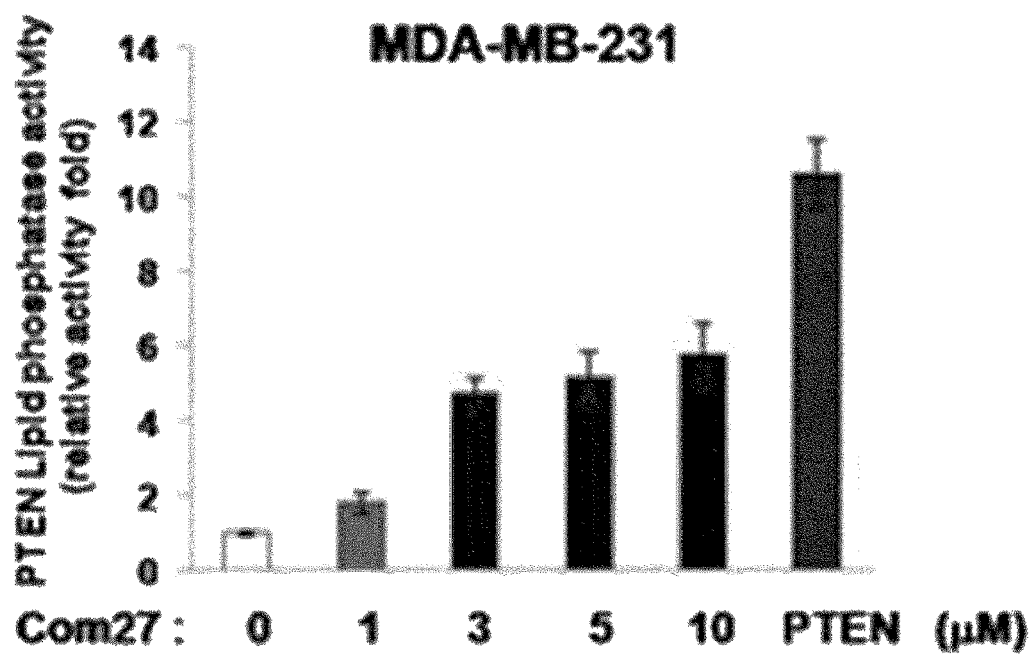

[Fig 66]
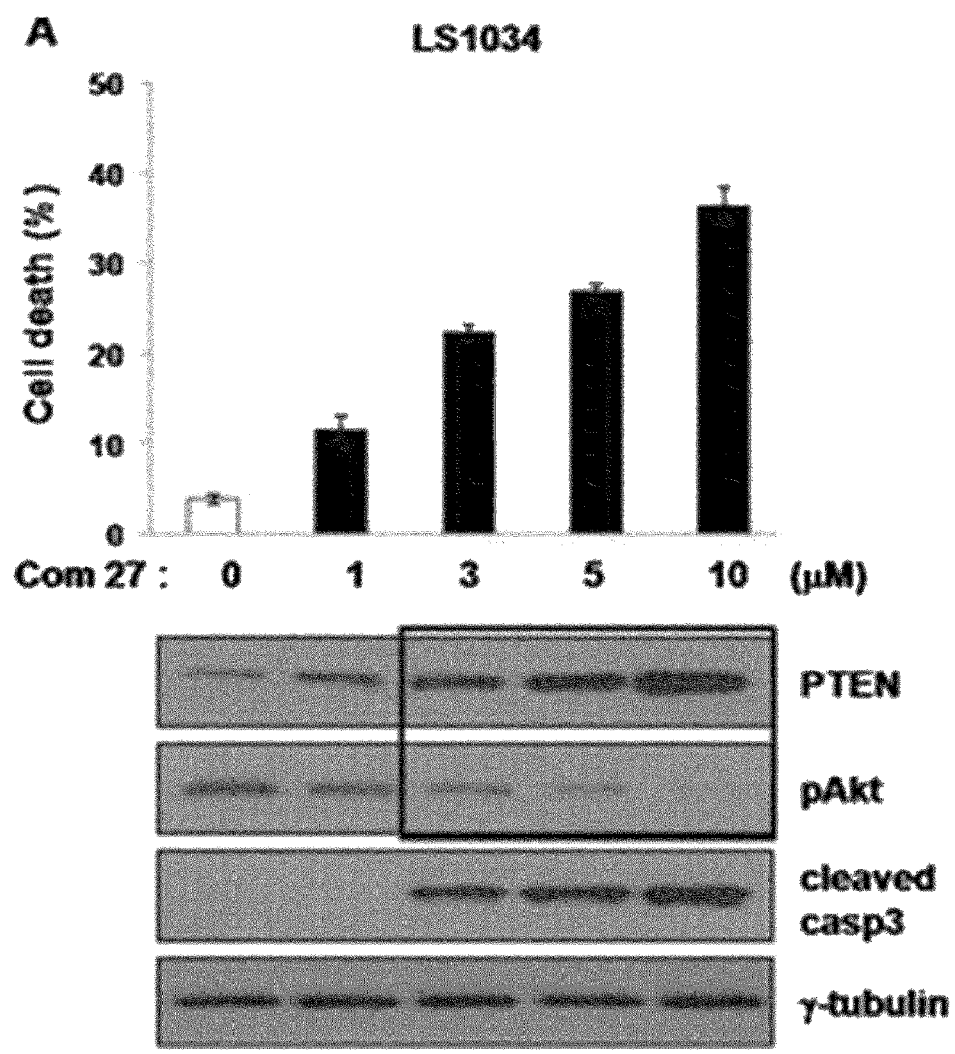

[Fig 67]
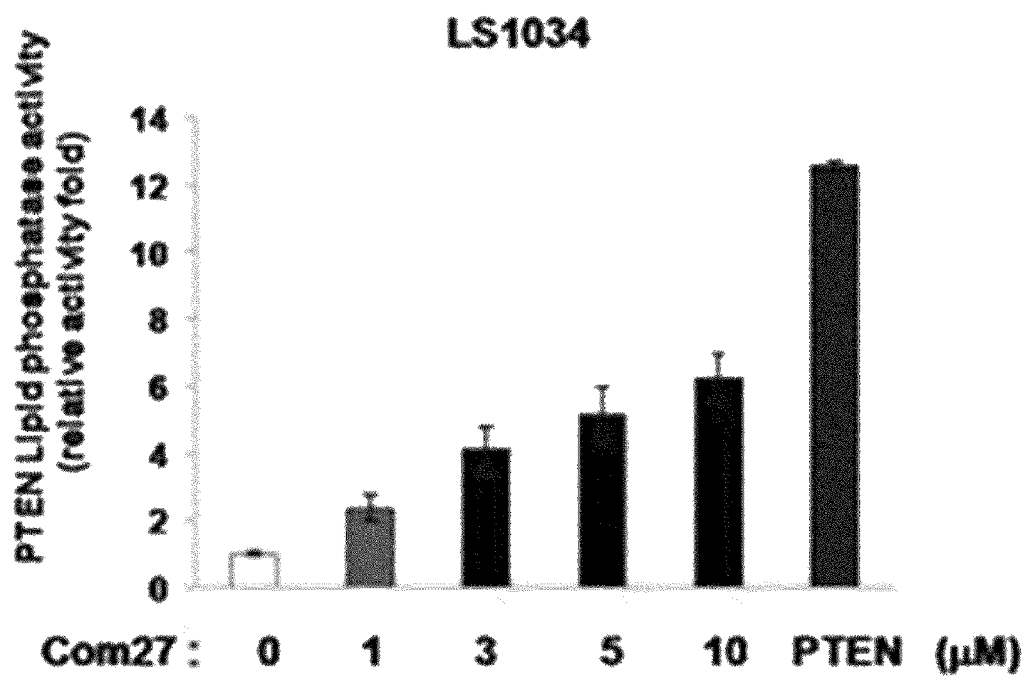

SEQUENCE LISTING

<160> NUMBER OF SEQ ID NOS: 13

<210> SEQ ID NO 1
<211> LENGTH: 19
<212> TYPE: RNA
<213> ORGANISM: Artificial Sequence
<220> FEATURE:
<223> OTHER INFORMATION: Synthetic-p34-siRNA 1

<400> SEQUENCE: 1
gcaagggucu gaagcggaa                                                 19

<210> SEQ ID NO 2
<211> LENGTH: 19
<212> TYPE: RNA
<213> ORGANISM: Artificial Sequence
<220> FEATURE:
<223> OTHER INFORMATION: Synthetic-p34-siRNA 2

<400> SEQUENCE: 2
ggaaacggga ggaggagga                                                 19

<210> SEQ ID NO 3
<211> LENGTH: 19
<212> TYPE: RNA
<213> ORGANISM: Artificial Sequence
<220> FEATURE:
<223> OTHER INFORMATION: Synthetic-p34-siRNA 3

<400> SEQUENCE: 3
ccgaauugga cuaccucau                                                 19

<210> SEQ ID NO 4
<211> LENGTH: 19
<212> TYPE: DNA
<213> ORGANISM: Artificial Sequence
<220> FEATURE:
<223> OTHER INFORMATION: Synthetic-NEDD4-1-siRNA
<400> SEQUENCE: 4
tggcgatttg taaaccgaa                                                 19

<210> SEQ ID NO 5
<211> LENGTH: 20
<212> TYPE: DNA
<213> ORGANISM: Artificial Sequence
<220> FEATURE:
<223> OTHER INFORMATION: Synthetic-p34 Forward Primer
<400> SEQUENCE: 5
tggcctctag ctccctcttt                                                20

<210> SEQ ID NO 6
<211> LENGTH: 21
<212> TYPE: DNA
<213> ORGANISM: Artificial Sequence
<220> FEATURE:
<223> OTHER INFORMATION: Synthetic-p34 Reverse Primer
<400> SEQUENCE: 6
gccagtaagt tgtcagccac a                                              21

<210> SEQ ID NO 7
<211> LENGTH: 20
<212> TYPE: DNA
<213> ORGANISM: Artificial Sequence

```
<220> FEATURE:
<223> OTHER INFORMATION: Synthetic-cdc6 Forward Primer

<400> SEQUENCE: 7
caggttctgg acaatgctgc                                              20

<210> SEQ ID NO 8
<211> LENGTH: 21
<212> TYPE: DNA
<213> ORGANISM: Artificial Sequence
<220> FEATURE:
<223> OTHER INFORMATION: Synthetic-cdc6 Reverse Primer

<400> SEQUENCE: 8
ctgctgaaga gggaaggaat c                                            21

<210> SEQ ID NO 9
<211> LENGTH: 18
<212> TYPE: DNA
<213> ORGANISM: Artificial Sequence
<220> FEATURE:
<223> OTHER INFORMATION: Synthetic-cyclin E2 Forward Primer

<400> SEQUENCE: 9
tgctgccttg tgccattt                                                18

<210> SEQ ID NO 10
<211> LENGTH: 21
<212> TYPE: DNA
<213> ORGANISM: Artificial Sequence
<220> FEATURE:
<223> OTHER INFORMATION: Synthetic-cyclin E2 Reverse Primer

<400> SEQUENCE: 10
gtgctcttcg gtggtgtcat a                                            21

<210> SEQ ID NO 11
<211> LENGTH: 20
<212> TYPE: DNA
<213> ORGANISM: Artificial Sequence
<220> FEATURE:
<223> OTHER INFORMATION: Synthetic-GAPDH Forward Primer

<400> SEQUENCE: 11
agaaggctgg ggctcatttg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic-GAPDH Reverse Primer

<400> SEQUENCE: 12
aggggccatc cacagtcttc                                              20

<210> SEQ ID NO 13
<211> LENGTH: 19
<212> TYPE: DNA
<213> ORGANISM: Artificial Sequence
<220> FEATURE:
<223> OTHER INFORMATION: Synthetic-H1-p34-shRNA

<400> SEQUENCE: 13
ccctctttga cctctcagt                                               19
```

COMPOSITION FOR TREATMENT OR METASTASIS SUPPRESSION OF CANCERS WHICH INCLUDES P34 EXPRESSION INHIBITOR OR ACTIVITY INHIBITOR AS ACTIVE INGREDIENT

CROSS-REFERENCE TO RELATED APPLICATIONS

This application is a U.S. national phase application of International Patent Application No. PCT/KR2014/002617 filed on Mar. 27, 2014, which claims the benefit of Korean patent application 10-2103-0032957, filed Mar. 27, 2013, the disclosures of which are hereby incorporated by reference in their entireties.

TECHNICAL FIELD

The present invention relates to pharmaceutical compositions for treatment or metastasis suppression of cancers comprising p34 expression inhibitors or activity inhibitors as active ingredients.

BACKGROUND ART

Cancers are one of major diseases which threaten human's health, and are diseases caused by a process where cells are subjected to a series of mutations, and proliferated and immortalized in an unlimited and uncontrolled manner. Causes of cancer occurrence are environmental or external sources such as chemical substances, viruses, bacteria, ionizing radiation, and the like, or internal sources such as inherited genetic change, and the like (Klaunig & Kamendulis, Annu Rev Pharmacol Toxicol., 44:239-267, 2004). When cancers are discovered in their initial stage, therapy, such as surgery, radiation therapy, chemotherapy, and the like, can be performed, but there are big concerns that side effects are accompanied therewith. In the case of terminal cancers or metastatic cancers, there are no special therapies and patients are given limited time period to live.

Recently, various biochemical mechanisms associated with cancers have been identified, and therapeutic agents thereagainst have been developed. However, no basic treatment methods for cancers have been suggested until now. Thus, studies aiming to identify various in vivo molecules related to cancers and develop drugs targeting at these molecules have been actively progressed. Also, an effort to enhance the effect of treating cancers has been made by combining part of these drugs. Therefore, an effort to additionally discover target molecules related to cancers is very important.

The phosphatase and tensin homolog (PTEN) tumor suppressor, a major negative regulator in phosphatidylinositol-3-kinase (PI3K) signal transfer step, is known as the most frequently mutated and deleted genes in human cancers. According to recent studies, important questions related to ubiquitination in regulating the functions of the tumor suppressor PTEN are raised, and the studies for regulating mechanisms required for PTEN ubiquitination have been continuously conducting.

The present inventors found during the studies on PTEN mechanism related to ubiquitination that p34 protein, a binding partner of neuronal precursor cell-expressed developmentally down-regulated 4-1 (NEDD4-1), controls the stability of NEDD4-1 protein, and thereby controls the conversion of PTEN mono- and poly-ubiquitination.

Specifically, an increase in p34 expression interacts with the WW1 domain of NEDD4-1, an E3 ubiquitin ligase, and enhances its protein stability, which result in PTEN polyubiquitination and PTEN protein degradation, whereas p34 knockdown causes PTEN mono-ubiquitination and promotes nuclear localization of PTEN, which result in inhibiting Akt pathways related to survival, proliferation, invasive properties, and metastatic properties of tumors.

Thus, the present inventors confirmed that p34 may act as a key regulator in PTEN ubiquitination pathway by regulating NEDD4-1 protein stability, and particularly may be an effective target for treatment of a cancer associated with NEDD4-1 and PTEN, and then completed the present invention.

SUMMARY OF INVENTION

The present invention is to provide a composition for prevention or treatment of a cancer comprising a p34 gene expression inhibitor or a p34 protein activity inhibitor as an active ingredient.

Also, the present invention is to provide a composition for metastasis suppression of a cancer comprising a p34 gene expression inhibitor or a p34 protein activity inhibitor as an active ingredient.

Also, the present invention is to provide a method for treatment or metastasis suppression of a cancer comprising administering a p34 gene expression inhibitor or a p34 protein activity inhibitor to an individual.

Also, the present invention is to provide a method for screening a candidate substance for treatment or metastasis suppression of a cancer using p34.

Also, the present invention is to provide a method for predicting treatment effect of a p34 gene expression inhibitor or a p34 protein activity inhibitor on a cancer, comprising treating a biological sample with an NEDD4-1 expression inhibitor or activity inhibitor.

In order to achieve the above subject matters, the present invention provides a pharmaceutical composition for prevention or treatment of a cancer comprising a p34 gene expression inhibitor or a p34 protein activity inhibitor as an active ingredient.

Also, the present invention provides a food composition for prevention or improvement of a cancer comprising a p34 gene expression inhibitor or a p34 protein activity inhibitor as an active ingredient.

Also, the present invention provides a pharmaceutical composition for metastasis suppression of a cancer comprising a p34 gene expression inhibitor or a p34 protein activity inhibitor as an active ingredient.

Also, the present invention provides a method for treatment or metastasis suppression of a cancer comprising administering a p34 gene expression inhibitor or a p34 protein activity inhibitor to an individual.

Also, the present invention provides a method for screening a candidate substance for treatment or metastasis suppression of a cancer comprising the following steps:

1) treating a p34 protein expression cell line with a testing substance;

2) measuring a p34 gene expression level or a p34 protein activity level in the cell line; and 3) selecting a testing substance where the p34 gene expression level or p34 protein activity level is reduced compared with a control group which is not treated with a testing substance.

Also, the present invention provides a method for predicting the treatment effect of a p34 gene expression inhibitor or a p34 protein activity inhibitor on a cancer comprising the following steps:

1) treating a biological sample with an expression inhibitor or an activity inhibitor of neuronal precursor cell-expressed developmentally down-regulated 4-1 (NEDD4-1); and 2) measuring the proliferation of cancer cells in the biological sample.

According to the present invention, the knock-down of p34 protein causes mono-ubiquitination of PTEN and accordingly nuclear localization of PTEN is induced. As a result, an Akt pathway which is related to survival, proliferation, invasive properties and metastatic properties of tumors is inhibited, and thus there is an effect of significantly reducing clonogenic potential and tumor forming potential of various cancer cells which co-express PTEN and NEDD4-1. Consequently, the p34 gene expression inhibitor or p34 protein activity inhibitor according to the present invention can be effectively used as a treatment agent or a metastasis suppression agent for cancers.

BRIEF DESCRIPTION OF DRAWINGS

FIG. 1 is a view illustrating a result of immunoprecipitation using NEDD-1 in 293, DU145 and MCF-7 cells;

FIG. 2 is a view illustrating a result of expression levels of p34, NEDD4-1, and PTEN proteins in 293, DU145 and MCF-7 cells by Western blotting;

FIG. 3 is a view illustrating a result of expression levels of p34 and NEDD4-1 in immunoprecipitates of DU145 and MCF-7 cells by Western blotting;

FIG. 4 is a view illustrating a result of immunoprecipitation to NEDD4-1 protein in LS1034 and MDA-MB231 cells;

FIG. 5 is a view illustrating a result of expression levels of p34, NEDD4-1 and PTEN proteins in various colon cancer and breast cancer cell lines by Western blotting;

FIG. 6 is a view illustrating a result of immunoprecipitation to p34 and NEDD4-1 in 293 cells;

FIG. 7 is a view illustrating a result of expression levels of p34 and NEDD4-1 by GST-pull down assay and Western blotting;

FIG. 8 is a view illustrating a result of expression levels of p34, PTEN and NEDD4-1 by GST-pull down assay and Western blotting;

FIG. 9 is a view illustrating a NEDD4-1 mutant map, and result of interaction between p34 and NEDD4-1 proteins by GST-pull down assay;

FIG. 10 is a view illustrating a result of GST-pull down assay in NEDD4-1 protein lacking WW1 domain;

FIG. 11 is a view illustrating a result of interaction between p34, NEDD4-1, and PTEN proteins by GST-pull down assay;

FIG. 12 is a view illustrating NEDD4-1 auto-ubiquitination according to p34 expression and MG132 treatment conditions by immunoprecipitation;

FIG. 13 is a view illustrating NEDD4-1 auto-ubiquitination according to p34 expression by GST-pull down assay;

FIG. 14 is a view illustrating NEDD4-1 expression level according to p34 or NEDD4-1 expression and CHX treatment conditions by Western blotting;

FIG. 15 is a view illustrating expression levels of NEDD4-1 and p34 proteins according to p34 knockdown by Western blotting;

FIG. 16 is a view illustrating an expression level of PTEN protein according to p34 knockdown by Western blotting;

FIG. 17 is a view illustrating an expression level of PTEN protein according to p34 expression by Western blotting;

FIG. 18 is a view illustrating an expression level of PTEN protein according to p34 knockdown and CHX treatment conditions by Western blotting;

FIG. 19 is a view illustrating an expression level of PTEN protein according to transfection with p34 and treatment with MG132 in 293 cells by Western blotting;

FIG. 20 is a view illustrating an ubiquitination level of PTEN protein according to transfection with p34 and treatment with MG132 in each cell;

FIG. 21 is a view illustrating a poly-ubiquitination level of PTEN protein according to p34 knockdown in each cell;

FIG. 22 is a view illustrating a PTEN lipid phosphatase activity according to p34 expression in 293 cells;

FIG. 23 is a view illustrating an expression level of PTEN and Akt phosphorylation in cells transfected NEDD4-1 siRNA/shRNA and p34 by Western blotting;

FIG. 24 is a view illustrating an expression level of PTEN according to p34, NEDD4-1 siRNA, and CHX treatment by Western blotting;

FIG. 25 is a view illustrating an ubiquitination level of PTEN protein according to transfection of NEDD4-1 siRNA/shRNA and p34, and MG132 treatment;

FIG. 26 is a view illustrating a PTEN lipid phosphatase activity level according to p34 expression and NEDD4-1 knockdown;

FIG. 27 is a view illustrating an expression level of XIAP in XIAP-knockout MEF cells by Western blotting;

FIG. 28 is a view illustrating an expression level of PTEN protein according to p34 transfection result in XIAP-knockout MEF cells by Western blotting;

FIG. 29 is a view illustrating an expression level of PTEN protein according to p34 transfection result in XIAP-knockout MEF cells by immunoprecipitation and Western blotting;

FIG. 30 is a view illustrating an expression level of mono-ubiquitinated PTEN in p34-knockdown MCF-7, MDA-MB-231, DU145, and LS1034 cells;

FIG. 31 is a view illustrating an expression level of mono-ubiquitinated PTEN in p34-knockdown MEF cells per locations of nuclear fractions and cytosol;

FIG. 32 is a view illustrating an expression level of mono-ubiquitinated PTEN according to p34 or NEDD4-1 knockout in MCF-7 cells;

FIG. 33 is a view illustrating an expression level of poly-ubiquitinated PTEN according to NEDD4-1 or p34 expression;

FIG. 34 is a view illustrating an expression level of poly-ubiquitinated PTEN according to NEDD4-1 or p34 expression;

FIG. 35 is a view illustrating an ubiquitination level of PTEN according to the presence of E2 enzyme and p34 or NEDD4-1 expression;

FIG. 36 is a view illustrating growth of LS0135 and MCF7 cells according to p34 knockout;

FIG. 37 is a view illustrating colony forming potential of LS0135 and MCF7 cells according to p34 knockout;

FIG. 38 is a view illustrating a size of LS0135 and MCF7 cell colonies according to p34 knockout;

FIG. 39 is a view illustrating expression levels of p34, cyclin E2, and cdc6 genes in LS0135 and MCF7 cells according to p34 knockout;

FIG. 40 is a view illustrating establishment of DU145 and MDA-MB-231 mutants expressing tetracycline-inducible p34-shRNA vectors through TetR expression;

FIG. 41 is a view illustrating expression levels of p34, PTEN, and phosphorylated Akt after tetracycline treatment to tetracycline-inducible DU145 and MDA-MB-231 mutants;

FIG. 42 is a view illustrating an activity level of PTEN phosphatase after tetracycline treatment to tetracycline-inducible DU145 and MDA-MB-231 mutants;

FIG. 43 is a view illustrating colony forming potential after tetracycline treatment to tetracycline-inducible DU145 and MDA-MB-231 mutants;

FIG. 44 is a view illustrating cell growth after tetracycline treatment to tetracycline-inducible DU145 and MDA-MB-231 mutants;

FIG. 45 is a view illustrating BrdU incorporation after tetracycline treatment to tetracycline-inducible DU145 and MDA-MB-231 mutants;

FIG. 46 is a view illustrating PTEN expression and colony forming potential in p34 expressed Hs578T cell lines;

FIG. 47 is a view illustrating expression levels of PTEN, p34, and NEDD4-1 according to tetracycline administration, after tumor formation by injecting tetracycline-inducible DU145 mutants to mice;

FIG. 48 is a view illustrating expression levels of PTEN, p34, and NEDD4-1 according to tetracycline administration, after tumor formation by injecting tetracycline-inducible MDA-MB-231 mutants to mice;

FIG. 49 is a view illustrating a change in tumor volume according to tetracycline administration, after tumor formation by injecting tetracycline-inducible DU145 mutants to mice;

FIG. 50 is a view illustrating a change in tumor volume according to tetracycline administration, after tumor formation by injecting tetracycline-inducible MDA-MB-231 mutants to mice;

FIG. 51 is a view illustrating nuclear localization of PTEN protein according to tetracycline administration, after tumor formation by injecting tetracycline-inducible DU145 mutants to mice;

FIG. 52 is a view illustrating nuclear localization of PTEN protein according to tetracycline administration, after tumor formation by injecting tetracycline-inducible MDA-MB-231 mutants to mice;

FIG. 53 is a view illustrating expression levels of PTEN and NEDD4-1 proteins in p53$^{-/-}$/MEF cells;

FIG. 54 is a view illustrating colony forming potential according to Ras, p34, and NEDD4-1 expressions in p53$^{-/-}$/MEF cells;

FIG. 55 is a view illustrating expression levels of PTEN and NEDD4-1 proteins in NEDD4-1 knockdown-p53$^{-/-}$ MEF cells;

FIG. 56 is a view illustrating colony forming potential according to Ras, p34, and NEDD4-1 expressions in NEDD4-1 knockdown-p53$^{-/-}$ MEF cells;

FIG. 57 is a view illustrating PTEN poly-ubiquitination level in NEDD4-1 knockdown-p53$^{-/-}$ MEF cells;

FIG. 58 is a view illustrating Ras activity in p53$^{-/-}$/MEF cells;

FIG. 59 is a view illustrating an expression ratio of PTEN protein according to NEDD4-1/p34 expression in various breast cancer and colon cancer cells;

FIG. 60 is a view illustrating an expression ratio of PTEN protein according to NEDD4-1/p34 expression in various breast cancer and colon cancer cells;

FIG. 61 is a schematic diagram illustrating overall interaction between p34, NEDD4-1, and PTEN;

FIG. 62 is a view illustrating inhibition on PTEN ubiquitination according to treatment with a p34 activity inhibitor in human breast cancer and colorectal cancer cells;

FIG. 63 is a view illustrating inhibitory effect of p34 and NEDD4-1 proteins binding according to treatment with a p34 activity inhibitor;

FIG. 64 is a view illustrating an effect of treatment with a p34 activity inhibitor on cell death and protein expression in human breast cancer cell lines;

FIG. 65 is a view illustrating an effect of treatment with a p34 activity inhibitor on PTEN lipid phosphatase activity in human breast cancer cell lines;

FIG. 66 is a view illustrating an effect of treatment with a p34 activity inhibitor on cell death and protein expression in human colorectal cancer cell lines; and FIG. 67 is a view illustrating an effect of treatment with a p34 activity inhibitor on PTEN lipid phosphatase activity in human colorectal cancer cell lines.

BEST MODE FOR CARRYING OUT THE INVENTION

Hereinafter, the present invention is described in detail.

The present invention provides a composition for prevention or treatment of a cancer comprising a p34 gene expression inhibitor or a p34 protein activity inhibitor as an active ingredient.

Also, the present invention provides a composition for metastasis suppression of a cancer comprising a p34 gene expression inhibitor or a p34 protein activity inhibitor as an active ingredient.

The composition includes a pharmaceutical composition or a food composition.

The p34 gene expression inhibitor according to the present invention may be at least one selected from the group consisting of an antisense nucleotide, a small hairpin RNA (shRNA), a small interfering RNA (siRNA), and a ribozyme, binding complementarily to mRNA of the p34 gene, but is not limited thereto.

The p34 protein activity inhibitor according to the present invention may be at least one selected from the group consisting of a compound, a peptide, a peptide mimetic, a substrate analog, an aptamer, and an antibody, binding specifically to p34 protein, but is not limited thereto.

As defined by Watson-Crick base pairs, the antisense nucleotide is hybridized with a complementary sequence of DNA, immature-mRNA or mature-mRNA to interrupt the transmission of genetic information as a protein in DNA.

The siRNA is composed of a sense sequence of 15 to 30-mers selected from the mRNA base sequence of a gene that encodes the p34 protein and an antisense sequence complementarily binding to the sense sequence. Here, preferably, the sense sequence may be composed of 25 nucleotides, but is not particularly limited thereto.

The compound includes any compounds capable of specifically binding to p34 protein and inhibiting its activity, and preferably has the activity of inhibiting p34 and NEDD4-1 proteins binding, but is not limited thereto. An example of the present invention provides, as an example of a compound specifically binding to p34 protein, a compound represented by the following formula 1 or a pharmaceutically acceptable salt thereof:

[Formula 1]

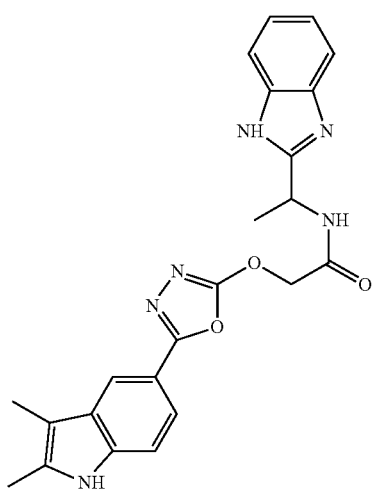

As used herein, the term "pharmaceutically acceptable salt" refers to any organic or inorganic addition salt of the compound represented by the formula 1 in a concentration with efficacy which is relatively nontoxic and harmless to an individual, where side effects caused by the salt do not lower beneficial efficacy of the compound. The pharmaceutically acceptable salt of the compound represented by the formula 1 includes all salts of acidic or alkaline groups which may be present in compounds represented by the formula 1, unless indicated otherwise.

The peptide mimetics act to inhibit the activity of p34 protein by inhibiting the binding domain of p34 protein. The peptide mimetics may be peptides or non-peptides, and may include amino acids linked by non-peptide bonds, like psi bonds. Also, the peptide mimetics may be "conformationally constrained" peptides, cyclic mimetics, and cyclic mimetics including at least one exocyclic domain, a linking moiety (a linking amino acid) and an active region. The peptide mimetics can be constructed to resemble secondary structural features of p34 protein and mimic inhibitory features of large molecules such as antibodies or soluble receptors, and may be novel small molecules which can act with the effect equivalent to natural antagonists.

The aptamer, a single-stranded DNA or RNA molecule, may be obtained by isolating oligomers binding to specific chemical molecules or biological molecules with high affinity and selectivity by an evolutionary process using an oligonucleotide library called as systematic evolution of ligands by exponential enrichment (SELEX). The aptamer may bind specifically to a target to regulate its activity and may inhibit the function of the target through bonds, for example.

The antibody may effectively inhibit the activity of p34 protein by specifically and directly binding to p34 protein. As the antibody specifically binding to p34 protein, a polyclonal antibody or a monoclonal antibody may be preferably used. An antibody specifically binding to p34 protein may be produced by a process known to those skilled in the art, or a commercially available p34 antibody may be purchased and used. The antibody may be produced by injecting p34 protein, as an immunogen, into an external host, according to a conventional method known to those skilled in the art. The external host includes mammals such as a mouse, a rat, a sheep, a rabbit, and the like. The immunogen is injected through intramuscular, intraperitoneal or subcutaneous injection, and is generally administered with an adjuvant for improving antigenicity. Blood samples may be taken from the external host at regular intervals and serum exhibiting titer and specificity to the antigen may be collected to separate an antibody therefrom.

According to the present invention, the inhibition of p34 causes mono-ubiquitination of PTEN and accordingly nuclear localization of PTEN is induced. As a result, an Akt pathway which is related to survival, proliferation, invasive properties and metastatic properties of tumors is inhibited. Thus, there is an effect of significantly reducing clonogenic potential and tumor forming potential of various cancer cells which co-express PTEN and NEDD4-1. Consequently, the p34 gene expression inhibitor or p34 protein activity inhibitor can be effectively used as a treatment agent or a metastasis suppression agent for cancers.

The cancer includes oral cancer, liver cancer, stomach cancer, colon cancer, breast cancer, lung cancer, bone cancer, pancreatic cancer, skin cancer, head cancer, neck cancer, cervical cancer, ovarian cancer, colorectal cancer, small intestinal cancer, rectal cancer, fallopian tube cancer, anal cancer, endometrial carcinoma, carcinoma of vagina, vulval cancer, Hodgkin's disease, esophageal cancer, lymphoma, bladder cancer, gallbladder cancer, endocrine glandular cancer, thyroid cancer, parathyroid cancer, adrenal cancer, soft tissue sarcoma, urethral cancer, testicular cancer, prostate cancer, chronic leukemia, acute leukemia, lymphocytic lymphoma, kidney cancer, ureter cancer, kidney cell cancer, renal pelvic cancer, CNS tumor, primary CNS lymphoma, spinal cord tumor, brain-stem glioma, pituitary adenoma, and the like, and preferably includes breast cancer, colon cancer, stomach cancer, liver cancer, lung cancer, prostate cancer, and the like, but is not limited thereto.

Also, the cancer includes all cancers simultaneously expressing p34 and NEDD4-1, but is not limited thereto.

The composition of the present invention may further include at least one of known active ingredients having anticancer effect.

The composition of the present invention may be formulated in a suitable form with a pharmaceutically acceptable carrier. Examples of the pharmaceutically acceptable carrier may include a carrier for oral administration, such as lactose, starch, a cellulose derivative, magnesium stearate, stearic acid, and the like, and a carrier for parenteral administration, such as water, suitable oil, saline solution, aqueous glucose, glycol, and the like, and may further include a stabilizer and a preservative in addition thereto. Examples of the suitable stabilizer may include an antioxidant, such as sodium bisulfite, sodium sulfite, or ascorbic acid. Examples of the suitable preservative may include benzalkonium chloride, methyl- or propyl-paraben, and chlorobutanol. As other pharmaceutically acceptable carriers, the carriers as disclosed in the following document can be referred (Remington's Pharmaceutical Sciences, 19th ed., Mack Publishing Company, Easton, Pa., 1995).

The pharmaceutical composition of the present invention may be administered orally or parenterally (e.g., intravenously, subcutaneously, intraperitoneally or topically) according to the intended use. The dosage of the composition may vary depending on a patient's weight, age, health condition, diet, administration time, administration method, administration period or interval, excretion rate, constitutional peculiarity, properties of a formulation, and the like. The dosage of the pharmaceutical composition of the present invention is about 0.001 to 1000 mg/kg per day and may be added or reduced according to clinical test results. Preferably, the pharmaceutical composition may be administered once or several times a day.

The pharmaceutical composition of the present invention may be formulated in an administration unit form. For example, the formulated administration unit may include 1, 2, 3, or 4 times, or ½, ⅓, or ¼ times of a single administration amount per day of the active compound. Preferably, the single administration amount may contain the amount where the active compound is administered once, which corresponds to all of the dosage a day, or ½, ⅓, or ¼ times thereof.

Also, the composition of the present invention may be variously used in a medicine, a food and a beverage, which are effective in preventing or improving a cancer.

Examples of the food to which the p34 gene expression inhibitor or p34 protein activity inhibitor of the present invention may be added include various foods, beverages, gum, tea, vitamin complexes, dietary supplements, and the like, and may be used in the form of powders, granules, tablets, capsules, or drinks Here, the amount of the active ingredient in the food or beverage product may be generally added in an amount of 0.01 to 15 wt % with respect to the total weight of the food, and may be added in an amount of 0.02 to 10 g with respect to 100 mL of a health beverage composition, and preferably in an amount of 0.3 to 1 g.

Besides including the above active ingredients as essential ingredients in the percentage indicated above, the health functional food of the present invention may include food acceptable additives such as various flavoring agents or natural carbohydrates, and the like, as additional ingredients. Examples of natural carbohydrates may include common sugars, including monosaccharides, such as glucose, fructose, and the like, disaccharides, such as maltose, sucrose, and the like, and polysaccharides, such as dextrin, cyclodextrin, and the like, and sugar alcohols, such as xylitol, sorbitol, erythritol, and the like. In addition, other flavorings may be advantageously used, including natural flavoring agents (thaumatin, stevia extracts (e.g., rebaudioside A, glycyrrhizin, and the like)) and synthetic flavoring agents (saccharin, aspartame, and the like). The content of the natural carbohydrates is generally about 1 to 20 g per 100 mL of the health functional food of the present invention. In addition, the health functional food of the present invention may contain various nutrients, vitamins, minerals (electrolytes), flavoring agents, such as synthetic flavoring agents, natural flavoring agents, and the like, coloring agents, extenders (cheese, chocolate, and the like), pectic acid and its salt, alginic acid and its salt, organic acid, protective colloid thickeners, PH adjusters, stabilizers, preservatives, glycerin, alcohols, carbonating agents used for carbonated drinks, and the like. In addition, the health functional food of the present invention may contain pulp that may be used for preparing natural fruit juice, fruit juice beverage, and vegetable beverage. Such components may be used independently or in combination with other ingredients.

Also, the present invention provides a method for treatment or metastasis suppression of a cancer, comprising administering to an individual a p34 gene expression inhibitor or a p34 protein activity inhibitor.

The method for treatment or metastasis suppression of a cancer of the present invention includes administering to an individual a p34 gene expression inhibitor or a p34 protein activity inhibitor in a therapeutically effective amount. As for specific individuals, the therapeutically effective amount is preferably determined based on various factors, including the type and degree of reaction to be achieved, specific compositions including whether other formulations may be used depending on cases, patient's age, body weight, general health condition, gender and diet, the administration time and route and excretion rate of the composition, the treatment period, the drug administered in combination or simultaneously with the specific composition, and like factors well known in the medical arts. Accordingly, the effective amount of the composition suitable for the purpose of the present invention is preferably determined based on the above matters.

In the present invention, the subject may be any mammals with cancers, and the mammals include humans and primates, and livestock including cow, pig, sheep, horse, dog, cat, and the like.

Also, the present invention provides a method for screening a candidate substance for treatment or metastasis suppression of a cancer, comprising 1) treating a p34 protein expression cell line with a testing substance; 2) measuring a 34 gene expression level or a p34 protein activity level in the cell line; and 3) selecting a testing substance where the p34 gene expression level or p34 protein activity level are reduced compared with a control group which is not treated with a testing substance.

In the method, the cell line in the step 1) includes all cancer cell lines, and preferably includes a cancer cell line simultaneously expressing p34 and NEDD4-1, but is not limited thereto.

In the method, the gene expression level in the step 2) may be measured by Reverse Transcription Polymerase Chain Reaction (RT-PCR), Northern blotting, cDNA microarray hybridization reaction, in situ hybridization reaction, and the like, and may be measured by all techniques measuring the amount of gene, which are known to those skilled in the art, but is not limited thereto.

In the method, the protein active level in the step 2) may be measured by immunoprecipitation, radioimmunoassay (RIA), immunosorbent assay (ELISA), immunohistochemistry, Western blotting, fluorescence activated cell sorter (FACS), and the like, and may be measured by all techniques measuring the amount of protein, which are known to those skilled in the art, but is not limited thereto.

Also, the present invention provides a method for predicting treatment effect of a p34 gene expression inhibitor or a p34 protein activity inhibitor on a cancer, comprising 1) treating a biological sample with an expression inhibitor or an activity inhibitor of neuronal precursor cell-expressed developmentally down-regulated 4-1 (NEDD4-1); and 2) measuring proliferation of cancer cells in the biological sample.

In the method, the biological sample in the step 1) may include blood, urine, salvia, and tissues of an individual with a cancer, but is not limited thereto.

The method further includes 3) predicting that the p34 expression inhibitor or activity inhibitor has no treatment effect on the cancer if cancer cells of the biological sample proliferate, and that the p34 expression inhibitor or activity inhibitor has treatment effect on the cancer if cancer cells of the biological sample do not proliferate.

In cancers expressing NEDD4-1 and PTEN only and cancers expressing PTEN only, the treatment with the p34 gene expression inhibitor or p34 protein activity inhibitor may not have treatment effect, and in cancers simultaneously expressing NEDD4-1, PTEN, and p34, the treatment with the p34 gene expression inhibitor or p34 protein activity inhibitor may have anti-cancer effect.

Hereinafter, preferred Examples will be provided to facilitate understanding of the present invention. However, the following Examples are provided for better understanding of the present invention only, and the scope of the present invention is not limited by the following Examples.

Example 1

In Vivo and In Vitro Interaction Between p34 and NEDD4-1, and Analysis of p34 on NEDD4-1 Protein Stability

Example 1-1

Analysis of Interaction Between Endogenous p34 and NEDD4-1

(1) In order to identify proteins which interact with NEDD4-1, immunoprecipitation, tandem affinity purification, and mass spectrometric analyses were performed using an antibody against NEDD4-1 protein from cell lysates. First, in order to perform the immunoprecipitation analyses, the cell lysates of 293 (HEK 293) cells, prostate cancer cells DU145, and breast cancer cells MCF7 were mixed with the anti-NEDD4-1 antibodies, respectively, and incubated at 4° C. for 12 hours. Then, 20 μl of protein A/G Plus-Sepharose beads (Santa Cruz Biotechnology, Santa Cruz, Calif., USA) was added to the culture to be mixed, and the mixture was incubated for an additional 2 hours. The obtained immunoprecipitates were washed five times with a lysis buffer (nonidet P-40 lysis buffer) and boiled in 20 μl of 2×SDS sample buffer.

Further, in order to perform Western blotting, the proteins isolated from each cell were isolated using SDS-PAGE and transferred to PolyScreen membranes (New England Nuclear, Boston, Mass., USA). Then, the experiments were performed according to a conventionally known process using various antibodies (anti-PTEN (Cell Signaling, Beverly, Calif., USA), anti-p34 (Enzo LifeSciences, Beverly, Mass., USA), anti-NEDD4-1 and g-tubulin (Santa Cruz Biotechnology)).

The results are illustrated in FIGS. 1 and 2.

As illustrated in FIG. 1, it is confirmed that p34 was present among various proteins which were identified as interacting with NEDD4-1 (indicated with red arrow). As illustrated in FIG. 2, p34 was expressed in 2 cancer cell lines (DU145, and MCF7 cells) among 3 cell lines. p34 is known as binding to cyclin-dependent kinase 4 (CDK4) and X-linked inhibitor of apoptosis protein (XIAP).

(2) In order to verify the above results, the present inventors observed the interaction between endogenous p34 and NEDD4-1 in DU145, MCF7 and LS1034 cells by immunoprecipitation and Western blotting. The results are illustrated in FIGS. 3 and 4.

As illustrated in FIGS. 3 and 4, a p34-binding NEDD4-1 and NEDD4-1-binding p34 were observed in all of DU145, MCF7 and LS1034 cells.

(3) In order to verify the above experimental results in other cancer cell lines, the present inventors analyzed p34 and NEDD4-1 expressions in various colon cancer and breast cancer cell lines (HT-29, HCT-116, LS174T, DLD1, CoLo201, LS1034, BT-20, MDA-MB-231, Hs578T, and the like). The result is illustrated in FIG. 5.

As illustrated in FIG. 5, the interaction between p34 and NEDD4-1 was observed in LS1034 and MDA-MB231 cell lines which co-express p34 and NEDD4-1 proteins.

Example 1-2

Analysis of Interaction Between Exogenous p34 and NEDD4-1

In order to investigate the interaction between exogenously expressed p34 and NEDD4-1, 293 cells which do not endogenously express p34 were transfected with constructs expressing GFP-tagged p34 and/or myc-tagged NEDD4-1. Then, the lysates of 293 cells were analyzed by immunoblotting. The result is illustrated in FIG. 6.

As illustrated in FIG. 6, GFP-tagged p34 was detected in myc-tagged NEDD4-1 immunoprecipitates of 293 cells. Thus, it can be confirmed that there was an interaction between exogenously expressed p34 and NEDD4-1.

Example 1-3

Analysis of Interaction Between p34, NEDD4-1, and PTEN

In order to observe the interaction between p34, NEDD4-1, and PTEN, the following GST pull-down analysis was performed. First, 500 ng of GST-p34 protein or GST protein (control group) expressed and purified from E. coli BL-21 (DE3) lines were prepared, mixed with NEDD4-1 deletion mutant cell lines in a reaction buffer (20 mM Tris-HCl pH 7.5, 120 mM NaCl) and incubated at 30° C. for 1 hour. Then, GST-pull down buffer (20 mM Tris-HCl pH 8.0, 500 mM NaCl, 1% Triton X-100, 0.02% BSA, 5 mM mercaptoethanol) was added to stop the reaction. Then, GST and relevant proteins were pulled down using Glutathione-Sepharose beads at 4° C. for 1 hour. The protein complexes were washed with GST-pull down buffer six times and added 2×SDS sample buffer thereto. The presence of p34 and NEDD4-1 in immunoprecipitates was analyzed by immunoblot using anti-GST and anti-T7 antibodies, respectively. The results are illustrated in FIGS. 7 and 8.

As illustrated in FIG. 7, it is confirmed that p34-bound NEDD4-1 proteins were detected in the immunoprecipitates.

Also, as illustrated in FIG. 8, as a result of analyzing p34 and PTEN binding by incubating purified recombinant GST-PTEN with Myc-NEDD4-1, it is confirmed that PTEN-bound p34 proteins were not detected, which means that p34, unlike NEDD4-1, does not bind to PTEN.

From the above experimental results, it can be understood that p34 directly interacts with NEDD4-1, but does not interact with PTEN.

Example 1-4

Analysis of NEDD4-1 Domain Interacting with p34

(1) Through Example 1-3 above, the domain of NEDD4-1 protein that was confirmed to interact with p34 was analyzed. To this end, T7-tagged wild-type NEDD4-1 and NEDD4-1 mutants lacking a part of domain of NEDD4-1 were prepared from NEDD4-1 cDNA expressing plasmid using T7-tagged vectors. Purified GST-p34 proteins were incubated with the lysing solution of 293 cells expressing T7-tagged wild-type NEDD4-1 or NEDD4-1 mutants lacking C2, WWs and homologous to the E6-AP carboxyl terminus (HECT) domain (N1), WWs and HECT domain (N2), C2, WW3, WW4 and HECT domain (N3), C2, WW1, WW2 and HECT domain (N4), and C2 and WWs domains (N5). Thereafter, the domain of NEDD4-1 to which p34 binds was analyzed by GST-pull down assay. The result is illustrated in FIG. 9.

As illustrated in FIG. 9, GST-p34 was detected in NEDD4-1-wild type and NEDD4-1-N3. This indicates that p34 interacts with domains containing WW1 and WW2 of NEDD4-1.

Based on the above experimental result, it was attempted to confirm which one of the WW1 or WW2 domain of NEDD4-1 was involved in direct binding to p34. To this end, 2 mutant constructs (N6, N7) of NEDD4-1 containing the WW1 or the WW2 domain, respectively, were prepared. Purified GST-p34 proteins were incubated with the lysing solution expressing the NEDD4-1 mutants, and then GST-pull down assay was performed. The result is illustrated in FIG. 9.

As illustrated in FIG. 9, it is confirmed that GST-p34 was clearly detected in the WW1 domain of NEDD4-1, and this indicates that p34 directly binds to the WW1 domain of NEDD4-1.

(2) In order to verify the above result, plasmids containing GST-tagged wild-type NEDD4-1 mutants lacking WW1 domain (GST-delWW1) were prepared. The mutant proteins of NEDD4-1 were incubated with a lysing solution isolated from cells expressing His-p34, and then GST-pull down assay was performed. The result is illustrated in FIG. 10.

As illustrated in FIG. 10, the p34 protein interacted with the wild-type NEDD4-1 protein but not with NEDD4-1 protein lacking the WW1 domain. From this, it is confirmed that p34 directly binds to the WW1 domain of NEDD4-1.

Example 1-5

Analysis of Effect of p34 on PTEN and NEDD4-1 Binding

In order to investigate whether p34 affects PTEN and NEDD4-1 binding, GST-PTEN fusion proteins were incubated with the lysing solution of cells expressing Myc-NEDD4-1 and His-p34, and then GST-pull down assay was performed. As a control group, GST proteins were used. The result is illustrated in FIG. 11.

As illustrated in FIG. 11, PTEN interacted with NEDD4-1 in the presence/absence of p34. However, these proteins more strongly interacted in the presence of p34 than in the absence of p34. This implies that p34 may affect the binding affinity of NEDD4-1 and PTEN.

From the above experimental result, it is confirmed that p34 interacts with the WW1 domain of NEDD4-1, but not with PTEN, and that p34 does not interfere with interaction between NEDD4-1 and PTEN. Also, from the above experimental result, it is understood that the enhanced stability of NEDD4-1 protein by p34 may affect poly-ubiquitination of PTEN.

Example 1-6

Analysis of Effect of p34 on Auto-Ubiquitination in Cells of NEDD4-1

(1) It was previously reported that NEDD4-1 was auto-ubiquitinated in cells. Thus, the effect of p34 on auto-ubiquitination of NEDD4-1 was analyzed. 293 cells were transfected with NEDD4-1 and/or p34, and the cells were treated with MG132 (25 mM) and incubated for 6 hours. Cell culture was obtained and its anti-Myc immunoprecipitates were analyzed. The result is illustrated in FIG. 12.

As illustrated in FIG. 12, in cells treated with MG132, NEDD4-1 auto-ubiquitination was significantly decreased upon the presence of p34.

(2) In order to verify the result, NEDD4-1 ubiquitination was analyzed in a cell-free system using purified proteins. First, His-tagged p34 was prepared from p34 cDNA expressing plasmids using His-tagged vectors. Purified GST-NEDD4-1 proteins were incubated with E1, UbcH5c and extracts from 293 cells expressing the His-tagged p34, and then auto-ubiquitination was measured. The result is illustrated in FIG. 13.

As illustrated in FIG. 13, p34 expression caused gradual decreases in GST-NEDD4-1 ubiquitination. From this, it is confirmed that p34 suppresses NEDD4-1 auto-ubiquitination in both intact cells and the cell-free system.

(3) 293 and MCF7 cells were transfected with plasmids expressing p34 for 24 hours or with small interfering RNA (siRNA) against p34 for 48 hours. The cells were treated with cycloheximide (CHX) (50 mg/ml) per each time, and Western blotting was performed to determine the NEDD4-1 protein. The results are illustrated in FIGS. 14 and 15.

As illustrated in FIG. 14, NEDD4-1 protein levels were greater and more sustained in cells that were co-transfected with GFP-tagged p34 and myc-tagged NEDD4-1 than in cells treated with myc-tagged NEDD4-1 alone.

Also, as illustrated in FIG. 15, NEDD4-1 protein levels in p34 knockdown cells using siRNA against p34 was significantly decreased compared with cells treated with scrambled siRNA. From this, it is confirmed that p34 stabilizes the NEDD4-1 protein.

This result strongly suggests that p34 suppresses NEDD4-1 auto-ubiquitination and thereby stabilizes the NEDD4-1 protein.

Example 2

Analysis of Effect of p34 on the Control of NEDD4-1-Mediated PTEN Poly-Ubiquitination (1) The silencing effect by inhibition of p34 expression was analyzed using siRNA of p34 (p34-siRNA: I: 5'-GCAAGG GUCUGAAGCGGAA-3' (SEQ ID NO 1), II: 5'-GGAAACGGGAGGAGGAGGA-3' (SEQ ID NO 2), III: 5'-CCGAAUUGGGACUACCUCAU-3' (SEQ ID NO 3)). MDA-MB-231 and MCF7 cells were transfected with p34-siRNA and the expression level of each protein was analyzed using Western blotting. The result is illustrated in FIG. 16.

As illustrated in FIG. 16, it is confirmed that p34-siRNA induces a dose-dependent increase in PTEN expression levels and a decrease in p-Akt expression levels.

Also, 293 and mouse embryonic fibroblasts (MEF) cells were transfected with GFP-tagged p34, and then the expression levels of each protein were analyzed using Western blotting. The result is illustrated in FIG. 17.

As illustrated in FIG. 17, the expression of GFP-tagged p34 decreased levels of PTEN protein in 293 or MEF cells, which do not express endogenous p34. Also, the levels of Akt phosphorylation increased depending on p34 expression levels, and were in inverse proportion to PTEN expression levels.

From the above, it is confirmed that p34 may affect PTEN protein levels by binding to NEDD4-1.

(2) On the basis of the above experimental result, the present inventors investigated the role of p34 in regulating PTEN turnover by transfecting MCF7 cells with p34-siRNA, treating the cells with cycloheximide (CHX), a protein synthesis inhibitor, and measuring a change in endogenously expressed p34 protein levels over time. The result is illustrated in FIG. 18.

As illustrated in FIG. 18, when p34 in MCF7 cells endogenously expressing p34 was knockdown using p34-siRNA, PTEN protein levels remained substantially unchanged, but the PTEN expression decreased in cells transfected with control group siRNA (scrambled siRNA). This result means that p34 positively regulates the PI3K signaling pathway by decreasing PTEN protein stability.

(3) In order to confirm whether p34 regulates stability of PTEN protein through protein degradation pathway, 293 cells which do not endogenously express p34 were transfected with GFP-tagged p34, and then treated with the proteasome inhibitor MG132. The expression levels of each protein were analyzed using Western blotting. The result is illustrated in FIG. 19.

As illustrated in FIG. 19, PTEN protein levels in cells exogenously expressing p34 and treated with MG132 significantly decreased compared with cells transfected with the control group vector (empty vector).

(4) In order to further confirm whether p34 affects PTEN poly-ubiquitination, intracellular ubiquitination assay was performed.

First, 293 or MEF cells were transfected with GFP-p34, and then incubated with MG132. PTEN ubiquitination was analyzed. The result is illustrated in FIG. 20.

As illustrated in FIG. 20, the poly-ubiquitinated form of PTEN was detected in 293 cells or MEF cells treated with MG132 after ectopically expressing p34.

Also, MCF7, MDA-MB-231, and DU145 cells were transfected with p34-siRNA for 24 hours, and then incubated with MG132. PTEN ubiquitination was analyzed. The result is illustrated in FIG. 21.

As illustrated in FIG. 21, PTEN poly-ubiquitination gradually decreased in p34-knockdown MCF7, MDA-MB-231, and DU145 cells.

Further, 293 cells were transfected with wild-type PTEN and/or p34 for 24 hours, and then PTEN lipid phosphatase activity was measured. Specifically, the cells were lysed in 50 mM HEPES (pH 7.5), 150 mM NaCl, 1 mM EDTA, 10% glycerol, and 1% Triton X-100 buffer containing protease inhibitor, and then PTEN was immunoprecipitated using an anti-PTEN antibody. The immunoprecipitates were washed and incubated with water-soluble diC8-phosphatidylinositol 3,4,5-trisphosphate in 100 mM Tris-HCl (pH 8.0) and 10 mM DTT at 37° C. for 40 minutes. Thereafter, the supernatants were collected and incubated with Biomol Green Reagent (Enzo Life Sciences) at room temperature for 30 minutes. PTEN activity was determined by measuring the release of phosphate by measurement of an OD value at 650 nm. As a negative control group, the lipid phosphatase-deficient PTEN C124S mutant where cystein of $123^{rd}$ amino acid is mutated to serine was used. The result is illustrated in FIG. 22.

As illustrated in FIG. 22, the lipid phosphatase activity of PTEN significantly decreased in cells ectopically expressing p34 compared with the control group.

This result indicates that p34 mediates the poly-ubiquitination and proteasomal degradation of PTEN.

(5) PTEN ubiquitination and proteasomal degradation were recently reported to be controlled in part by NEDD4-1, which functions as an E3 ubiquitin ligase (Wang et al., 2007). As the present inventors found in Example 1 that p34 directly interacts with NEDD4-1, the present inventors investigated whether the effects of NEDD4-1 on PTEN ubiquitination and proteasomal degradation are dependent upon p34 expression levels.

First, 293 cells or MEF cells, which express endogenous NEDD4-1 but do not express p34, were co-transfected with GFP-tagged p34 plasmids (or GFP control vector) and NEDD4-1-siRNA/shRNA (or scrambled siRNA) (NEDD4-1-siRNA: 5'-TGGCGATTTGTAAACCGAA-3' (SEQ ID NO 4)). The expression levels of each protein were analyzed using Western blotting. The result is illustrated in FIG. 23.

As illustrated in FIG. 23, the levels of PTEN protein remained substantially unchanged in cells that were co-transfected with NEDD4-1-siRNA/shRNA and GFP-tagged p34 but significantly decreased in cells that were transfected with GFP-tagged p34 alone. The levels of Akt phosphorylation were consistently in inverse proportion to the levels of PTEN protein.

(6) In the presence of cycloheximide (CHX), a protein synthesis inhibitor, it was investigated whether PTEN turnover is affected by ectopic expression of p34 and NEDD4-1 knockdown. To this end, 293 cells were transfected with p34 expression plasmids and NEDD4-1 siRNA, and then the half-life of PTEN protein was analyzed. The result is illustrated in FIG. 24.

As illustrated in FIG. 24, PTEN levels decreased in NEDD4-1-knockdown 293 cells upon exogenous p34 expression but gradually increased after CHX treatment. From this, it is confirmed that p34 mediates the proteasomal degradation of PTEN depending upon NEDD4-1.

(7) In order to confirm whether p34 mediates the PTEN poly-ubiquitination dependent upon NEDD4-1, wild-type (293 or MEF cells) and NEDD4-1 knockdown cells were transfected with p34 expression plasmids, and then treated with MG132. Then, Intact-cell ubiquitination assay was performed. The result is illustrated in FIG. 25.

As illustrated in FIG. 25, poly-ubiquitinated PTEN was clearly detected in wild-type cells which were transfected with p34 expression plasmids, but not in NEDD4-1 knockdown cells which were transfected with p34 expression plasmids.

Also, the PTEN lipid phosphatase activity in the 293 cells was analyzed. The result is illustrated in FIG. 26.

As illustrated in FIG. 26, it was confirmed that the PTEN lipid phosphatase activity was retained in NEDD4-1-knockdown of 293 cells ectopically expressing p34, but was lost in cells which were treated with scrambled siRNA.

This result indicates that NEDD4-1 induced PTEN poly-ubiquitination dependent upon p34.

(8) XIAP was recently reported to induce PTEN poly-ubiquitination (Van Themsche et al., 2009). To evaluate whether p34 affects XIAP-induced PTEN poly-ubiquitination, poly-ubiquitination experiments were performed in XIAP-knockout MEF cells. The XIAP-knockout MEF cells were provided by Dr. Duckett (University of Michigan Medical School). The results are illustrated in FIGS. 27 to 29.

As illustrated in FIG. 27, it is confirmed that in XIAP-knockout MEF cells, no expression of XIAP was observed using Western blotting.

Also, as illustrated in FIG. 28, it is confirmed that transfection of XIAP-knockout MEF cells with GFP-tagged p34 significantly decreased the levels of PTEN protein.

Also, as illustrated in FIG. 29, it is confirmed that PTEN in XIAP-knockout MEF cells which were transfected with GFP-tagged p34 was strongly poly-ubiquitinated.

From the above results, it is confirmed that p34 regulates the NEDD4-1-mediated poly-ubiquitination of PTEN in an XIAP-independent manner.

Example 3

Analysis of p34 Control of NEDD4-1 Mediated PTEN Mono- and Poly-Ubiquitination (1) It has been recently reported that NEDD4-1 mediates PTEN mono-ubiquitination as well as its poly-ubiquitination in vitro and in vivo, and that PTEN nuclear import is mediated by its mono-ubiquitination (Wang et al., 2007). As illustrated in Example 2, it is confirmed that p34 controls NEDD4-1-mediated PTEN poly-ubiquitination. Based on the above results, the present inventors analyzed whether p34 affects PTEN mono-ubiquitination.

First, 4 cancer cell lines (MCF7, MDA-MB231, DU145, and LS1034) which endogenously express p34 and NEDD4-1 were transfected with p34-siRNA, and ubiquitination of PTEN was examined using intact-cell ubiquitination assay. The result is illustrated in FIG. 30.

As illustrated in FIG. 30, p 34 knockdown increased mono-ubiquitinated PTEN in all cancer cell lines.

Further, MCF7 cells were transfected with p34-siRNA for 24 hours, and fractionated into nuclear and cytosolic compartments. The PTEN expression was analyzed using Western blotting. The result is illustrated in FIG. 31.

As illustrated in FIG. 31, PTEN proteins were strongly detected in the nuclear fraction of p34-knockdown MCF7 cells, but almost no cells which were treated with scrambled siRNA displayed PTEN nuclear localization. Further, mono-ubiquitinated PTEN was detected only in the nuclear fractions of p34-knockdown MCF7 cells. This indicates that the expression of p34 affects PTEN mono-ubiquitination and nuclear localization.

(2) To investigate whether NEDD4-1 affects PTEN mono-ubiquitination upon p34 expression, MCF7 cells were transfected with NEDD4-1-siRNA, p34-siRNA, and/or GFP-tagged p34 for 24 hours. Then, PTEN ubiquitination was analyzed. The result is illustrated in FIG. 32.

As illustrated in FIG. 32, mono-ubiquitinated PTEN was observed in p34-knockdown cells, but was not observed in cells which were co-transfected with NEDD4-1-siRNA and p34-siRNA.

(3) To verify this observation, the present inventors incubated purified GST-PTEN proteins with protein extracts from 293 cells expressing Flag-tagged NEDD4-1 and/or His-tagged p34 in the presence of E1 and E2 enzymes. Then, cell-free ubiquitination assay of GST-PTEN was performed. The results are illustrated in FIGS. 33 and 34.

As illustrated in FIG. 33, PTEN was mono-ubiquitinated in case where NEDD4-1 is present alone, whereas PTEN was strongly poly-ubiquitinated in case where both NEDD4-1 and p34 are present.

Furthermore, as illustrated in FIG. 34, PTEN poly-ubiquitination gradually decreased in p34-dependent manner. This means that NEDD4-1-mediated PTEN mono- and poly-ubiquitination are dependent upon the expression of p34.

(4) Whether p34 acts as an E2-like enzyme in NEDD4-1-mediated PTEN ubiquitination was investigated. GST-PTEN was incubated with p34 and NEDD4-1 in the presence or absence of E1 and E2, and then PTEN ubiquitination was analyzed using cell-free ubiquitination assay. The result is illustrated in FIG. 35.

As illustrated in FIG. 35, purified GST-PTEN was ubiquitinated in extracts obtained from 293 cells expressing Flag-tagged NEDD4-1 and His-tagged p34 in the presence of E2 enzyme, but was not ubiquitinated in the absence of E2 enzyme. From this, it can be understood that p34 does not function as an E2-like enzyme. Thus, it can be understood that p34 may control NEDD4-1-mediated PTEN mono- and poly-ubiquitination.

Example 4

Analysis of Correlation Between p34 and Cancer Cell Proliferation

From the experimental results of Examples 1 to 3 above, it is confirmed that p34 positively controls stability of NEDD4-1 protein by inhibiting NEDD4-1 auto-ubiquitination, and thus that p34 knockdown decreased PTEN poly-ubiquitination and increased the levels of PTEN protein by NEDD4-1-mediated PTEN mono-ubiquitination.

(1) In order to confirm whether p34 functions as a strong proto-oncogene in the NEDD4-1/PTEN pathway, the proliferation of MCF7 and LS1034 cells expressing p34-siRNA was examined. Colony-forming assay and soft-agar assay were performed.

To perform colony-forming assay, the clonogenic capacity was determined by plating the cells in a concentration of 300 cells per 6-well plate. 10 to 14 days after plating, the cells were fixed and stained with a solution of 0.01% crystal violet.

Soft-agar assay was performed as follows. Soft-agar plates were prepared by adding 1.6% agarose in 2×DMEM or 2×RPMI-1640 supplemented with 10% FBS to 6-well plates. The cells ($1 \times 10^4$) which were floated in 0.7% agarose and 2×DMEM or 2×RPMI-1640 supplemented with 10% FBS were seeded. The plates were then incubated for 2 to 3 weeks in a 37° C. incubator. The colonies were counted under a microscope.

The results are illustrated in FIGS. 36 to 38.

As illustrated in FIG. 36, the growth of MCF7 and LS1034 cells expressing p34-siRNA remarkably decreased compared with cells expressing scrambled siRNA.

Furthermore, as illustrated in FIGS. 37 and 38, the frequency of colony formation of cells treated with p34-siRNA dramatically decreased compared with the control group (FIG. 27), and the sizes of the colonies also decreased (FIG. 38).

(2) The expression levels of cyclin E2 and cdc6 genes, target genes of PTEN, were confirmed using RT-qPCR analysis as follows. Cells were transfected with p34-siRNA or scrambled siRNA. Then, total RNA was isolated from the cells using TRIzol (Invitrogen). Complementary DNA (cDNA) was prepared using RT premix (Bioneer, Daejeon, Korea) and oligo dT16-18 primers. Thereafter, RT-qPCR was performed on p34, cdc6, cyclin E2 genes using the primer sets in the following Table 1. The result is illustrated in FIG. 39.

TABLE 1

| | | |
|---|---|---|
| p34 | F | 5'-TGGCCTCTAGCTCCCTCTTT-3' (SEQ ID NO: 5) |
| | R | 5'-GCCAGTAAGTTGTCAGCCACA-3' (SEQ ID NO: 6) |
| cdc6 | F | 5'-CAGGTTCTGGACAATGCTGC-3' (SEQ ID NO: 7) |

TABLE 1-continued

| | | |
|---|---|---|
| | R | 5'-CTGCTGAAGAGGGAAGGAATC-3' (SEQ ID NO: 8) |
| cyclin E2 | F | 5'-TGCTGCCTTGTGCCATTT-3' (SEQ ID NO: 9) |
| | R | 5'-GTGCTCTTCGGTGGTGTCATA-3' (SEQ ID NO: 10) |
| GAPDH | F | 5'-AGAAGGCTGGGGCTCATTTG-3' (SEQ ID NO: 11) |
| | R | 5'-AGGGGCCATCCACAGTCTTC-3' (SEQ ID NO: 12) |

As illustrated in FIG. 39, the expression levels of the cyclin E2 and cdc6 genes, which are target genes of PTEN, were reduced in p34-knockdown cells. From this, it is confirmed that p34 knockdown inhibits cancer cell growth by downregulating cyclin E2 and cdc6 genes.

(3) To further examine the inhibitory effects of p34 knockdown on cancer cell proliferation, the present inventors established mutants of DU145 and MDA-MB-231 cell lines that stably express tetracycline-inducible p34-shRNA vectors. First, the DU145 and MDA-MB231 TetR were transfected with the TetR-expressing plasmid, pcDNA6.0/TR (Invitrogen), and selected with blasticidin 10 μg/ml for 3 weeks. TetR-expressing clone cells were confirmed from immunoblot analysis with an anti-TetR antibody. Two TetR-overexpressing clones were transfected again with the H1-p34-shRNA vector (5'-CCCTCTTTGACCTCTCAGT-3' (SEQ ID NO 13)), and these cells were selected with zeocin (300 mg/ml) for 3 weeks to establish tet-on inducible p34 cell lines. They are exposed to tetracycline, and then clones of mutants of DU145 or MDA-MB231 expressing TetR were selected. After treating the mutants with tetracycline, the expression of each protein was analyzed using Western blotting. Also, PTEN lipid phosphatase activity assays and colony-forming assays of the mutants were performed. The results are illustrated in FIGS. 40 to 43.

As illustrated in FIG. 40, it is confirmed that the DU145 or MDA-MB231 mutants expressed TetR expression. Also, as illustrated in FIG. 41, it is confirmed that when the DU145 or MDA-MB231 mutants were treated with tetracycline (Tet; 1 mg/ml), p34 expression was inhibited, and that the PTEN expression increased. The levels of phosphorylated Akt were in inverse proportion to PTEN expression levels.

Also, as illustrated in FIG. 42, the treatment of the DU145 or MDA-MB231 mutants with tetracycline resulted in an increase in the PTEN lipid phosphatase activity.

Also, as illustrated in FIG. 43, the treatment of the DU145 or MDA-MB231 mutants with tetracycline resulted in a remarkable decrease in colony formation.

Additionally, the cell growth of the DU145 or MDA-MB231 mutants was observed and BrdU assays were performed. The results are illustrated in FIGS. 44 and 45.

As illustrated in FIG. 44, the growth of cells treated with tetracycline dramatically decreased compared with cells not-treated with tetracycline.

Also, as illustrated in FIG. 45, for cells treated with tetracycline, BrdU incorporation was remarkably reduced.

(4) In order to prepare cells stably overexpressing p34, Hs578T cells where p34 is not detected were transfected with the retroviral vector pBabe-puro (control group) or pBabe-puro-p34, and then selected using puromycin (2 μg/ml) for 2 weeks. The expression of p34 was confirmed by Western blotting using anti-p34 antibodies. In order to analyze proteins of the cells prepared according to the above process, Western blotting was performed, and colony formation was observed. The result is illustrated in FIG. 46.

As illustrated in FIG. 46, the expression of PTEN decreased and colony formation significantly increased in Hs578T cells which stably express p34, compared with cells which express the control group vector.

From these results, it is confirmed that p34 inhibits cancer cell proliferation through PTEN.

Example 5

Reinforcement of p34 Tumorigenicity (1) In order to confirm whether the p34 expression affects the proto-oncogenic properties of NEDD4-1, the following experiments were performed using the DU145 and MDA-MB-231 mutants which are inducible from tetracycline established in Example 4-(3) above, and stably express p34 shRNA and thereby depleting p34 expression. Xenograft tumor was formed by injecting the established cells to Balb/c nude mice subcutaneously. The size of tumor was observed every 3 days for 2 weeks. When the size of tumor reached 180 mm$^3$, it was set as day 0, and tetracycline in a concentration of 10 mg/kg was administered (water was administered to the control group as a vehicle), and then the size of tumor was continuously monitored. All of the animal experiments were processed according to animal protocols that had been approved by the Asan Medical Center Institutional Animal Care and Use Committee. The results are illustrated in FIGS. 47 to 52.

As illustrated in FIGS. 47 and 48, the expression of PTEN increased and the expression of NEDD4-1 decreased in the group which was injected with the p34-shRNA-transfected DU145 mutants or p34-shRNA-transfected MDA-MB-231 mutants, and administered with tetracycline.

Also, as illustrated in FIGS. 49 and 50, the growth of tumor induced by the injection of the p34-shRNA-transfected DU145 mutants or p34-shRNA-transfected MDA-MB-231 mutants significantly decreased in the case administered with tetracycline, compared with the control group.

Also, as illustrated in FIGS. 51 and 52, as a result of immunohistochemistry of each mouse tumor cell, it is confirmed that PTEN protein displayed strong nuclear localization after tetracycline administration.

From these results, it is confirmed that p34 reinforces the proto-oncogenic activity of NEDD4-1.

(2) To verify the effect of p34 on the proto-oncogenic activity of NEDD4-1, the present inventors utilized p53-null MEF (p53$^{-/-}$/MEF) cells, which do not express endogenous p34 (Millipore, Billerica, Mass., USA). NEDD4-1 alone is not proto-oncogenic; however, the study result was reported that the overexpression of NEDD4-1 enhances the Ras-mediated transformation of p53-null MEF cells (Wang et al., 2007). On the basis of this report, the present inventors first investigated the effect of p34 expression on the Ras-mediated transformation of p53-null MEF cells. The protein expression and colony formation assays of p53$^{-/-}$/MEF cells were performed. The results are illustrated in FIGS. 53 and 54.

As illustrated in FIG. 53, as a result of analyzing the protein expression in p53$^{-/-}$/MEF cells, the p34 expression caused a decrease in PTEN expression and an increase in NEDD4-1 expression.

Also, as illustrated in FIG. 54, as a result of colony formation assays in p53$^{-/-}$/MEF cells, the p34 expression increased cell colony numbers compared with p53$^{-/-}$/MEF cells expressing Ras.

(3) The proto-oncogenic activity of p34 was observed in NEDD4-1 knockdown-p53-null (p53$^{-/-}$) MEF cells prepared using retroviral-based shRNA vectors. The protein expression, colony formation, and ubiquitination of NEDD4-1 knockdown-p53-null (p53$^{-/-}$) MEF cells were analyzed. The results are illustrated in FIGS. 55 to 57.

As illustrated in FIG. 55, the expression of p34 in NEDD4-1 knockdown-p53-null (p53$^{-/-}$) MEF cells did not cause a decrease in PTEN.

Also, as illustrated in FIG. 56, as a result of colony formation assays, despite the p34 expression in NEDD4-1 knockdown-p53$^{-/-}$ MEF cells, the cell formation was inhibited.

Also, as illustrated in FIG. 57, as a result of ubiquitination assays, the p34 expression caused the poly-ubiquitination of PTEN in the control group p53-null MEF cells expression shRNA, whereas did not cause the poly-ubiquitination of PTEN in NEDD4-1 knockdown-p53$^{-/-}$ MEF cells expressing NEDD4-1 shRNA. This indicates that p34 enhances the Ras-mediated transformation of p53-null MEF cells in a NEDD4-1 dependent manner.

(4) In order to determine whether the effects of p34 on the proto-oncogenic activity of NEDD4-1 are PTEN-dependent, Western blotting assays and colony formation assays were performed using p53-null MEF cells expressing PTEN shRNA. The result is illustrated in FIG. 58.

As illustrated in FIG. 58, the p34 expression in the MEF cells failed to enhance the transforming activity of Ras. This indicates that p34 enhances the proto-oncogenic activity of NEDD4-1 in a PTEN-dependent manner.

(5) The clinical relevance of p34, NEDD4-1, and/or PTEN in human cancer tissues was investigated. In consideration of the functions of p34 as a positive regulator of NEDD4-1 mediated PTEN ubiquitination, there was a possibility that the p34 expression in human cancer tissues might affect a decrease in the levels of PTEN induced by NEDD4-1 in human cancer cells. In order to verify this, the present inventors assessed the expression of p34, NEDD4-1, and PTEN in paraffin-embedded tissue microassays (TMA) of 135 isolated breast cancers and 191 colon cancers.

90 breast cancer samples (66.7%) among 135 breast cancer tissues were detected as p34-positive, and 45 samples (33.3%) were detected as p34-negative. Also, the expression of NEDD4-1 was detected in 85 samples (94.4%) among p34-positive 90 samples, and almost all (58/85; 68.2%) of NEDD4-1/p34-positive samples expressed PTEN protein. NEDD4-1 was highly expressed even in p34-negative samples (45/45; 100%). However, in p34-positive samples, only a small number (21/45; 46.67%) expressed PTEN.

Also, 177 colony cancer samples (61.3%) among 191 colony cancer tissues were detected as p34-positive, and 74 samples (38.7%) were detected as p34-negative. Also, the expression of PTEN was detected in a small number of samples (11.8%) among 127 NEDD4-1/p34 double-positive samples. On the other hand, only 8 samples among 149 NEDD4-1 positive samples which do not express p34 expressed PTEN.

As illustrated in FIGS. 59 and 60, in breast cancer and colon cancer samples, there is a significant inverse correlation between p34, NEDD4-1, and PTEN expression levels, but in colon cancer samples, p34 negative and NEDD4-1 positive did not affect the level of PTEN.

Thus, from the above results, it can be inferred that the expression of p34 in human breast cancer and colon cancer contribute to the proto-oncogenic activity of NEDD4-1 in a PTEN dependent manner.

FIG. 61 illustrates a schematic diagram of general interaction between p34, NEDD4-1 and PTEN.

Example 6

Verification of p34 Activity Inhibitor on Anticancer Activity

As confirmed from Examples 1 to 5 above, experiments for verifying whether the p34 activity inhibitor actually has anticancer activity were performed. First, a compound which inhibits the activity of p34 by binding to p34 protein was identified through compound library screening sold on the market. The formula of the identified compound was represented as follows, and hereinafter, it is referred to as Compound 27.

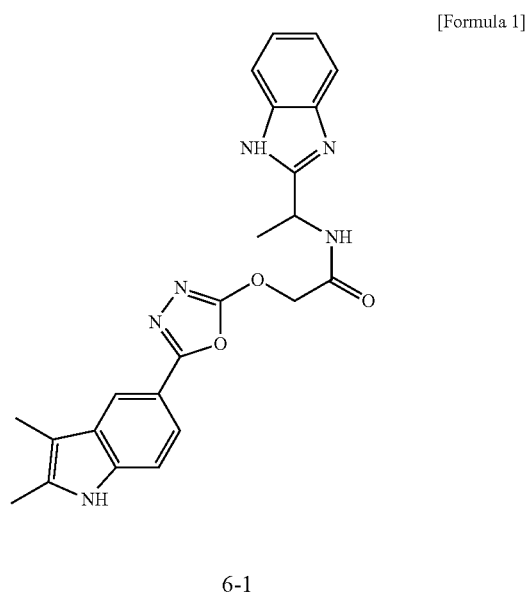

[Formula 1]

6-1

Verification of p34 Activity Inhibitor on PTEN Ubiquitination

The p34 activity inhibitor, Compound 27, in a concentration of 1 μM was treated with human breast cancer cell lines MDA-MB-231 and colorectal cancer cell lines LS1034 for 24 hours, and immunoprecipitation was performed using a PTEN antibody. Thereafter, Western blotting was performed using an ubiquitin antibody. The result is illustrated in FIG. 62.

As illustrated in FIG. 62, it is confirmed that the p34 activity inhibitor, Compound 27, has the activity of inhibiting PTEN ubiquitination in human breast cancer and colorectal cancer cells.

6-2

Verification of p34 Activity Inhibitor on p34 and NEDD4-1 Proteins Binding

Purified NEDD4-1 protein and p34 protein were treated with a reaction buffer (20 mM Tris-HCl pH7.5, 120 mM NaCl) and the p34 activity inhibitor Compound 27 in a concentration of 1 mM or 3 mM, and reacted at 30° C. for 1 hour. Thereafter, the reaction was stopped using GST-pull down buffer (20 mM Tris-HCl pH8.0, 500 mM NaCl, 1%

Triton X-100, 0.02% BSA, 5 mM mercaptoethanol), and then pulled down with glutathione-sepharose beads at 4° C. Western blotting was performed using anti-His and anti-GST antibodies. The result is illustrated in FIG. 63.

As illustrated in FIG. 63, it is confirmed that the treatment with the p34 activity inhibitor Compound 27 inhibited the p34 protein and the NEDD4-1 protein binding in a dose dependent manner.

6-3

Verification of p34 Activity Inhibitor on Anticancer Effect Through PTEN Reactivity Induction Human breast cancer cell lines MDA-MB-231 were treated with the p34 activity inhibitor Compound 27 per each concentration for 48 hours, and then trypan blue dye and Western blotting were performed. The result is illustrated in FIG. 64.

As illustrated in FIG. 64, in breast cancer cells, cell death was induced in a p34 activity inhibitor Compound 27 dose-dependent manner, the PTEN protein was reactivated, and accordingly, Akt dephosphorylation occurred and caspase3 was activated. From this, it is confirmed that the treatment with p34 activity inhibitor inhibits p34-NEDD4-1 proteins binding, which results in reactivating PTEN and inducing cell death.

Also, human breast cancer cell lines MDA-MB-231 were treated with p34 activity inhibitor Compound 27 per each concentration for 48 hours, and cell sap was collected and immunoprecipitation was performed using a PTEN antibody. Thereafter, it was reacted with a reaction buffer solution (100 mM Tris-HCl pH8.0, 10 mM DTT) containing water-soluble diC8-phosphatidylinositol 3,4,5 tri-phosphate at 37° C. for 40 minutes, and only the supernatant was collected to be reacted with Biomol Green solution at room temperature for 30 minutes. Then, PTEN lipid phosphatase activity was measured at OD 650 nm. The result is illustrated in FIG. 65.

As illustrated in FIG. 65, it was confirmed that the treatment of breast cancer cells with p34 activity inhibitor Compound 27 increased PTEN lipid phosphatase activity.

The same experiments were performed using human colorectal cancer cell lines LS1034. The results are illustrated in FIGS. 66 and 67.

As illustrated in FIG. 66, in colorectal cancer cells, cell death was induced in the p34 activity inhibitor Compound 27 dose-dependent manner, the PTEN protein was reactivated, and accordingly, Akt dephosphorylation occurred and caspase3 was activated.

Also, as illustrated in FIG. 67, the treatment of colorectal cancer cells with the p34 activity inhibitor Compound 27 increased PTEN lipid phosphatase activity.

Hereinafter, preparation examples of the pharmaceutical composition and food composition of the present invention are described for illustrative purposes only, and the present invention is not intended to be limited by the following preparation examples.

Preparation Example 1

Preparation of Pharmaceutical Formulations

| 1. Preparation of powders | |
|---|---|
| p34 expression or activity inhibitor | 2 g |
| lactose | 1 g |

The above ingredients were mixed and filled in a sealed pouch to prepare a powder formulation.

| 2. Preparation of tablets | |
|---|---|
| p34 expression or activity inhibitor | 100 mg |
| corn starch | 100 mg |
| lactose | 100 mg |
| magnesium stearate | 2 mg |

The above ingredients were mixed and tableted according to a general tableting method to prepare a table formulation.

| 3. Preparation of capsules | |
|---|---|
| p34 expression or activity inhibitor | 100 mg |
| corn starch | 100 mg |
| lactose | 100 mg |
| magnesium stearate | 2 mg |

The above ingredients were mixed and filled into a gelatin capsule according to a general capsule preparation method to prepare the formulation a capsule formulation.

Preparation Example 2

Preparation of Food Formulations

| 1. Preparation of health care food | |
|---|---|
| p34 expression or activity inhibitor | 100 mg |
| vitamin mixture | adequate |
| vitamin A acetate | 70 g |
| vitamin E | 1.0 mg |
| vitamin B1 | 0.13 mg |
| vitamin B2 | 0.15 mg |
| vitamin B6 | 0.5 mg |
| vitamin B12 | 0.2 g |
| vitamin C | 10 mg |
| biotin | 10 g |
| nicotinic acid amide | 1.7 mg |
| folic acid | 50 g |
| calcium pantothenate | 0.5 mg |
| mixture of minerals | adequate |
| ferrous sulfate | 1.75 mg |
| zinc oxide | 0.82 mg |
| magnesium carbonate | 25.3 mg |
| potassium phosphate, monobasic | 15 mg |
| calcium phosphate, dibasic | 55 mg |
| potassium citrate | 90 mg |
| calcium carbonate | 100 mg |
| magnesium chloride | 24.8 mg |

In the above composition including vitamins and minerals, the ingredients are mixed in a ratio appropriate for a health care food, but the mixing ratio may be changed. A health care food composition may be prepared according to a conventional method of preparing a health care food, the method including the steps of mixing the above ingredients, preparing granules, and using the granules in the same manner as the conventional method.

What is claimed is:

1. A method for treatment or metastasis suppression of a cancer, wherein the cancer is selected from the group consisting of: breast cancer, colon cancer and prostate cancer, the method comprising administering to an individual the p34 protein activity inhibitor of formula 1 or a pharmaceutically acceptable salt thereof:

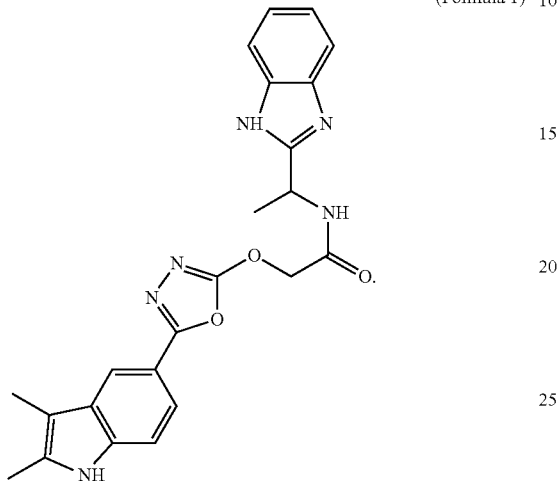

(Formula 1)

2. The method of claim 1, wherein the cancer simultaneously expresses p34 and neuronal precursor cell-expressed developmentally down-regulated 4-1(NEDD4-1).

* * * * *